(12) United States Patent
Bharti

(10) Patent No.: US 8,993,309 B2
(45) Date of Patent: Mar. 31, 2015

(54) PREDICTIVE MARKER FOR TOPOISOMERASE I INHIBITORS

(75) Inventor: Ajit Bharti, West Roxbury, MA (US)

(73) Assignee: Boston Medical Center Corporation, Boston, MA (US)

(*) Notice: Subject to any disclaimer, the term of this patent is extended or adjusted under 35 U.S.C. 154(b) by 464 days.

(21) Appl. No.: 12/935,812

(22) PCT Filed: Mar. 31, 2009

(86) PCT No.: PCT/US2009/038981
§ 371 (c)(1),
(2), (4) Date: Sep. 30, 2010

(87) PCT Pub. No.: WO2009/124064
PCT Pub. Date: Oct. 8, 2009

(65) Prior Publication Data
US 2011/0027277 A1 Feb. 3, 2011

Related U.S. Application Data

(60) Provisional application No. 61/072,490, filed on Mar. 31, 2008.

(51) Int. Cl.
*G01N 33/574* (2006.01)
*G01N 33/68* (2006.01)

(52) U.S. Cl.
CPC .......... *G01N 33/6842* (2013.01); *G01N 33/574* (2013.01); *G01N 2333/99* (2013.01); *G01N 2800/52* (2013.01)
USPC ...................... 435/287.2; 435/7.23; 424/133.1

(58) Field of Classification Search
USPC ................................ 424/133; 435/287.2, 7.23
See application file for complete search history.

(56) References Cited

U.S. PATENT DOCUMENTS

| | | | |
|---|---|---|---|
| 4,031,098 A | 6/1977 | Sugasawa | |
| 4,473,692 A | 9/1984 | Miyasaka et al. | |
| 4,545,880 A | 10/1985 | Miyasaka et al. | |
| 4,604,463 A | 8/1986 | Miyasaka et al. | |
| 5,049,668 A | 9/1991 | Wall et al. | |
| 5,106,742 A | 4/1992 | Wall et al. | |
| 5,364,858 A | 11/1994 | Wall et al. | |
| 5,468,754 A | 11/1995 | Hausheer et al. | |
| 5,604,233 A | 2/1997 | Hausheer et al. | |
| 5,674,873 A | 10/1997 | Hausheer et al. | |
| 5,731,316 A | 3/1998 | Cao et al. | |
| 5,807,874 A | 9/1998 | LaVoie et al. | |
| 6,660,861 B1 | 12/2003 | Puri et al. | |
| 7,270,808 B2 | 9/2007 | Cheng et al. | |
| 2008/0280935 A1 | 11/2008 | Naidu | |

FOREIGN PATENT DOCUMENTS

| | | |
|---|---|---|
| EP | 0074256 | 11/1986 |
| JP | 2005-029573 | 2/2005 |
| JP | 2006-038614 | 2/2006 |
| JP | 2007-223902 | 9/2007 |
| JP | 2008-045976 | 2/2008 |
| WO | 2006/081331 | 8/2006 |
| WO | 2008/021549 | 2/2008 |
| WO | 2008/021549 A2 | 2/2008 |
| WO | WO 2008/021549 A2 | 2/2008 |

OTHER PUBLICATIONS

Pommier, "Topoisomerase I inhibitors: camptothecins and beyond." (2006) Nature Reviews: Cancer, 6, 789-802.*
Masters, "HeLa cells 50 years on: the good, the bad and the ugly." (2002) Nature Reviews: Cancer, 2, 315-318.*
Gloffke, "Detecting Protein Phosphorylation" (2002) The Scientist, article No. 14,271.*
Bharti, A.K. et al. "Identification of a Nucleolin Binding Site in Human Topoisomerase I" The Journal of Biological Chemistry 1996; vol. 271, No. 4, pp. 1993-1997.
Cardellini, E. et al. "Human Topoisomerase I is Phosphorylated in vitro on its Amino Terminal Domain by Protein Kinase NII" Biol. Chem. Hoppe-Seler. Apr. 1994; vol. 375, pp. 255-259.
Coderoni, S. et al. "Phosphorylation Sites for Type N II Protein Kinase in DNA-Topoisomerase I From Calf Thymus" Int. J. Biochem. 1989; vol. 22, No. 7, pp. 737-746.
Corey, E. J. et al. "A Total Synthesis of Natural 20(S)-Camptothecin" J. Org. Chem. 1975, 40, pp. 2140-2141.
Desai, S. D. et al. "Ubiquitin-dependent Destruction of Topoisomerase I is Stimulated by the Antitumor Drug Camptothecin" The Journal of Biological Chemistry Sep. 1997; vol. 272, pp. 24159-24164.
Gallo R.C. et al. "Studies on the Antitumor Activity, Mechanism of Action, and Cell Cycle Effects of Camptothecin" Journal of the National Cancer Institute Apr. 1971; vol. 46, No. 4, pp. 789-795.

(Continued)

*Primary Examiner* — Jon P Weber
*Assistant Examiner* — Teresa E Knight
(74) *Attorney, Agent, or Firm* — Nixon Peabody LLP

(57) ABSTRACT

The present invention generally relates to the fields of cancer therapy and cancer prevention. More particularly, the present invention generally relates to a diagnostic marker for predicting the efficacy of topoisomerase I (topo I) inhibitors in the treatment of cancers. More specifically, the present invention relates to methods, machines, computer systems, computable readable media and kits which can be used to identify and determine the effectiveness of topoisomerase I (topo I) inhibitors in the treatment of cancers, and in some embodiments, the level of sensitivity or resistance of a tumor cell to a topoisomerase I inhibitor, such as camptothecin (CPT), or CTP analogues such as topotecan and irinotecan and derivatives thereof. More specifically, the present invention related to methods, machines, computer systems, computable readable media and kits which can be used to determine the presence of phosphorylation of topoisomerase I polypeptide, in some embodiments phosphorylation at residue serine 10 (S10) of a topoisomerase I polypeptide, wherein the presence of phosphorylation, in particular the phosphorylation at serine 10 of a topoI polypeptide indicates a cancer is likely to be unresponsive to a topo I inhibitor, whereas the absence of phosphorylation, in particular, the absence of phosphorylation at residue serine 10 (S10) identifies a cancer is likely to be responsive to a topo I inhibitor. Other aspect of the present invention relate to phospho-serine 10 topoisomerase I antibodies and other protein binding moieties, and uses thereof.

7 Claims, 25 Drawing Sheets

(56) References Cited

OTHER PUBLICATIONS

Giovanella B.C. "Complete Growth Inhibition of Human Cancer Xenografts in Nude Mice by Treatment with 20-(S)-Camptothecin" Cancer Research Jun. 1991; 51, pp. 3052-3055.

Kametani, T. et al. "Studies on the Syntheses of Heterocyclic Compounds. Part 878. Synthesis of (±)- Camptothecin and (±)-10-Methoxycamptothecin via Enamine Annulation" J. Chem. Soc. Perkin Trans. 1 1981 #11, pp. 1981-1568.

Sanchez-Perez, I. "DNA repair inhibitors in cancer treatment" Clin. Transl. Oncol. 2006; 8(9): pp. 646-646.

Shanghai Institute of Materia Medica et al. "The Total Synthesis of dl-Camptothecin" Scientia Sinica, vol. XXI No. 1 Jan.-Feb. 1978, pp. 88-98.

Sørlie, T. et al. "Gene expression patterns of breast carcinomas distinguish tumor subclasses with clinical implications" PNAS. Sep. 11, 2001, vol. 98, No. 19. pp. 10869-10874.

Wani, M. C. et al. "Plant Antitumor Agents: Alkaloids: Synthesis of a Pentacyclic Camptothecin Precursor" Chemical Communications 1970. pp. 404.

Wani, M. C. et al. "Plant Antitumor Agents. IX. The Total Synthesis of dl-Camptothecin" Journal of the American Chemical Society 1972, 94:10, pp. 3631-3632.

Wani, M. C. et al. "Plant Antitumor Agents. 18. Synthesis and Biological Activity of Camptothecin Analogues" J. Med. Chem. 1980, 23, pp. 554-560.

Yu D. et al. "Phosphorylation of DNA Topoisomerase I by the c-Abl Tyrosine Kinase Confers Camptothecin Sensitivity" The Journal of Biological Chemistry vol. 279, No. 50, Issue of Dec. 10, 2004, pp. 51581-51861.

Zhang et al. "Topotecan Inhibits Human Immunodeficiency Virus Type 1 Infection through a Topoisomerase-Independent Mechanism in a Cell Line with Altered Topoisomearse I" Antimicrobial Agents and Chemotherapy, vol. 41, No. 5., May 1997, pp. 977-981.

Cardellini, E et al., "Human Topoisomerase I is Phosphorylated in vitro on its Amino Terminal Domain by Protein Kinase NII." Biol. Chem. Hoppe-Seyler 375:255-259, 1994.

Coderoni, S et al., "Phosphorylation Sites for Type NII Protein Kinase in DNA-Topoisomerase I From Calf Thymus." Int. J. Biochem. 22(7):737-746, 1990.

Sanchez-Perez, I. "DNA repair inhibitors in cancer treatment." Clin Transl Oncol. 8(9):642-646, 2008.

Yu, D et al., "Phosphorylation of DNA Topoisomerase I by the c-Abl Tyrosine Kinase Confers Camptothecin Sensitivity." J Biol Chem. 279(50):51851-51861, 2004.

St-Amant, C. "Altered phosphorylation of topoisomerase I following overexpression in an ovarian cancer cell line." Biochemistry and Cell Biology, 84(1), pp. 55-66 (2006).

Chikamori et al. "Phosphorylation of serine 1106 in the catalytic domain of topoisomerase II alpha regulates enzymatic activity and drug sensitivity." J. of Biological Chemistry, 278(15), pp. 12696-12702, Apr. 11, 2003.

Rasheed et al. "Mechanism of resistance to topoisomerase I-targeting drugs." Oncogene (2003) 22, pp. 7296-7304.

Page 4 of Examination Report dated May 19, 2014 in connection with European Patent Application No. 09726814.8.

\* cited by examiner

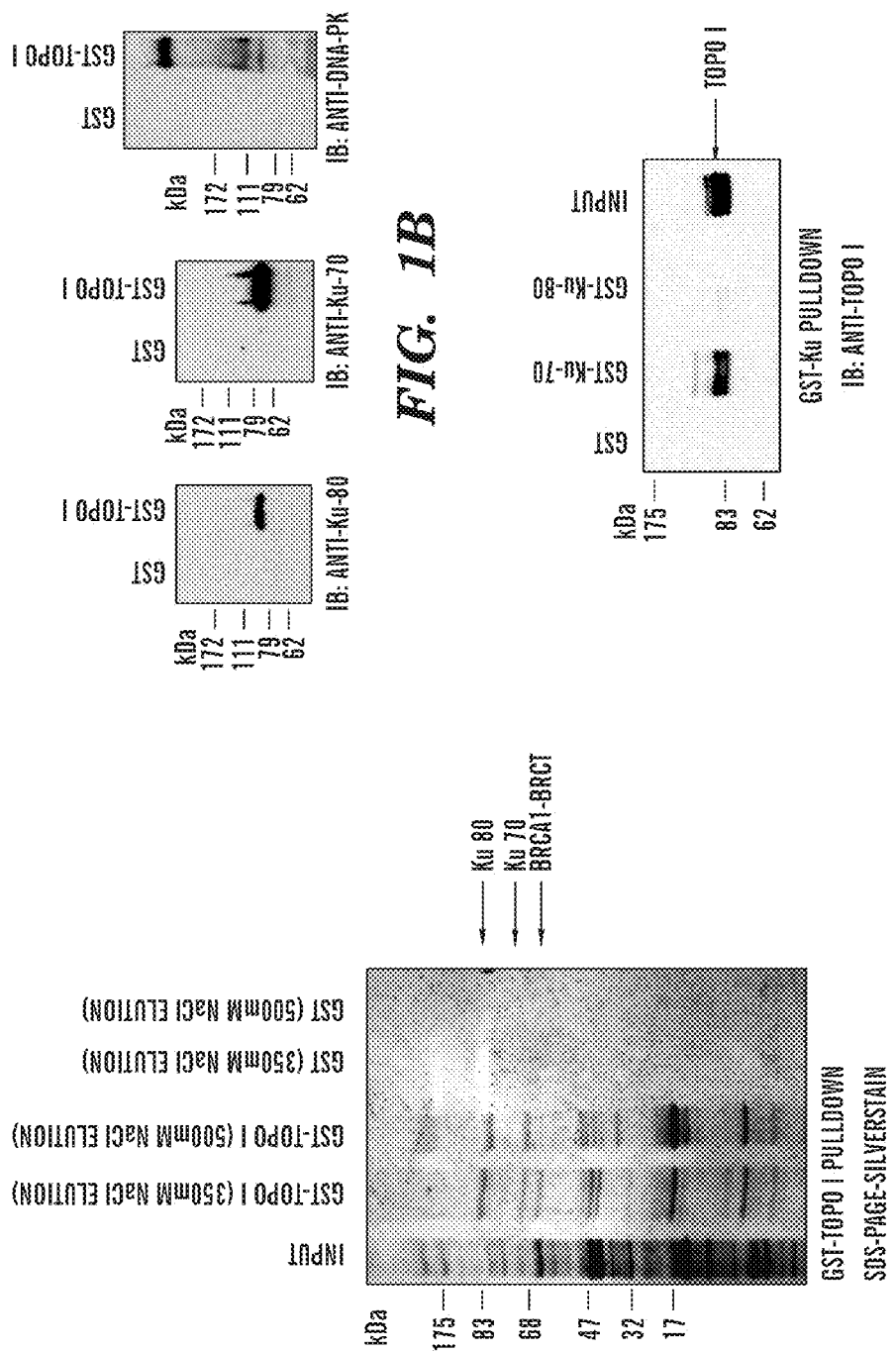

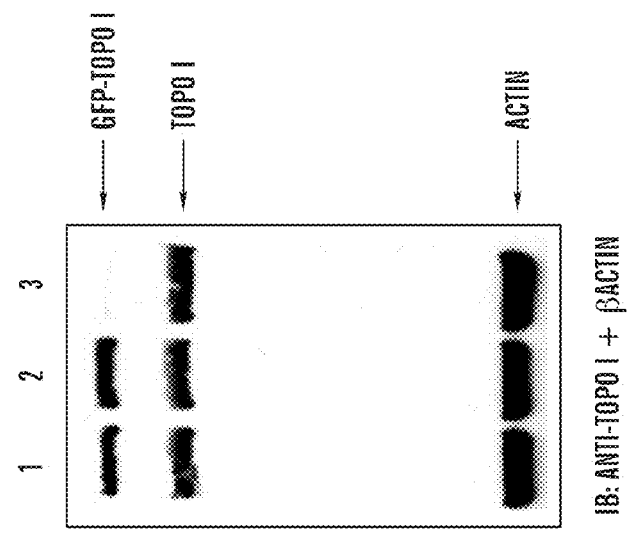
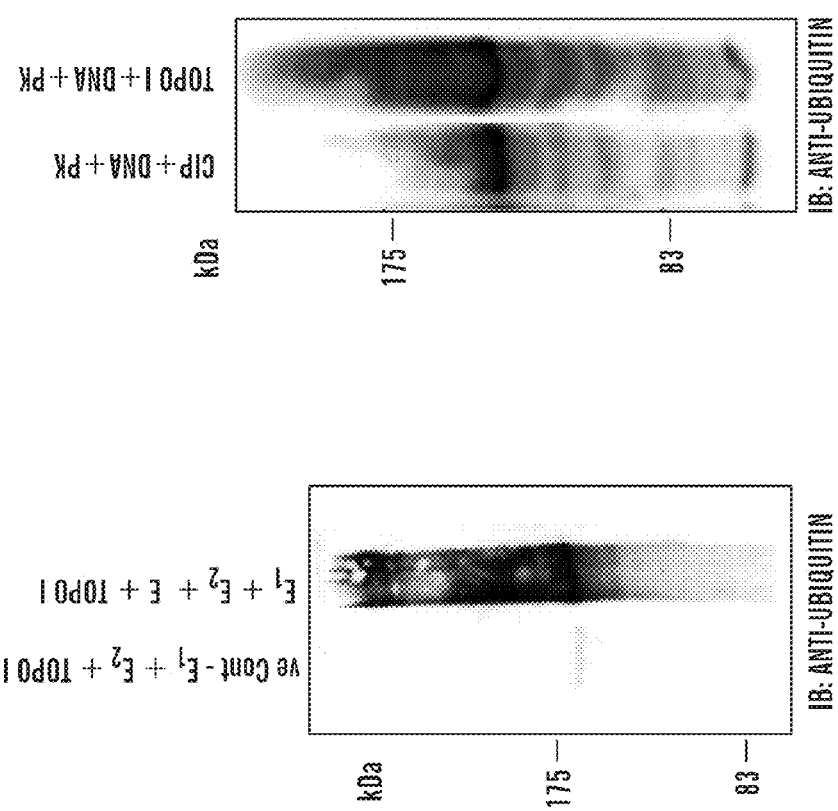
FIG. 4A
FIG. 4B
FIG. 4C

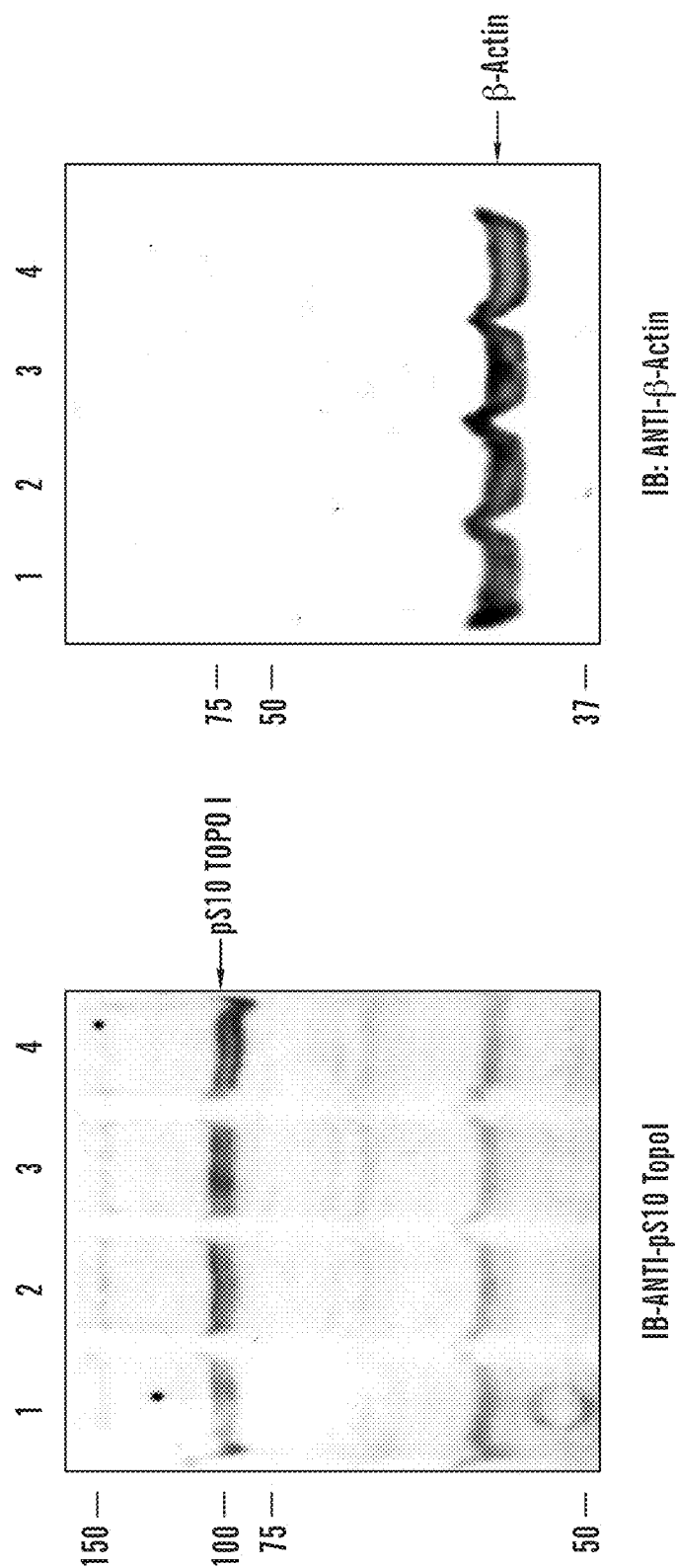

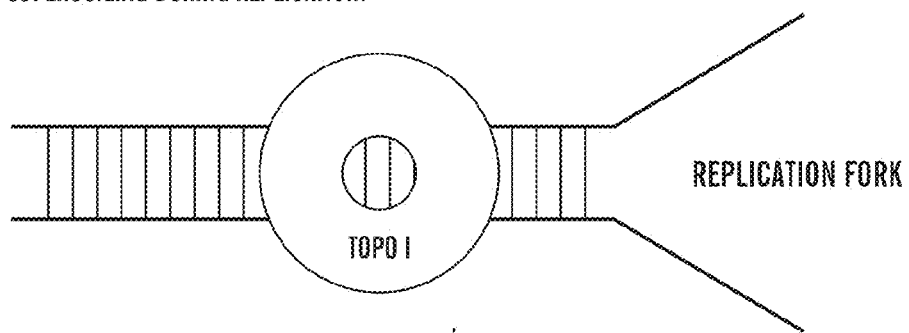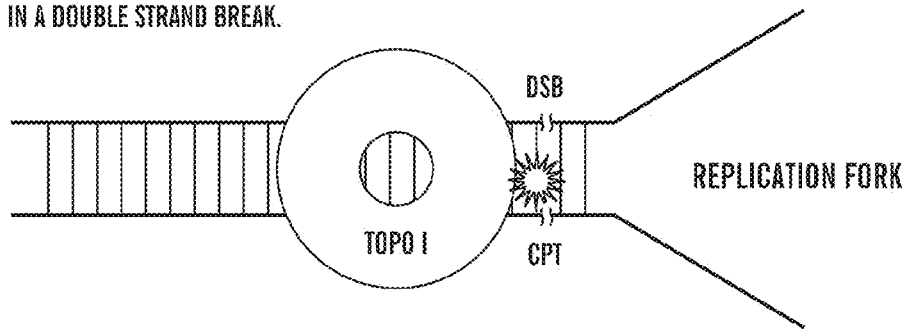
FIG. 11A

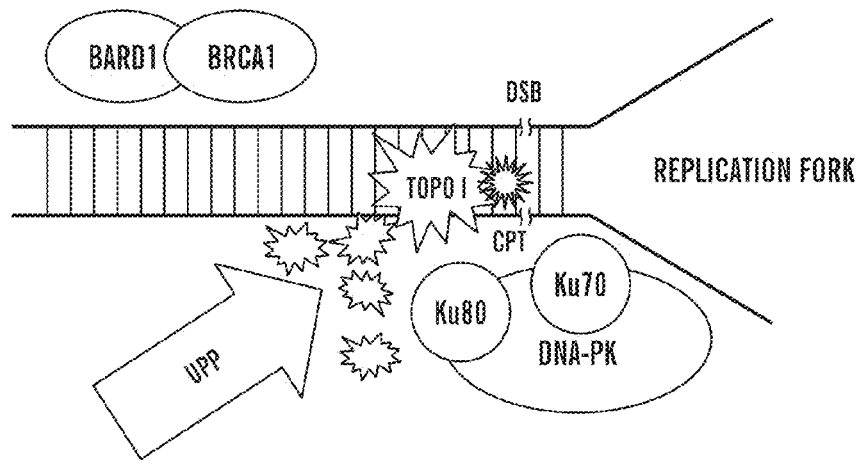
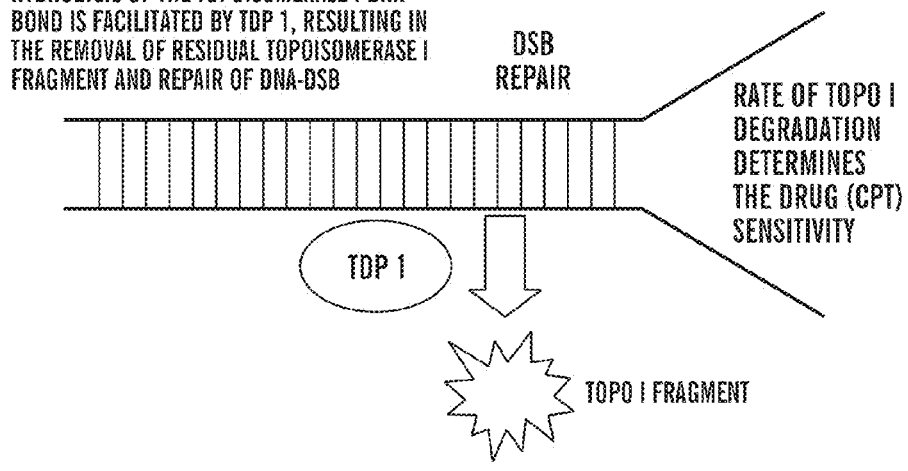
FIG. 11C

SEQUENCE LISTING

```
<160> NUMBER OF SEQ ID NOS: 6

<210> SEQ ID NO 1
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (10)..(10)
<223> OTHER INFORMATION: Phosphorylated-serine

<400> SEQUENCE: 1

Met Ser Gly Asp His Leu His Asn Asp Ser Gln Ile Glu Ala Asp Phe
 1               5                  10                  15

Arg

<210> SEQ ID NO 2
<211> LENGTH: 765
<212> TYPE: PRT
<213> ORGANISM: Homo sapiens

<400> SEQUENCE: 2

Met Ser Gly Asp His Leu His Asn Asp Ser Gln Ile Glu Ala Asp Phe
 1               5                  10                  15

Arg Leu Asn Asp Ser His Lys His Lys Asp Lys His Lys Asp Arg Glu
                20                  25                  30

His Arg His Lys Glu His Lys Lys Glu Lys Asp Arg Glu Lys Ser Lys
            35                  40                  45

His Ser Asn Ser Glu His Lys Asp Ser Glu Lys Lys His Lys Glu Lys
        50                  55                  60

Glu Lys Thr Lys His Lys Asp Gly Ser Ser Glu Lys His Lys Asp Lys
 65                 70                  75                  80

His Lys Asp Arg Asp Lys Glu Lys Arg Lys Glu Glu Lys Val Arg Ala
                85                  90                  95
```

-continued

```
Ser Gly Asp Ala Lys Ile Lys Lys Glu Lys Glu Asn Gly Phe Ser Ser
            100                 105                 110
Pro Pro Gln Ile Lys Asp Glu Pro Glu Asp Gly Tyr Phe Val Pro
            115                 120                 125
Pro Lys Glu Asp Ile Lys Pro Leu Lys Arg Pro Arg Asp Glu Asp
130                 135                 140
Ala Asp Tyr Lys Pro Lys Lys Ile Lys Thr Glu Asp Thr Lys Lys Glu
145                 150                 155                 160
Lys Lys Arg Lys Leu Glu Glu Glu Asp Gly Lys Leu Lys Lys Pro
                165                 170                 175
Lys Asn Lys Asp Lys Asp Lys Lys Val Pro Glu Pro Asp Asn Lys Lys
            180                 185                 190
Lys Lys Pro Lys Lys Glu Glu Gln Lys Trp Lys Trp Trp Glu Glu
            195                 200                 205
Glu Arg Tyr Pro Glu Gly Ile Lys Trp Lys Phe Leu Glu His Lys Gly
            210                 215                 220
Pro Val Phe Ala Pro Pro Tyr Glu Pro Leu Pro Glu Asn Val Lys Phe
225                 230                 235                 240
Tyr Tyr Asp Gly Lys Val Met Lys Leu Ser Pro Lys Ala Glu Glu Val
                245                 250                 255
Ala Thr Phe Phe Ala Lys Met Leu Asp His Glu Tyr Thr Thr Lys Glu
            260                 265                 270
Ile Phe Arg Lys Asn Phe Phe Lys Asp Trp Arg Lys Glu Met Thr Asn
            275                 280                 285
Glu Glu Lys Asn Ile Ile Thr Asn Leu Ser Lys Cys Asp Phe Thr Gln
            290                 295                 300
Met Ser Gln Tyr Phe Lys Ala Gln Thr Glu Ala Arg Lys Gln Met Ser
305                 310                 315                 320
Lys Glu Glu Lys Leu Lys Ile Lys Glu Glu Asn Glu Lys Leu Leu Lys
                325                 330                 335
Glu Tyr Gly Phe Cys Ile Met Asp Asn His Lys Glu Arg Ile Ala Asn
            340                 345                 350
Phe Lys Ile Glu Pro Pro Gly Leu Phe Arg Gly Arg Gly Asn His Pro
            355                 360                 365
Lys Met Gly Met Leu Lys Arg Arg Ile Met Pro Glu Asp Ile Ile Ile
            370                 375                 380
Asn Cys Ser Lys Asp Ala Lys Val Pro Ser Pro Pro Gly His Lys
385                 390                 395                 400
Trp Lys Glu Val Arg His Asp Asn Lys Val Thr Trp Leu Val Ser Trp
                405                 410                 415
Thr Glu Asn Ile Gln Gly Ser Ile Lys Tyr Ile Met Leu Asn Pro Ser
            420                 425                 430
Ser Arg Ile Lys Gly Glu Lys Asp Trp Gln Lys Tyr Glu Thr Ala Arg
            435                 440                 445
Arg Leu Lys Lys Cys Val Asp Lys Ile Arg Asn Gln Tyr Arg Glu Asp
            450                 455                 460
Trp Lys Ser Lys Glu Met Lys Val Arg Gln Arg Ala Val Ala Leu Tyr
465                 470                 475                 480
Phe Ile Asp Lys Leu Ala Leu Arg Ala Gly Asn Glu Lys Glu Glu Gly
                485                 490                 495
Glu Thr Ala Asp Thr Val Gly Cys Cys Ser Leu Arg Val Glu His Ile
            500                 505                 510
```

```
Asn Leu His Pro Glu Leu Asp Gly Gln Glu Tyr Val Glu Phe Asp
            515                 520                 525
Phe Leu Gly Lys Asp Ser Ile Arg Tyr Tyr Asn Lys Val Pro Val Glu
530                 535                 540
Lys Arg Val Phe Lys Asn Leu Gln Leu Phe Met Glu Asn Lys Gln Pro
545                 550                 555                 560
Glu Asp Asp Leu Phe Asp Arg Leu Asn Thr Gly Ile Leu Asn Lys His
                565                 570                 575
Leu Gln Asp Leu Met Glu Gly Leu Thr Ala Lys Val Phe Arg Thr Tyr
            580                 585                 590
Asn Ala Ser Ile Thr Leu Gln Gln Gln Leu Lys Glu Leu Thr Ala Pro
        595                 600                 605
Asp Glu Asn Ile Pro Ala Lys Ile Leu Ser Tyr Asn Arg Ala Asn Arg
    610                 615                 620
Ala Val Ala Ile Leu Cys Asn His Gln Arg Ala Pro Pro Lys Thr Phe
625                 630                 635                 640
Glu Lys Ser Met Met Asn Leu Gln Thr Lys Ile Asp Ala Lys Lys Glu
                645                 650                 655
Gln Leu Ala Asp Ala Arg Arg Asp Leu Lys Ser Ala Lys Ala Asp Ala
            660                 665                 670
Lys Val Met Lys Asp Ala Lys Thr Lys Lys Val Val Glu Ser Lys Lys
        675                 680                 685
Lys Ala Val Gln Arg Leu Glu Glu Leu Met Lys Leu Glu Val Gln
    690                 695                 700
Ala Thr Asp Arg Glu Glu Asn Lys Gln Ile Ala Leu Gly Thr Ser Lys
705                 710                 715                 720
Leu Asn Tyr Leu Asp Pro Arg Ile Thr Val Ala Trp Cys Lys Lys Trp
                725                 730                 735
Gly Val Pro Ile Glu Lys Ile Tyr Asn Lys Thr Gln Arg Glu Lys Phe
            740                 745                 750
Ala Trp Ala Ile Asp Met Ala Asp Glu Asp Tyr Glu Phe
        755                 760                 765

<210> SEQ ID NO 3
<211> LENGTH: 3734
<212> TYPE: DNA
<213> ORGANISM: Homo sapiens

<400> SEQUENCE: 3
caaatgcgaa cttaggctgt tacacaactg ctggggtctg ttctcgccgc ccgcccggca    60
gtcaggcagc gtcgccgccg tggtagcagc ctcagccgtt tctggagtct cgggcccaca   120
gtcaccgccg cttacctgcg cctcctcgag cctccggagt ccccgtccgc ccgcacaggc   180
cggttcgccg tctgcgtctc ccccacgccg cctcgcctgc cgccgcgctc gtccctccgg   240
gccgacatga gtgggaccac cctccacaac gattcccaga tcgaagcgga tttccgattg   300
aatgattctc ataaacacaa agataaacac aaagatcgag aacaccggca caaagaacac   360
aagaaggaga aggaccggga aaagtccaag catagcaaca gtgaacataa agattctgaa   420
aagaaacaca agagaaggag gaagaccaaa cacaaagatg gaagctcaga aaagcataaa   480
gacaaacata agacagagaa caaggaaaaa cgaaaagagg aaaaggttcg agcctctggg   540
gatgcaaaaa taagaaggaa gaaggaaaat ggcttctcta gtccaccaca aattaaagat   600
gaacctgaag atgatggcta ttttgttcct cctaagagg atataaagcc attaaagaga   660
cctcgagatg aggatgatgc tgattataaa cctaagaaaa ttaaaacaga agataccaag   720
```

```
aaggagaaga aaagaaaact agaagaagaa gaggatggta aattgaaaaa acccaagaat      780
aaagataaag ataaaaaagt tcctgagcca gataacaaga aaaagaagcc gaagaaagaa      840
gaggaacaga agtggaaatg gtgggaagaa gagcgctatc ctgaaggcat caagtggaaa      900
ttcctagaac ataaaggtcc agtatttgcc ccaccatatg agcctcttcc agagaatgtc      960 aagtttatt atgatggtaa agtcatgaag ctgagcccca agcagagga agtagctacg       1020 ttctttgcaa aaatgctcga ccatgaatat actaccaagg aaatatttag gaaaaatttc     1080
tttaaagact ggagaaagga aatgactaat gaagagaaga atattatcac caacctaagc    1140
aaatgtgatt ttacccagat gagccagtat ttcaaagccc agacggaagc tcggaaacag    1200
atgagcaagg aagagaaact gaaaatcaaa gaggagaatg aaaaattact gaaagaatat    1260
ggattctgta ttatggataa ccacaaagag aggattgcta acttcaagat agagcctcct    1320
ggacttttcc gtggccgcgg caaccacccc aagatgggca tgctgaagag acgaatcatg    1380
cccgaggata taatcatcaa ctgtagcaaa gatgccaagg ttccttctcc tcctccagga    1440
cataagtgga agaagtccg gcatgataac aaggttactt ggctggtttc ctggacagag     1500
aacatccaag gttccattaa atacatcatg cttaaccta gttcacgaat caagggtgag     1560
aaggactggc agaaatacga gactgctcgg cggctgaaaa aatgtgtgga caagatccgg    1620
aaccagtatc gagaagactg gaagtccaaa gagatgaaag tccggcagag agctgtagcc    1680
ctgtacttca tcgacaagct tgctctgaga gcaggcaatg aaaaggagga aggagaaaca    1740
gcggacactg tgggctgctg ctcacttcgt gtggagcaca tcaatctaca cccagagttg    1800
gatggtcagg aatatgtggt agagtttgac ttcctcggga aggactccat cagatactat    1860
aacaaggtcc ctgttgagaa acgagttttt aagaacctac aactatttat ggagaacaag    1920
cagcccgagg atgatctttt tgatagactc aatactggta ttctgaataa gcatcttcag    1980
gatctcatgg agggcttgac agccaaggta ttccgtacat acaatgcctc catcacgcta    2040
cagcagcagc taaaagaact gacagccccg gatgagaaca tcccagcgaa gatcctttct    2100
tataaccgtg ccaatcgagc tgttgcaatt ctttgtaacc atcagagggc accaccaaaa    2160
acttttgaga agtctatgat gaacttgcaa actaagattg atgccaagaa ggaacagcta    2220
gcagatgccc ggagagacct gaaaagtgct aaggctgatg ccaaggtcat gaaggatgca    2280
aagacgaaga aggtagtaga gtcaaagaag aaggctgttc agagactgga ggaacagttg    2340
atgaagctgg aagttcaagc cacagaccga gaggaaaata aacagattgc cctgggaacc    2400
tccaaactca attatctgga ccctaggatc acagtggctt ggtgcaagaa gtggggtgtc    2460
ccaattgaga agatttacaa caaaacccag cgggagaagt ttgcctgggc cattgacatg    2520
gctgatgaag actatgagtt ttagccagtc tcaagaggca gagttctgtg aagaggaaca    2580
gtgtggtttg ggaaagatgg ataaactgag cctcacttgc cctcgtgcct ggggagaga     2640 ggcagcaagt cttaacaaac caacatcttt gcgaaaagat aaacctggag atattataag    2700
ggagagctga gccagttgtc ctatggacaa cttatttaaa aatatttcag atatcaaaat    2760
tctagctgta tgatttgttt tgaattttgt ttttatttc aagagggcaa gtggatggga     2820
atttgtcagc gttctaccag gcaaattcac tgtttcactg aaatgtttgg attctcttag    2880
ctactgtatg caaagtccga ttatattggt gcgttttac agttagggtt ttgcaataac     2940
ttctatattt taatagaaat aaattcctaa actcccttcc ctctctccca tttcaggaat    3000
ttaaaattaa gtagaacaaa aaacccagcg cacctgttag agtcgtcact ctctattgtc    3060
```

-continued

```
atggggatca attttcatta aacttgaagc agtcgtggct ttggcagtgt tttggttcag    3120
acacctgttc acagaaaaag catgatggga aaatatttcc tgacttgagt gttccttttt    3180
aaatgtgaat ttttatttct ttttaattat tttaaaatat ttaaacctttt ttcttgatct   3240 taaagatcgt gtagattggg gttggggagg gatgaagggc gagtgaatct aaggataatg    3300
aaataatcag tgactgaaac cattttccca tcatcctttg ttctgagcat tcgctgtacc    3360
ctttaagata tccatctttt tcttttttaac cctaatcttt cacttgaaag attttattgt   3420
ataaaaagtt tcacaggtca ataaacttag aggaaaatga gtatttggtc caaaaaaagg    3480
aaaaataatc aagattttag ggcttttatt ttttcttttg taattgtgta aaaaatggaa    3540
aaaaacataa aaagcagaat tttaatgtga agacattttt tgctataatc attagttta    3600 gaggcattgt tagtttagtg tgtgtgcaga gtccatttcc cacatctttc ctcaagtatc    3660
ttctattttt atcatgaatt cccttttaat caactgtagg ttatttaaaa taaattccta    3720
caacttaatg gaaa                                                      3734

<210> SEQ ID NO 4
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: Phosphorylated-serine

<400> SEQUENCE: 4

Asn Asp Ser Gln Ile Glu Ala Asp Phe Arg Leu Asn Asp Cys
1               5                  10

<210> SEQ ID NO 5
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Gly Gly Gly Gly Cys
1               5

<210> SEQ ID NO 6
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (11)..(11)
<223> OTHER INFORMATION: Phosphorylated-serine

<400> SEQUENCE: 6

Asp Met Ser Gly Asp His Leu His Asn Asp Ser Gln Ile Glu Ala Asp
1               5                   10                  15

Phe Arg
```

US 8,993,309 B2

PREDICTIVE MARKER FOR TOPOISOMERASE I INHIBITORS

CROSS REFERENCE TO RELATED APPLICATIONS

This application is a National Phase Entry Application under 35 U.S.C. §371 of co-pending International Application PCT/US2009/038981, filed 31 Mar. 2009, which claims benefit under 35 U.S.C. 119(e) of U.S. Provisional Patent Application Ser. No. 61/072,490 filed Mar. 31, 2008, the contents of which are incorporated herein by reference in their entirety.

FIELD OF THE INVENTION

The present invention relates generally to the fields of cancer therapy and cancer prevention. More particularly, the present invention generally relates to a diagnostic marker for predicting the efficacy of topoisomerase I (topo I) inhibitors in the treatment of cancers, and the level of sensitivity or resistance of a biological sample to topoisomerase I inhibitors.

BACKGROUND OF THE INVENTION

One of the main problems associated with cancer chemotherapy is that individual subjects with the same histology do not respond identically to a given agent or a given therapeutic protocol. The response range may vary in large proportions, even in chemosensitive tumors such as breast cancer. A number of determinants of drug sensitivity are well known, such as drug dose, drug combinations and schedule of administration, subject age and status, tumor localization etc, but the intrinsic sensitivity of a given tumor is a major factor in which remains difficult to evaluate.

One strategy to improve the effectiveness of treatment has been to individualize drug treatment as a function of the sensitivity of tumor cells. Methods to predict how effective a drug may be in a subject are typically based on in vitro or ex vivo testing of the tumor cells (taken during a biopsy) to a battery of drugs and chemotherapy agents. Such strategies have several limitations; they are often poor predictors of chemosensitivity in vivo, they are time-consuming, and both manually and cost expensive. The identification of novel cancer subtypes promises to provide more specific, more effective and less toxic therapies. This tumor subset is refractory to commonly used chemotherapeutic agents and therefore is associated with a poor prognosis (Sorlie, et al., 2001, Proc Natl Acad Sci U S A 98:10869). To date little progress has been made in identifying specific molecular pathways associated with these refractory cancers that may be effectively targeted for therapeutic purposes.

Human topoisomerase I (topoI) is an essential and ubiquitous enzyme that is involved in various DNA transactions. The identification of topoI as the target of a new class of anti-neoplastic drug (camptothecin, also referred herein as "CPT") has led to the rapid development of topoI structure-function in the context of cancer therapy. Two CPT analogues, topotecan and irinotecan, are currently used in clinics for small cell lung cancer (SCLC), colon and ovarian cancer and in several refractory cancers, including breast and cervical. However, like most cancer drugs, not all patients respond, in this case only about 30% of patients respond to topoI inhibitors. The topoI protein level is high in most solid tumors, and thus topoI levels can not be used as a predictive marker. Additionally, although topoI is the specific target of CPT, the expression profile of topoI does not provide prognostic index. Based on the preclinical studies, it is likely that clinical resistance to these drugs might be the result of (1) inadequate accumulation of the drug in the tumor, or (2) post-translational modification of topoI. It has been demonstrated that topoI is ubiquitinated and degraded in cells in the response to CPT by ubiquitin proteosomal pathway (UPP). Importantly, the rate of UPP mediated degradation varies in different cancer cells and is correlated to the CPT sensitivity. However the mechanism of ubiquitination dependent proteosomal degradation of topoI in the response to CPT is not understood.

There is a significant need in the art for a satisfactory treatment of tumor subsets refectory or non-responsive to commonly used chemotherapeutic agents, (specifically in epithelial cell cancers such as breast, lung, ovarian, brain, colon and prostate cancers), which overcomes the non-responsiveness exhibited by subjects. Such a treatment could have a dramatic impact on the health of individuals, especially older individuals, among whom cancer is especially common, and females whom have a high incidence of breast cancer.

SUMMARY OF THE INVENTION

The present invention generally relates to a diagnostic marker for predicting the efficacy of topoisomerase I (topo I) inhibitors in the treatment of cancers. In particular, one aspect of the present invention relates to methods to determine effectiveness of topoisomerase I (topo I) inhibitors in the treatment of cancer. Specifically, the inventors have discovered herein that topoI is phosphorylated at S10 by DNA-PK and results in its ubiquitination by BRAC1/BARD1 heterodimer and its subsequent degradation. The inventors have discovered that the presence of phosphorylation of topoI, in particular the phosphorylation of topoI on serine 10 (S10) indicates rapid topoI degradation and resistance to topo I inhibitors such as camptothecin (CPT), or CTP analogues such as topotecan and irinotecan and derivatives thereof. Accordingly, one aspect of the present invention relates to detection of phosphorylation of topoI on serine 10, i.e. the detection of phospho-topoI-S10 in a biological sample from a subject with cancer, as a prognostic determinant for drug efficacy with topo I inhibitors such as CTP and its analogues.

One aspect of the present invention relates to methods and compositions to determine if a topoisomerase I inhibitor is effective in a subject with cancer. One aspect of the present invention relates to a method to determine the presence of phosphorylation of topo I polypeptide, wherein the presence of phosphorylation of a topo I polypeptide indicates that the subject having such cancer will likely be nonresponsive (or unresponsive) to a topo I inhibitor as compared to a subject with a cancer comprising a non-phosphorylated topo I polypeptide. In one embodiment of this aspect and all other aspects disclosed herein, the phosphorylation is phosphorylation of a serine residue of a topo I polypeptide, wherein the presence of phosphorylation of a serine residue of the topo I polypeptide identifies that the cancer will likely be nonresponsive (or unresponsive) to a topo I inhibitor. In another embodiment of this aspect and all other aspects disclosed herein, the phosphorylation is phosphorylation of the serine 10 (S10) residue of a topo I polypeptide, wherein the presence of phosphorylation of the serine 10 reside (S10) of the topo I polypeptide indicates that a subject with a cancer will likely be nonresponsive (or unresponsive) to a topo I inhibitor as compared to a subject where the corresponding residue is not phosphorylated. Another embodiment of this aspect and all other aspects disclosed herein, detection of lack of phosphorylation of the topoisomerase I polypeptide, in particular the lack of phosphorylation of a topo I polypeptide on serine 10 (S10) indicates such a cancer is likely to be responsive to a topo I inhibitor.

In some embodiments, one presence of phosphorylation of the serine 10 reside (S10) of the topo I polypeptide indicates that a subject with a cancer will likely be nonresponsive (or unresponsive) to a topo I inhibitor as compared to a subject where the corresponding residue is not phosphorylated. One aspect of the invention relates to grading the level of phosphorylation of S10 topo I polypeptide in a subject. For example, the level of phospho-S10 topo I polypeptide as compared to non-phospho S10 topo I polypeptide can be categorized or graded on 4 levels, where, for example, level 1 is about a 0% level phospho-S10 topo I polypeptide and indicates a subject is likely to be fully responsive to a topo I inhibitor, level 2 is about a 10-25% level phospho-S10 topo I polypeptide and indicates a subject is likely to be partially responsive to a topo I inhibitor; level 3 is a 25-50% level of level phospho-S10 topo I polypeptide and indicates a subject is likely to be unresponsive to a topo I inhibitor, and level 4 is any level of level phospho-S10 topo I polypeptide above 50%, for example at least 50%, or at least about 60% or at least about 70% or at least about 80% or at least about 90% or at least about 100% indicates a subject is likely to be completely non-responsive to a topo I inhibitor. Stated another way, a subjects' likelihood of being responsive to a topo I inhibitor can be graded on the degree of phospho-S10 topo I polypeptide as compared to degree of non-phospho S10 topo I polypeptide, which can be graded on 4 levels; grades 1 (0-10%), 2 (10-25%), 3 (25-50%) or 4 (>50%), where level 1 indicates a subject is likely to be responsive to a topo I inhibitor, where level 2 indicates a subject is likely to be partially responsive (i.e. about 50% or less responsive) to a topo I inhibitor as compared to level 1, where level 3 indicates a subject is likely to be unresponsive to a topo I inhibitor as compared to a subject classified as level 1 (i.e. a subject will likely have about 10% or less efficacy of a topo I inhibitor), and where level 4 indicates a subject is likely to be completely unresponsive to a topo I inhibitor as compared to a subject classified as a level 1 (i.e. a subject will likely have about 5% or about a 2% or less efficacy of a topo I inhibitor). In other embodiments, more than 4 levels of classification can be used, for example, at least 5, or at least 6, or at least 7, or at least 8 or at least 9 levels or more than 9 different classification levels can be used.

In some embodiments, if a subject is identified as being above a certain pre-defined threshold level the subject is likely to be identified to be unresponsive to a topo I inhibitor. In some embodiments, a pre-defined threshold level is about level 3, wherein the % of phospho-S10 topo I polypeptide (from the total topo I polypeptide) is about 25% or above, a subject is likely to be unresponsive to a topo I inhibitor as compared to a subject with a threshold level below 3 (i.e. less than 25%). Accordingly, in some embodiments, a pre-defined threshold level to identify if a subject is unresponsive to a topo I inhibitor is a 25% or greater, wherein a subject having a % of phospho-S10 topo I inhibitor to total topo I polypeptide of 25% or greater (i.e. about at least 30% or at least about 40% or a least about 50% or at least about 60% or more) is identified as being unresponsive to a topo I inhibitor, whereas a subject having a % of phospho-S10 topo I inhibitor to total topo I polypeptide of less than 25% (i.e. about 20% or about 10% or about 5% or about 2% or less) is identified as being responsive, or partially responsive to a topo I inhibitor.

Another aspect of the present invention relates to a method to treat cancer in a subject, the method comprising measuring the level of phosphorylation of a topoisomerase I polypeptide in a biological subject comprising cancer cells from a subject; and detecting the level of phosphorylation of the topo I polypeptide, in particular detecting the level of phosphorylation at serine 10 (S10) of the topo I polypeptide, and if the topo I polypeptide is phosphorylated, for example at residue S10, the cancer is identified as being unresponsive to a topoisomerase I inhibitor. The cancer cells in one embodiment are taken from a subject and tested using the methods, kits, machines and computer systems and computer readable media as described herein.

A subject identified as being likely to be responsive to a topoisomerase I inhibitor can be treated with a therapeutically effective amount of a topo I inhibitor, such as, but not limited to CPT, or analogues thereof such as topotecan and irinotecan, either alone or in combination with other therapeutic and/or anti-cancer drugs.

In some embodiments, a topo I inhibitor is a chemotherapy agent, for example but not limited to CPT, or analogues thereof such as topotecan and irinotecan and derivatives as these terms are defined herein. Another aspect of the present invention provides to methods for treating and/or preventing a subject affected with or at risk of developing cancer, the method comprising determining the presence of phosphorylation of a topo I polypeptide (phospho-topo I), and in particular embodiments, the method comprises determining the presence of phosphorylation at serine 10 (S10) residue of a topoI polypeptide (phosphor-S10-topo I). In other embodiments, the methods, kits, machines, computer systems and computer readable media are used to determine the phosphorylation status of a topo I polypeptide in a biological sample, in particular the presence of phospho-topo I, and more specifically, the presence of phospho-S10-topo I polypeptide in a biological sample.

In one embodiment, any means known to a skilled artisan can be used to determine the phosphorylation status of topo I polypeptide, and in particular the presence of phospho-S10 topo I polypeptide in a cancer in a subject. Accordingly, the present invention encompasses use of any in vivo detection method, any ex vivo detection method or any in vitro detection method to determine the phosphorylation status of topo I polypeptide, and in particular the presence of phospho-S10 topo I polypeptide in subject with cancer. In some embodiments, the method is a high throughput automated immunohistochemistry method commonly known by a one of ordinary skill in the art. In another embodiment, in vivo detection method can determine the phosphorylation status of topo I polypeptide, in particular the presence of a phospho-S10 topo I polypeptide in a cancer present in a subject, by administering to the subject for example but not limited to, labeled antibodies such as anti-phospho-S10 topo I antibodies to the subject, including for example radiolabeled, or fluorescence-labeled, or bioluminescence-labeled such as luciferase anti-phospho-S10 topo I antibodies or alternatively radiolabeled nucleotides and using a detection module, for example an in vivo imaging camera or machine, such as a MRI, CAT scan or other in vivo imaging machines to determine the presence of the anti-phospho-S10 topo I antibodies in the subject, where in one embodiment, the output data from the detection module is analyzed using a computer system or computer readable media as disclosed herein, or in an alternative embodiment, the output data of the detection module is received by the storage module which is connected to the comparison module of a machine as described herein.

In another embodiment, the phosphorylation status of topo I polypeptide such as the presence of a phospho-S10 topo I polypeptide can be determined in a biological sample taken from a subject, where a biological sample is placed into a detection module which determines the phosphorylation status of topo I polypeptide, such as presence of a phospho-S10 topo I polypeptide in the biological sample, where the output data of the detection module is received by the storage module which is connected to the comparison module of a machine as described herein, or in an alternative embodiment, the output data of the detection module is analyzed by the computer system and computer readable media as disclosed herein.

In some embodiments, a subject identified to be unresponsive to a topo I inhibitor by the methods, kits, machines, computer systems and computer readable media as disclosed herein is administered a pharmaceutical composition comprising a chemotherapeutic agent other than a topo I inhibitor. In an alternative embodiment, a subject can be administered a topo I inhibitor and an agent which increases the sensitivity of the subject to a topo I inhibitor (herein referred to as a "topo I inhibitor sensitivity agent"), where a topo I inhibitor sensitivity agent can increase the dephosphorylation of a topo I polypeptide, in particular, increase the dephosphorylation of serine 10 (S10) of the topo I polypeptide. In another embodiment, a topo I inhibitor sensitivity agent can be an antagonist which inhibits the phosphorylation of topo I polypeptide, such as for example but not limited to, an anti-phospho-S10 topo I antibody or an antagonist or inhibitor of DNA-PK such as, but not limited to NU7026 also known as 2-morpholin-4-yl)-benzo[h]chromen-4-one, and derivatives and analogues thereof. Accordingly, one aspect of the invention relates to co-administering a topo I inhibitor substantially simultaneously with a topo I inhibitor sensitivity agent to a subject identified to be unresponsive to a topo I inhibitor. In some embodiments, such a pharmaceutical composition comprising a topo I inhibitor can be administered alone or substantially at the same time, before or after the administration of a pharmaceutical composition comprising an agent which increases the sensitivity of the subject to a topo I inhibitor (i.e. a topo I inhibitor sensitivity agent such as an agent which increases the dephosphorylation of S10 on the topo I polypeptide and/or an agent which inhibits topo I phosphorylation on S10, such as an anti-phospho-S10 topo I antibody or an antagonist of DNA-PK).

One aspect of the present invention and all other aspect described herein, a machine can be used to determine phosphorylation status of topo I polypeptides in a biological sample, for example, a machine for obtaining data regarding a biological sample from a subject comprising: a biological sample container to hold the biological sample; a determination module configured to detect the presence of phosphorylation of a topoisomerase I polypeptide, for example the detection of phospho-S10 topo I in the biological sample which produces output data, in some embodiments the output data in a computer readable media format; a storage device configured to store the output data from the determination module; a comparison module adapted to compare the output data from the determination module with data stored on the storage device, such as stored reference data and control data, and a display module for displaying a page of retrieved content for the user on a client computer, wherein the retrieved content comprises any one or a combination of the following; (i) the presence or absence of phosphorylation of the topoisomerase I polypeptide, for example the retrieved content is the presence or absence of phospho-S10 topo I; (ii) the absence of phosphorylation of topoisomerase I, for example the absence of phospho-S10 topo I, (iii) the presence of phosphorylation of topoisomerase I, such as the presence of phospho-S10 topo I polypeptide, (iv) a positive test result (i.e. a positive phosphorylation status such as positive S10 topo I phosphorylation status) which indicates that the subject is likely to be more unresponsive to a topoI inhibitor than a subject having a cancer with a negative phosphorylation status, (v) a negative test result (i.e. a negative phosphorylation status such a negative S10 topo I phosphorylation status) which indicates that the subject is likely to be more responsive to a topoI inhibitor than a subject having a cancer with a positive phosphorylation.

One aspect of the present invention is a computer system that can be used to determine if a subject is responsive to a topo I inhibitor. In such an embodiment, a computer system is connected to a determination module and is configured to obtain output data from a determination module regarding a biological specimen, where a determination module is configured to detect the presence of phosphorylation of a topoisomerase I polypeptide, for example the presence of phospho-S10 topo I polypeptide within a subject or in a biological sample obtained from the subject; and where the computer system comprises (a) a storage device configured to store data output from the determination module as well as reference data; where the storage device is connected to (b) a comparison module which in one embodiment, is adapted to compare the output data stored on the storage device with stored reference data, and in alternative embodiments, adapted to compare the output data with itself, where the comparison module produces report data and is connected to (c) a display module for displaying a page of retrieved content (i.e. report data from the comparison module) for the user on a client computer, wherein the retrieved content comprises any one or a combination of the following; (i) the presence or absence of phosphorylation of the topoisomerase I polypeptide, for example the retrieved content is the presence or absence of phospho-S10 topo I; (ii) the absence of phosphorylation of topoisomerase I, for example the absence of phospho-S10 topo I, (iii) the presence of phosphorylation of topoisomerase I, such as the presence of phospho-S10 topo I polypeptide, (iv) a positive test result (i.e. a positive phosphorylation status such as positive S10 topo I phosphorylation status) which indicates that the subject is likely to be more unresponsive to a topoI inhibitor than a subject having a cancer with a negative phosphorylation status, (v) a negative test result (i.e. a negative phosphorylation status such a negative S10 topo I phosphorylation status) which indicates that the subject is likely to be more responsive to a topoI inhibitor than a subject having a cancer with a positive phosphorylation.

In some embodiments the comparison module compares the output data stored on the storage device with itself or stored reference data, and calculates a positive S10 topo I phosphorylation status (i.e. the presence of phospho-S10 topo I polypeptide) which indicates a positive test result and generates report data to indicate that the subject is likely to be more unresponsive to a topoI inhibitor than a subject having a cancer with a negative phosphorylation status, where the report data from the comparison module is retrieved from the display module and displayed on the display module.

One aspect of the present invention and all other aspect described herein, one can use a computer readable media to determine phosphorylation status of topo I polypeptides from a subject having or at risk of having cancer, for example, a computer readable media having computer readable instructions recorded thereon to define software modules including a determination module and a comparison module for implementing a method on a computer, said method comprising: a storage device configured to store data reference data and output data from a determination module which has measured the presence or absence of the phosphorylation of topo I polypeptide, such as the presence or absence of phospho-S10 topo I polypeptide; a comparison module which generates report data, where the comparison module is adapted to compare the data stored on the storage device, for example a comparison of output data from the determination module with itself or alternatively with reference data, and a display module for displaying a page of retrieved content which is the report data from the comparison module for the user on a client computer, wherein the retrieved content comprises any one or a combination of the following; (i) the presence or absence of phosphorylation of the topoisomerase I polypeptide, for example the retrieved content is the presence or absence of phospho-S10 topo I; (ii) the absence of phosphorylation of topoisomerase I, for example the absence of phospho-S10 topo I, (iii) the presence of phosphorylation of topoisomerase I, such as the presence of phospho-S10 topo I polypeptide, (iv) a positive test result (i.e. a positive phosphorylation status such as positive S10 topo I phosphorylation status) which indicates that the subject is likely to be more unresponsive to a topoI inhibitor than a subject having a cancer with a negative phosphorylation status, (v) a negative test result (i.e. a negative phosphorylation status such a negative S10 topo I phosphorylation status) which indicates that the subject is likely to be more responsive to a topoI inhibitor than a subject having a cancer with a positive phosphorylation.

Another aspect of the present invention also relates to a method to identifying the likelihood of a cancer to be unresponsive to a topoisomerase I inhibitor, the method comprising measuring the level of phosphorylation of topoisomerase I polypeptide in at least one cancer cell, wherein the presence of phosphorylation identifies the cancer as being more likely to be unresponsive to a topoisomerase inhibitor as compared to a cancer wherein the absence of phosphorylation of topoisomerase I is detected.

Another aspect of the present invention relates to a method for treating cancer in a subject, the methods comprising: (i) measuring the level of phosphorylation of topoisomerase I polypeptide in a biological sample comprising cancer cells obtained from the subject; (ii) detecting the level of topoisomerase I polypeptide, wherein if the topoisomerase I polypeptide is phosphorylated the cancer is identified as being unresponsive to a topoisomerase I inhibitor, or wherein if the topoisomerase I polypeptide is not phosphorylated the cancer is identified as being likely to be responsive to a topoisomerase I inhibitor; (iii) administering to a subject an anti-cancer agent other than a topoisomerase I inhibitor where the cancer is identified as being unresponsive to a topoisomerase I inhibitor.

In some embodiments, a topo I inhibitor is an antagonist of a topo I polypeptide of SEQ ID NO: 2 or a variant thereof, where an antagonist of a topo I polypeptide is any agent commonly known by one of ordinary skill in the art that inhibits the gene expression and/or the biological activity of a topo I polypeptide, and includes for example, but are not limited to agents such as antibodies, antibody fragments, small molecules, peptides, proteins, antisense nucleic acids, ribosomes, PNA, siRNA, oligonucleotides, aptamer, and peptide aptamer and derivatives and fragments thereof. In some embodiments, an antagonist of a topo I polypeptide useful in the methods of the present invention can be a nucleic acid-based inhibitor, nucleic acid construct, a peptide-based inhibitor or a small molecule inhibitor of topo I polypeptide or a polynucleotide encoding the same. In some embodiments a nucleic-acid inhibitor may be a RNAi (RNA interference) agent, such as for example a siRNA molecule or an antisense construct. Exemplary topo I inhibitors are disclosed herein, and include but are not limited to CPT, or analogues thereof such as topotecan and irinotecan. It is encompassed that the present invention provides methods, kits, machines, computer systems and computer readable media for determining if a subject is responsive to a topo I inhibitor regardless what the topo inhibitor is being used for. In some embodiments, the topo I inhibitor is being used as an anti-cancer treatment, including therapeutic and prophylactic anti-cancer treatment, however, a topo I inhibitor can be used for the treatment of non-cancer diseases or disorders where use of a topo I inhibitor is desired, for example any treatment strategy where cell death is the desired outcome.

Another aspect of the present invention provides an isolated anti-phospho-S10 topo I antibody which binds with specific affinity to the phosphorylated serine residue of SEQ ID NO: 1 or phosphorylated serine residue on SEQ ID NO: 4, or to serine 10 (S10) of the polypeptide of the amino acid sequence of SEQ ID NO: 2.

Another aspect of the present invention relates to methods for increasing the sensitivity of a subject or a cancer, or cancer cell to a topo I inhibitor, the method comprising administering to the subject or a cancer cell a combination of an effective amount of an a topo I inhibitor and an effective amount a topo I inhibitor sensitivity agent (i.e. an agent which increases the sensitivity of a cancer cell to a topo I inhibitor), where a topo I inhibitor sensitivity agent can include for example, but is not limited to, an agent which increases the dephosphorylation of S10 of the topo I polypeptide and/or an agent which inhibits topo I phosphorylation on S10, such as an anti-phospho-S10 topo I antibody or an antagonist of DNA-PK.

In some embodiments, the disclosed methods, kits, machines, computer systems and computer readable media are useful for determining if a subject is likely to be responsive to a topo I inhibitor, and where a topo I inhibitor is used in the treatment of cancer, the present invention is useful in the prevention and/or treatment of cancers such as, but are not limited to, tumors can be selected from a group of cancers consisting of: SCLC cancer, colon cancer, ovarian cancer, or a refractory cancer, for example, breast cancer or cervical cancer. In other embodiments, a cancer useful to be treated in the methods as disclosed herein is any cancer which can be treated, or is desirable to be treated with a topo I inhibitor and can be selected from any cancer in the group consisting of: gastrointestinal cancer, gastric cancer, squamous cell carcinomas (SCC), head and neck cancer, lung cancer, non-small cell lung cancer (NSCLC) and small-cell lung cancer (SCLC), lymphoma, sarcoma, primary and metastic melanoma, thymoma, non-Hodgkin's lymphoma, Hodgkin's lymphoma, cancer of the nervous system, brain cancer, bone-marrow cancer, bone cancer, kidney cancer, uterine cancer, cervical cancer, colon cancer, retina cancer, skin cancer, bladder cancer, colon cancer, esophageal cancer, testicular cancer, cervical cancer, liver cancer, renal cancer, pancreatic cancer, genital-urinary cancer, gastrointestinal, gum cancer, tongue cancer, kidney cancer, nasopharynx cancer, stomach cancer, endometrial cancer and bowel tumor cell cancer, adrenocarcinomas such as prostate cancer, ovarian cancer, breast cancer, and pancreatic cancer. In particular, the cancer is breast cancer, for example the triple-negative subtype of breast cancer. In one embodiment, a topo I inhibitor is used to treat cancer. In some embodiment the cancer is epithelial in origin, for example, the cancer is, but is not limited to; gastrointestinal cancer, prostate cancer, ovarian cancer, breast cancer, head and neck cancer, lung cancer, small-cell lung cancer, cancer of the nervous system, kidney cancer, retina cancer, skin cancer, liver cancer, pancreatic cancer, genital-urinary cancer and bladder cancer.

In some aspects of the invention, if a subject is identified to be responsive to a topo I inhibitor, a pharmaceutical composition comprising a topo I inhibitor as disclosed herein can be administered alone or with one or more other therapeutic agents. For example, in the treatment of cancer, the pharmaceutical composition can be administered substantially at the same time as, or subsequent to administration of an anti-cancer therapy, such as, for example, chemotherapy, radiotherapy, hormone therapy, thermal therapy, immunotherapy, surgical resection and alternative cancer therapies commonly known by persons of ordinary skill in the art. Such anti-cancer therapies can be administered prior to, during or after administration of the pharmaceutical composition as disclosed herein. In some embodiments, the anti-cancer therapy is administered once, or more than once to the subject.

It is contemplated that any methods or compositions described herein can be implemented with respect of any other methods or compositions. Other objects, features and advantages will become apparent from the following detailed description. It should be understood, however, that the detailed description and specific examples, while indicating specific embodiments of the invention, are given by way of illustration only, since various changes and modifications within the spirit and scope if the invention will become apparent to those skilled in the art from this detailed description.

BRIEF DESCRIPTION OF THE FIGURES

FIGS. 1A-1E shows Ku 70/80 associates with topo I. FIG. 1A shows HeLa cell nuclear lysates were incubated with GST and GST-topo I bound to glutathione sepharose beads and after extensive wash with PBS the adsorbates were eluted with high salt buffer (PBS with 350 and 500 mM NaCl). The adsorbates were analyzed by SDS-PAGE and silver staining. The protein bands were cut and in gel digestion was performed for protein identification by mass spectrometry. FIG. 1B shows GST and GST-topo I bound to glutathione beads were incubated with purified Ku-DNA-PK complex (containing Ku 70/80 heterodimer), the adsorbates were analyzed by immunoblotting with indicated antibodies. To determine the protein directly binding to topoI GST, GST-Ku70 and GST-Ku80 bound to glutathione beads were incubated with topoI protein. FIG. 1C shows The adsorbates were analyzed by immunoblot analysis with anti-topo I. FIG. 1D shows specific Ku70 binding region of topo I was determined by incubation of topo I fragments, and FIG. 1E shows bound to glutathione beads with purified Ku-DNA-PK complex, adsorbates were analyzed by immunoblotting with anti-Ku 70 antibody.

FIG. 2A shows HeLa cell lysates were subjected to immunoprecipitation with anti-Ku70, anti-Ku80, anti-DNA-PK. FIG. 2B shows immunoprecipitation of HeLa cell lysates with anti-topoI, and immunoblotting with anti-Ku-80. FIG. 2C shows immunoprecipitation of HeLa cell lysates with anti-topoI, and immunoblotting with anti-Ku-70. FIG. 2D shows immunoprecipitation of HeLa cell lysates with anti-BRCA1 or PIRS (control), and immunoblotting with anti-TopoI. FIG. 2E shows immunoprecipitation of HA-BRCA1 expressing HeLa cell lysates with anti-HA, and immunoblotting with anti-BRCA1. The precipitates were analyzed by immunoblotting with indicated antibodies.

FIG. 3A shows SDS-PAGE analysis of the reaction products and autoradiography (left lane). FIG. 3A also shows the comparison of an identical reaction in the absence of topoI as a control (right lane). GST-topoI protein band shown in FIG. 3A (left lane) was cut in to small pieces and processed for trypsin digestion. The trypsin digested topoI peptides analyzed by mass spectrometry. FIG. 3B shows the phosphopeptides were enriched by IMAC column and then analyzed by LC-MS-MS (Q-Star, ABI).

FIGS. 4A-4D shows BRCA1 is the E3 ligase for topoI ubiquitination. 700 ng of topo I was incubated with 200 nM E1-His (E1), 5 μM UbcH5c-His (E2) and 200 ng BRCA1-Flag/BARD1 in ubiquitination buffer (10 mM HEPES (pH 7.9), 0.5 mM EDTA, 5 mM MgCl4, 2 mM NaF, 2 mM ATP, 60 mM KCl, 1 uM ubiquitin) and was incubated at 37° C. for 30 minutes. FIG. 4A shows immunoblot analysis using anti-ubiquitin antibody. GST-topoI bound to glutathione bead was phosphorylated by DNA-PK. Kinase reaction was terminated and a part of phosphorylated TopoI was dephosphorylated by calf intestine phosphorylase (CIP). Both phosphorylated and dephosphorylated TopoI were subjected to ubiquitination using a kit (Boston Biochemical, Cambridge, Mass.), and the reaction was terminated and beads were washed, and topoI was eluted by boiling the beads in SDS-PAGE buffer. FIG. 4B shows immunoblotting analysis of the eluted topoI with anti-ubiquitin. GFP-topoI was expressed in HeLa cells by transient transfection using the GenePorter2 kit (Genelantis). BARD1 and BRCA1 were over-expressed using the same method of transient transfection. Negative controls were established by expression of GFP-topoI and over-expression of BARD1 as well as expression of GFP-topoI alone. FIG. 4C shows analysis of cell lysates for GFP-topoI degradation by immunoblot using anti-topoI antibody. FIG. 4D shows % of topoI in elutant samples 1, 2 and 3 from FIG. 4C.

FIG. 5A BT474 cells were subjected to silencing of BRCA1 by shRNA delivered through viral transduction. FIG. 5B shows immunoblot analysis with anti-topoI of BRCA1-silenced and unsilenced BT474 cells showing treatment with CPT for 2 and 6 hours. Protein levels in FIGS. 5A and 5B were determined by immuno blot analysis of cell lysate with anti-βactin. FIG. 5C shows quantification of % topoI expression level in siRNA treated siBRCA1 cells as compared to control cells following treatment with CPT for 0, 3 and 6 hours (FIG. 5B)

FIG. 6B shows the comparative expression of wild type and mutant topoI proteins used in the reaction for FIG. 6A. GST-topoI (WT) (left lane) and GST-topoI-S10A (mutant) (right lane) were analyzed by SDS-PAGE and coomasie staining.

FIG. 7A shows anti-topoI immunoblot analysis of ScSv3 (lane 1) and ScH8 (lane 2) cells. FIG. 7B shows quantification of mRNA levels in the ScSv3 and ScH8 cell samples used for FIG. 7A.

FIG. 8A shows immunoblot with anti-topoI of ScH-8 (DNA-PK +/+ cells) and ScCv-3 (DNA-PK −/− cells) following 0, 3 or 6 hrs of CTP treatment. Protein levels in FIG.

8A were determined by immuno blot analysis of cell lysate with anti-βactin. FIG. 8B shows % topoI expression in wild type cells (DNA-PK +/+, white) and DNA-PK deficient cells (DNA-PK −/−, shaded bars) following 0, 3 or 6 hrs of CTP treatment. FIG. 8C shows the higher percentage of cell death in DNA-PK −/− cells (lower right panel) compared to DNA-PK +/+ cells (upper right panel) in response to CPT, left panel, both upper and lower are controls. FIG. 8D shows % apoptosis of ScSv-3 and ScH8 cells with and without treatment of CPT.

FIG. 9 shows immunoblot with anti-topoI for HeLa cells following CPT treatment in the presence or absence of DNA-PK inhibitor (CTP+DNA-PK inhibitor) (NU7026, 2-morpholin-4-yl)-benzo[h]chromen-4-one). Protein levels were determined by immuno blot analysis of cell lysate with anti-β actin.

FIG. 10 shows TopoI-pS10 is a molecular determinant for CPT response. FIG. 10A shows immunoblot using an anti-pS10 topoI antibody. HeLa cells were treated with CPT for 0 (lane 1), 1 (lane 2), 2 (lane 3) and 4 hours (Lane 4) and cell lysates were analyzed by immunoblot analysis with anti topoI-pS10. FIG. 10B shows protein levels of samples in FIG. 10A by immunoblot analysis with anti-β-actin.

FIG. 11A-11C shows a schematic diagram showing the fate of cellular topoI in the response to anti cancer drug (CPT) treatment. It has been established that topoI is degraded by ubiquitination in the response to CPT. DNA-TopoI-CPT makes cleavage complex during S phase. FIG. 11A shows that due to the presence of CPT topoI fails to religate the cleaved DNA during the religation cycle. The collision of replication fork with cleaved DNA leads to DNA-double strand breaks (DNA-DSB). To repair the DNA-DSB topoI is removed by ubiquitination proteosomal pathway (UPP). However, the mechanism of UPP mediated topoI degradation is not understood. The inventors have demonstrated, as shown by the schematic in FIG. 11B, that topoI associates with Ku-DNA-PK complex, and that DNA-DSB mediated activation of DNA-PK phosphorylates topoI at S10. FIG. 11C is a schematic demonstrating the phosphorylation of topoI at S10 ensures the ubiquitination of topoI by BRCA1/BARD1 heterodimer, and subsequent degradation of the ubiquitinated topoI by ubiquitin-proteosomal pathway.

FIG. 16 shows three colon cancer cell lines; HCT15 (lane 1), Colo205 (lane 2) and Colo320 cells (lane 3) which were lysed and a total of 50 μg protein was analyzed by SDS-PAGE and immunoblotting with topoI S10 Phosphospecific antibody (anti-phospho-S10 topo I antibody; upper panel). The membrane was re-probed with anti β-actin (lower panel) to control for total protein levels.

DETAILED DESCRIPTION OF THE INVENTION

Figure 1D:
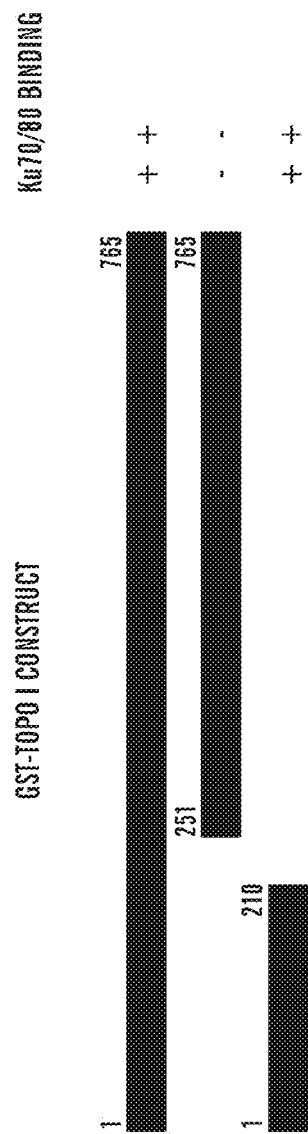
Figure 1E:
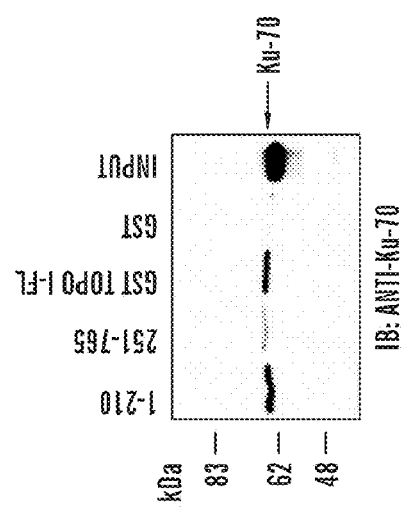

The present invention generally relates to a diagnostic marker for predicting the efficacy of topoisomerase I (topo I) inhibitors in the treatment of cancers. In particular, one aspect of the present invention relates to methods to determine effectiveness of topoisomerase I (topo I) inhibitors in the treatment of cancer. Specifically, the present invention is based on the discovery that the topo I polypeptide is phosphorylated at serine 10 (S10) by the kinase DNA-PK and results in its ubiquitination by BRAC1/BARD1 heterodimer and its subsequent degradation. The inventors have discovered that the presence of phosphorylation of a topo I polypeptide (herein referred to as "phospho-topo I"), in particular the phosphorylation at the serine 10 (S10) amino acid residue of a topo I polypeptide (herein referred to as "phospho-S10 topo I") in a biological sample indicates the resistance and/or unresponsiveness to a topo I inhibitor, such as camptothecin (CPT), or CTP analogues such as topotecan and irinotecan and derivatives thereof. Accordingly, one aspect of the present invention relates to detection of phospho-topo I, and in particular the detection of phospho-S10 topo I in a subject or in a biological sample taken from a subject having, or likely having cancer, as a prognostic determinant for drug efficacy with a topo I inhibitor such as CTP and analogues thereof.

Accordingly, one aspect of the present invention relates to methods, kits, machines, computer systems and computer readable media to detect and analyze the presence phospho-topo I, and in particular the presence of phospho-S10 topo I in a subject having or likely having cancer, or a biological sample taken from such a subject, and if the subject, or biological sample is determined to comprise phospho-topo I, in particular phosphorylation at the serine 10 (S10) residue of the topo I polypeptide (i.e. the presence of phospho-S10 topo I) then the subject, or the subject from which the biological sample was obtained is identified as being likely to be unresponsive to a topo I inhibitor such as camptothecin (CPT), or CTP analogues such as topotecan and irinotecan and derivatives thereof, as compared to a subject with cancer where the corresponding S10 residue on the topo I polypeptide is not phosphorylated.

In all aspects of the inventions as disclosed herein, any means to determine and measure the phosphorylation status of topo I polypeptide are encompassed for use in the present invention. In some embodiments, the phosphorylation status of topo I polypeptide is detected by any means known by a skilled artisan, and can be detected in vivo, in vitro or ex vivo.

In another embodiment, a cancer or cancer cell is identified as likely being responsive to a topo I inhibitor if the cancer cell comprises minimal, or substantially lack of, or the absence of phosphorylated topo I polypeptide, and in particular the absence or substantial lack of phosphorylation on the serine 10 (S10) reside of topo I polypeptide (i.e. the absence of phospho-S10 topo I), where the cancer cell can be present in the subject (for example as detected using in vivo detection method) or in alternative embodiments, the cancer cell can be in a biological sample taken from a subject (for example as detected via in vitro or ex vivo detection methods).

Accordingly, another aspect of the present invention provides a method to identify a subject which is responsive to a topo I inhibitor, such as for example where the subject is currently undergoing or has been selected to be treated for cancer with a topo I inhibitor, for example but not limited to CTP or analogues such as topotecan and irinotecan and other analogues or derivatives thereof.

One aspect of the present invention relates to a method for identifying a subject responsive to a topo I inhibitor, the method comprising measuring the level of phosphorylation of a topoisomerase I polypeptide in a subject, or a biological subject comprising cancer cells taken from a subject; and detecting the level of phosphorylation of the topo I polypeptide, in particular detecting the level of phosphorylation at serine 10 (S10) of the topo I polypeptide, and if the topo I polypeptide is phosphorylated, for example at residue S10, it indicates that the subject has a cancer which is likely to be more unresponsive to a topoisomerase I inhibitor as compared to a subject with cancer where that lacks phosphorylated topo I polypeptide and in particular lacks phospho-S10 topo I polypeptide.

Another aspect of the present invention also relates to a method to identifying the likelihood of a cancer to be unresponsive to a topoisomerase I inhibitor, the method comprising measuring the level of phosphorylation of topoisomerase I polypeptide (i.e. determining the phosphorylation status of topo I polypeptide) in at least one cancer cell, wherein the presence of phosphorylation identifies the cancer as being more likely to be unresponsive to a topoisomerase inhibitor as compared to a cancer wherein the absence of phosphorylation of topoisomerase I is detected. In some embodiments, the cancer cell is present in a subject. In some embodiments, the cancer cell is present in a biological sample. In other embodiments, a cancer cell is a cancer stem cell.

Another aspect of the present invention relates to a method for treating cancer in a subject, the methods comprising: (i) measuring the level of phosphorylation of topoisomerase I polypeptide in a biological sample comprising cancer cells obtained from the subject; (ii) detecting the level of topoisomerase I polypeptide, wherein if the topoisomerase I polypeptide is phosphorylated the cancer is identified as being unresponsive to a topoisomerase I inhibitor, or wherein if the topoisomerase I polypeptide is not phosphorylated the cancer is identified as being likely to be responsive to a topoisomerase I inhibitor; (iii) administering to a subject an anti-cancer agent other than a topoisomerase I inhibitor where the cancer is identified as being unresponsive to a topoisomerase I inhibitor. In some embodiments, subjects identified to be responsive to a topo I inhibitor can then be treated with a topo I inhibitor as that term is described herein, whereas a subject identified to be non-responsive to a topo I inhibitor can be treated with any anti-cancer treatment known to one of ordinary skill in the art which is not a topo I inhibitor, or alternatively, such a subject identified to be non-responsive to a topo I inhibitor can be administered a combination of a topo I inhibitor with (i.e. in conjunction with) an agent which increases a cell's sensitivity to a topo I inhibitor (i.e. a topo I inhibitor sensitivity agent). In some embodiments for example, a topo I inhibitor can be co-administered with an agent which dephosphorylates S10 residue of topo I polypeptide or alternatively with an anent which inhibits the phosphorylation of the S10 residue on topo I, such as an anti-phospho-S10 topo I antibody or an antagonist to DNA-PK.

One aspect of the present invention and all other aspect described herein, a machine can be used to determine phosphorylation status of topo I polypeptides in a biological sample, for example, a machine for obtaining data regarding a biological sample from a subject comprising: a biological sample container to hold the biological sample; a determination module configured to detect the presence of phosphorylation of a topoisomerase I polypeptide, for example the detection of phospho-S10 topo I in the biological sample which produces output data, in some embodiments the output data in a computer readable media format; a storage device configured to store the output data from the determination module; a comparison module adapted to compare the output data from the determination module with data stored on the storage device, such as stored reference data and control data, and a display module for displaying a page of retrieved content for the user on a client computer, wherein (i) the retrieved content is the presence of topoisomerase I polypeptide, and/or (ii) the retrieved content is the presence or absence of phosphorylation of the topoisomerase I polypeptide, for example the retrieved content is the presence or absence of phospho-S10 topo I and/or (iii) the retrieved content is the absence of phosphorylation of topoisomerase I, for example the absence of phospho-S10 topo I, which is a signal that the subject likely to be responsive to topoisomerase I inhibitor; and/or (iv) the retrieved content is the presence of phosphorylation of topoisomerase I, such as the presence of phospho-S10 topo I polypeptide which is a signal that the subject likely to be unresponsive to topoisomerase I inhibitor.

One aspect of the present invention is a computer system that can be used to determine if a subject is responsive to a topo I inhibitor. In such an embodiment, a computer system is connected to a determination module and is configured to obtain output data from a determination module regarding a biological specimen, where a determination module is configured to detect the presence of phosphorylation of a topoisomerase I polypeptide, for example the presence of phospho-S10 topo I polypeptide within a subject or in a biological sample obtained from the subject; and where the computer system comprises (a) a storage device configured to store data output from the determination module as well as reference data; where the storage device is connected to (b) a comparison module which in one embodiment, is adapted to compare the output data stored on the storage device with stored reference data, and in alternative embodiments, adapted to compare the output data with itself, where the comparison module produces report data and is connected to (c) a display module for displaying a page of retrieved content (i.e. report data from the comparison module) for the user on a client computer, wherein the retrieved content comprises any one or a combination of the following; (i) the presence or absence of phosphorylation of the topoisomerase I polypeptide, for example the retrieved content is the presence or absence of phospho-S10 topo I; (ii) the absence of phosphorylation of topoisomerase I, for example the absence of phospho-S10 topo I, (iii) the presence of phosphorylation of topoisomerase I, such as the presence of phospho-S10 topo I polypeptide, (iv) a positive test result (i.e. a positive phosphorylation status such as positive S10 topo I phosphorylation status) which indicates that the subject is likely to be more unresponsive to a topoI inhibitor than a subject having a cancer with a negative phosphorylation status, (v) a negative test result (i.e. a negative phosphorylation status such a negative S10 topo I phosphorylation status) which indicates that the subject is likely to be more responsive to a topoI inhibitor than a subject having a cancer with a positive phosphorylation.

In some embodiments the comparison module compares the output data stored on the storage device with itself or stored reference data, and calculates a positive S10 topo I phosphorylation status (i.e. the presence of phospho-S10 topo I polypeptide) which indicates a positive test result and generates report data to indicate that the subject is likely to be more unresponsive to a topoI inhibitor than a subject having a cancer with a negative phosphorylation status, where the report data from the comparison module is retrieved from the display module and displayed on the display module.

One aspect of the present invention and all other aspect described herein, one can use a computer readable media to determine phosphorylation status of topo I polypeptides from a subject having or at risk of having cancer, for example, a computer readable media having computer readable instructions recorded thereon to define software modules including a determination module and a comparison module for implementing a method on a computer, said method comprising: a storage device configured to store data reference data and output data from a determination module which has measured the presence or absence of the phosphorylation of topo I polypeptide, such as the presence or absence of phospho-S10 topo I polypeptide; a comparison module which generates report data, where the comparison module is adapted to compare the data stored on the storage device, for example a comparison of output data from the determination module with itself or alternatively with reference data, and a display module for displaying a page of retrieved content which is the report data from the comparison module for the user on a client computer, wherein the retrieved content comprises any one or a combination of the following; (i) the presence or absence of phosphorylation of the topoisomerase I polypeptide, for example the retrieved content is the presence or absence of phospho-S10 topo I; (ii) the absence of phosphorylation of topoisomerase I, for example the absence of phospho-S10 topo I, (iii) the presence of phosphorylation of topoisomerase I, such as the presence of phospho-S10 topo I polypeptide, (iv) a positive test result (i.e. a positive phosphorylation status such as positive S10 topo I phosphorylation status) which indicates that the subject is likely to be more unresponsive to a topoI inhibitor than a subject having a cancer with a negative phosphorylation status, (v) a negative test result (i.e. a negative phosphorylation status such a negative S10 topo I phosphorylation status) which indicates that the subject is likely to be more responsive to a topoI inhibitor than a subject having a cancer with a positive phosphorylation.

In some embodiments, a topo I inhibitor useful in the methods as disclosed herein is any agent or entity which inhibits the biological activity, such as protein activity of topoisomerase, including but not limited to camptothecin (CPT), or CTP analogues such as topotecan and irinotecan and derivatives thereof, CTP compounds, CTP metabolites, CTP derivatives and mimetics thereof.

In an alternative embodiment, a subject identified to be responsive to a topo I inhibitor can be administered a topo I inhibitor, such as for example but not limited to CTP or analogues thereof.

In one embodiment the cancer is SCLC, colon or ovarian cancer, or a refractory cancer, for example, breast cancer or cervical cancer. In other embodiments, a cancer useful to be treated in the methods as disclosed herein is any cancer which can be treated, or is desirable to be treated with a topo I inhibitor and includes, for example but are not limited to cancers comprising those of epithelial origin, including, but are not limited to, gastrointestinal cancer, prostate cancer, ovarian cancer, breast cancer, head and neck cancer, lung cancer, non-small cell lung cancer, cancer of the nervous system, kidney cancer, retina cancer, skin cancer, liver cancer, pancreatic cancer, genital-urinary cancer and bladder cancer. In one embodiment, the cancer is non-small cell lung cancer. In another embodiment, the cancer is triple-negative subtype of cancer, which lacks the expression of the progesterone receptor (PR), the estrogen receptor (ER) and also lacks Her-2 amplification.

Tumor cell types can also be selected from a group comprising of gastrointestinal cancer, gastric cancer, squamous cell carcinomas (SCC), head and neck cancer, lung cancer, non-small cell lung cancer (NSCLC) and small-cell lung cancer (SCLC), lymphoma, sarcoma, primary and metastic melanoma, thymoma, non-Hodgkin's lymphoma, Hodgkin's lymphoma, cancer of the nervous system, brain cancer, bone-marrow cancer, bone cancer, kidney cancer, uterine cancer, cervical cancer, colon cancer, retina cancer, skin cancer, bladder cancer, colon cancer, esophageal cancer, testicular cancer, cervical cancer, liver cancer, renal cancer, pancreatic cancer, genital-urinary cancer, gastrointestinal, gum cancer, tongue cancer, kidney cancer, nasopharynx cancer, stomach cancer, endometrial cancer and bowel tumor cell cancer, adrenocarcinomas such as prostate cancer, ovarian cancer, breast cancer, and pancreatic cancer.

Definitions

For convenience, certain terms employed in the entire application (including the specification, examples, and appended claims) are collected here. Unless defined otherwise, all technical and scientific terms used herein have the same meaning as commonly understood by one of ordinary skill in the art to which this invention belongs.

The term "topoisomerase I" is used interchangeably herein with "topo I" and refers to the polypeptide encoded by SEQ ID NO: 2 and variants and homologues thereof, including conservative substitutions, additions, deletions therein not adversely affecting the structure of function. Topoisomerase I is referred in the art as TOPI or TOP1. Human topo I is encoded by nucleic acid corresponding to GenBank Accession No: BC136297.1 (SEQ ID NO: 3) or GI:223460079 and the human topo I polypeptide corresponds to protein sequence corresponding to RefSeq ID No: NM_003286 or NP_003277.1. DNA topoisomerase is an enzyme that controls and alters the topologic states of DNA during transcription, and catalyzes the transient breaking and rejoining of a single strand of DNA which allows the strands to pass through one another, thus altering the topology of DNA. The gene for TOP1 is localized to chromosome 20 and has pseudogenes which reside on chromosomes 1 and 22. The biological activity of topo I polypeptide refers to the polypeptides enzymatic activity to catalyze the transient breaking and rejoining of a single strand of DNA, where one strand pass through one another, thus altering the topology of DNA.

The term "inhibitor" as used herein refers to any agent or entity which results in the inhibition of a proteins biological activity. By a "decrease" or "inhibition" used in the context of the level of activity of a gene refers to a reduction in protein or nucleic acid level or biological activity in a cell, a cell extract, or a cell supernatant. For example, such inhibition may be due to decreased binding of the polypeptide to its endogenous ligand, or by non-completive binding of an inhibitor to a polypeptide to reduce catalytic activity or affinity for target ligand etc, or alternatively to reduced RNA stability, transcription, or translation, increased protein degradation, or RNA interference. Preferably, a decrease is at least about 5%, at least about 10%, at least about 25%, at least about 50%, at least about 75%, at least about 80%, or even at least about 90% of the level of expression or activity under control conditions.

By an "increase" in the expression or activity of a gene or protein is meant a positive change in protein or polypeptide or nucleic acid level or activity in a cell, a cell extract, or a cell supernatant. For example, such a increase may be due to increased RNA stability, transcription, or translation, or decreased protein degradation. Preferably, this increase is at least 5%, at least about 10%, at least about 25%, at least about 50%, at least about 75%, at least about 80%, at least about 100%, at least about 200%, or even about 500% or more over the level of expression or activity under control conditions.

The term "topo I inhibitor" as used herein refers to any entity which mediates some, all or part of its biological function, through acting directly or indirectly on the gene product or polynucleotide of topoisomerase I polypeptide. A topo I inhibitor can directly or indirectly inactivate topo I polypeptide.

Exemplarily examples of topo I inhibitor include for example but not limited to, camptothecin (CTP) and analogues thereof including but not limited to irinotecan and topotecan, and derivatives thereof, as these terms are described herein.

The term "CTP" can include a "mimetic" of CTP or a derivative or analogue thereof, which includes compounds which may not be structurally similar to CTP but mimic the therapeutic activity or therapeutic mechanism of CTP or structurally similar CTP compound in vitro and in vivo.

As used herein, the terms "effective" and "effectiveness" or "responsive" includes both pharmacological effectiveness and physiological safety of an agent, such as a topo I inhibitor. "Pharmacological effectiveness" refers to the ability of the treatment to result in a desired biological effect in the subject. "Physiological safety" refers to the level of toxicity, or other adverse physiological effects at the cellular, organ and/or organism level (often referred to as side-effects) resulting from administration of the treatment, "less effective" means that the treatment results in a therapeutically significant lower level of pharmacological effectiveness and/or a therapeutically greater level of adverse physiological effects.

The term "lack of effectiveness", "non-responsiveness", "refractory" or "unresponsiveness" are used interchangeably herein, and refer to the inability of an agent or treatment to result in a desired biological effect in the subject.

The term "phosphorylation status" as used herein comprises the absolute or relative degree of phosphorylation of proteins and/or reagents. The term phosphorylation status of topo I is the degree of phosphorylation on all phosphorylation sites on the topo I polypeptide, and includes the degree (or level) of phosphorylation on the serine 10 (S10) amino acid residue on the topo I polypeptide.

The term "activity" when used in reference to the activity of a protein as used herein, comprises the enzymatic activity, binding affinity and/or posttranslational activity, in particular phosphorylation.

The term "target" as used herein may mean a polynucleotide that may be bound by one or more probes under stringent hybridization conditions.

The term "entity" refers to any structural molecule or combination of molecules.

The term "drug", "agent" or "compound" as used herein refers to a chemical entity or biological product, or combination of chemical entities or biological products, administered to a person to treat or prevent or control a disease or condition. The chemical entity or biological product is preferably, but not necessarily a low molecular weight compound, but may also be a larger compound, for example, an oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof.

The term "agent" refers to any entity which is normally absent or not present at the levels being administered, in the cell. Agent may be selected from a group comprising; chemicals; small molecules; nucleic acid sequences; nucleic acid analogues; proteins; peptides; aptamers; antibodies; or fragments thereof. A nucleic acid sequence may be RNA or DNA, and may be single or double stranded, and can be selected from a group comprising; nucleic acid encoding a protein of interest, oligonucleotides, nucleic acid analogues, for example peptide-nucleic acid (PNA), pseudo-complementary PNA (pc-PNA), locked nucleic acid (LNA), etc. Such nucleic acid sequences include, for example, but not limited to, nucleic acid sequence encoding proteins, for example that act as transcriptional repressors, antisense molecules, ribozymes, small inhibitory nucleic acid sequences, for example but not limited to RNAi, shRNAi, siRNA, micro RNAi (mRNAi), antisense oligonucleotides etc. A protein and/or peptide or fragment thereof can be any protein of interest, for example, but not limited to; mutated proteins; therapeutic proteins; truncated proteins, wherein the protein is normally absent or expressed at lower levels in the cell. Proteins can also be selected from a group comprising; mutated proteins, genetically engineered proteins, peptides, synthetic peptides, recombinant proteins, chimeric proteins, antibodies, midibodies, tribodies, humanized proteins, humanized antibodies, chimeric antibodies, modified proteins and fragments thereof. The agent may be applied to the media, where it contacts the cell and induces its effects. Alternatively, the agent may be intracellular within the cell as a result of introduction of the nucleic acid sequence into the cell and its transcription resulting in the production of the nucleic acid and/or protein environmental stimuli within the cell. In some embodiments, the agent is any chemical, entity or moiety, including without limitation synthetic and naturally-occurring non-proteinaceous entities. In certain embodiments the agent is a small molecule having a chemical moiety. For example, chemical moieties included unsubstituted or substituted alkyl, aromatic, or heterocyclyl moieties including macrolides, leptomycins and related natural products or analogues thereof. Agents can be known to have a desired activity and/or property, or can be selected from a library of diverse compounds.

The term "antagonist" refers to any agent or entity capable of inhibiting the expression or activity of a protein, polypeptide portion thereof, or polynucleotide. Thus, the antagonist may operate to prevent transcription, translation, post-transcriptional or post-translational processing or otherwise inhibit the activity of the protein, polypeptide or polynucleotide in any way, via either direct of indirect action. The antagonist may for example be a nucleic acid, peptide, or any other suitable chemical compound or molecule or any combination of these. Additionally, it will be understood that in indirectly impairing the activity of a protein, polypeptide of polynucleotide, the antagonist may affect the activity of the cellular molecules which may in turn act as regulators or the protein, polypeptide or polynucleotide itself. Similarly, the antagonist may affect the activity of molecules which are themselves subject to the regulation or modulation by the protein, polypeptide of polynucleotide.

The term "inhibiting" as used herein as it pertains to the expression or activity of the protein or polypeptide of topoisomerase I or variants thereof does not necessarily mean complete inhibition of expression and/or activity. Rather, expression or activity of the protein, polypeptide or polynucleotide is inhibited to an extent, and/or for a time, sufficient to produce the desired effect.

The term "protein binding moiety" is used interchangeably herein with "protein binding molecule" or protein binding entity" and refers to any entity which has specific affinity for a protein. The term "protein-binding molecule" also includes antibody-based binding moieties and antibodies and includes immunoglobulin molecules and immunologically active determinants of immunoglobulin molecules, e.g., molecules that contain an antigen binding site which specifically binds (immunoreacts with) to the Psap proteins. The term "antibody-based binding moiety" is intended to include whole antibodies, e.g., of any isotype (IgG, IgA, IgM, IgE, etc), and includes fragments thereof which are also specifically reactive with the Psap proteins. Antibodies can be fragmented using conventional techniques. Thus, the term includes segments of proteolytically-cleaved or recombinantly-prepared portions of an antibody molecule that are capable of selectively reacting with a certain protein. Non limiting examples of such proteolytic and/or recombinant fragments include Fab, F(ab')2, Fab', Fv, dAbs and single chain antibodies (scFv) containing a VL and VH domain joined by a peptide linker. The scFv's can be covalently or non-covalently linked to form antibodies having two or more binding sites. Thus, "antibody-base binding moiety" includes polyclonal, monoclonal, or other purified preparations of antibodies and recombinant antibodies. The term "antibody-base binding moiety" is further intended to include humanized antibodies, bispecific antibodies, and chimeric molecules having at least one antigen binding determinant derived from an antibody molecule. In a preferred embodiment, the antibody-based binding moiety detectably labeled. In some embodiments, a "protein-binding molecule" is a co-factor or binding protein that interacts with the protein to be measured, for example a co-factor or binding protein to a topo I polypeptide protein.

The term "labeled antibody", as used herein, includes antibodies that are labeled by a detectable means and include, but are not limited to, antibodies that are enzymatically, radioactively, fluorescently, and chemiluminescently labeled. Antibodies can also be labeled with a detectable tag, such as c-Myc, HA, VSV-G, HSV, FLAG, V5, or HIS. The detection and quantification of Psap or Tsp-1 present in the tissue samples correlate to the intensity of the signal emitted from the detectably labeled antibody.

The term "specific affinity" or "specifically binds" or "specific binding" are used interchangeably herein refers to an entity such as a protein-binding molecule or antibody that recognizes and binds a desired polypeptide but that does not substantially recognize and bind other molecules in a sample, for example, a biological sample, which naturally includes a polypeptide of the invention, for example phospho-S10 topo I polypeptide.

The term "antibody" is meant to be an immunoglobulin protein that is capable of binding an antigen. Antibody as used herein is meant to include antibody fragments, e.g. F(ab')$_2$, Fab', Fab, capable of binding the antigen or antigenic fragment of interest.

The term "humanized antibody" is used herein to describe complete antibody molecules, i.e. composed of two complete light chains and two complete heavy chains, as well as antibodies consisting only of antibody fragments, e.g. Fab, Fab', F(ab')$_2$, and Fv, wherein the CDRs are derived from a non-human source and the remaining portion of the Ig molecule or fragment thereof is derived from a human antibody, preferably produced from a nucleic acid sequence encoding a human antibody.

The terms "human antibody" and "humanized antibody" are used herein to describe an antibody of which all portions of the antibody molecule are derived from a nucleic acid sequence encoding a human antibody. Such human antibodies are most desirable for use in antibody therapies, as such antibodies would elicit little or no immune response in the human subject.

The term "chimeric antibody" is used herein to describe an antibody molecule as well as antibody fragments, as described above in the definition of the term "humanized antibody." The term "chimeric antibody" encompasses humanized antibodies. Chimeric antibodies have at least one portion of a heavy or light chain amino acid sequence derived from a first mammalian species and another portion of the heavy or light chain amino acid sequence derived from a second, different mammalian species. In some embodiments, a variable region is derived from a non-human mammalian species and the constant region is derived from a human species. Specifically, the chimeric antibody is preferably produced from a 9 nucleotide sequence from a non-human mammal encoding a variable region and a nucleotide sequence from a human encoding a constant region of an antibody.

In the context of this invention, the term "probe" refers to a molecule which can detectably distinguish between target molecules differing in structure. Detection can be accomplished in a variety of different ways depending on the type of probe used and the type of target molecule, thus, for example, detection may be based on discrimination of activity levels of the target molecule, but preferably is based on detection of specific binding. Examples of such specific binding include antibody binding and nucleic acid probe hybridization. Thus, for example, probes can include enzyme substrates, antibodies and antibody fragments, and preferably nucleic acid hybridization probes.

The term "label" refers to a composition capable of producing a detectable signal indicative of the presence of the target polynucleotide in an assay sample. Suitable labels include radioisotopes, nucleotide chromophores, enzymes, substrates, fluorescent molecules, chemiluminescent moieties, magnetic particles, bioluminescent moieties, and the like. As such, a label is any composition detectable by spectroscopic, photochemical, biochemical, immunochemical, electrical, optical or chemical means.

As used herein the term "reference data" when used in the context of the reference level of phosphorylation refers to the level of phosphorylation of topo I, in particular the level of phosphorylation on serine 10 of topo I in at least one reference biological sample, or a group of biological samples from at least subject or a group of subjects which have been identified to be non-responsive or responsive to a topo I inhibitor. By way of example, a positive reference level is a level of the degree of phosphorylation, in particular the level of phosphorylation at S10 of topo I which indicates the sample is non-responsive to a topo I inhibitor, whereas a negative reference level is a level of the degree of phosphorylation, in particular the level of phosphorylation at S10 of topo I which indicates the sample is responsive to a topo I inhibitor. In some embodiments, a positive reference level is normalized to 100%, where 100% of the total topo I polypeptide is phosphorylated, for example 100% of topo I exists as phospho-S10-topoI, and in some embodiments a negative reference level is normalized to 0%, where 0% of the total topo I polypeptide is phosphorylated, for example 0% of topo I exists as phospho-S10-topoI. Thus, so an increase in the level of a phosphorylation of topo I, such as an increase of at least 1% to 100% of the level of phosphorylation at S10 of topo I in a biological sample as compared with a negative reference level, including all percentages between 1% and 100%, i.e. at least 1%, 2%, 3%, 4%, 5%, 10%, 15%, 20%, 25%, 30%, 35%, 40%, 45%, 50%, 60%, 70%, 80%, 90%, 95%, 100% indicates the degree of likelihood (i.e. %) the biological sample is likely to be unresponsive to a topo I inhibitor. Stated another way, if 50% of the total available topo I protein is detected to be phospho-S10 topo I, then the efficacy of the topo I inhibitor is likely to be reduced by 50% as compared to the efficacy of the topo I inhibitor if 0% of the total available topo I protein exists as phospho-S10 topo I (i.e. topo I is not phosphorylated at S10).

The term "support" refers to conventional supports such as beads, particles, dipsticks, fibers, filters, membranes and silane or silicate supports such as glass slides.

The term "cancer", as used herein refers to a cellular proliferative disease in a human or animal subject.

The terms "tumor" or "tumor cell" or "cancer cell" are used interchangeably herein refers to the tissue mass or tissue type or cell type that is undergoing uncontrolled proliferation.

The term "tissue" is intended to include intact cells, blood, blood preparations such as plasma and serum, bones, joints, muscles, smooth muscles, and organs.

The term "Triple-negative subtype" used herein refers to any subtype of cancer, particularly breast cancer, which lacks the expression of the progesterone receptor (PR), lacks the estrogen receptor (ER) and also lacks Her-2 amplification.

As used herein, the term "biological sample" also refers to a cell or population of cells or a quantity of tissue or fluid from a subject. Most often, the sample has been removed from a subject, but the term "biological sample" can also refer to cells or tissue analyzed in vivo, i.e. without removal from the subject. Often, a "biological sample" will contain cells from a subject, but the term can also refer to non-cellular biological material, such as non-cellular fractions of blood, saliva, or urine, that can be used to measure protein phosphorylation levels. As used herein, a "biological sample" or "tissue sample" refers to a sample of tissue or fluid isolated from an individual, including but not limited to, for example, blood, plasma, serum, tumor biopsy, urine, stool, sputum, spinal fluid, pleural fluid, nipple aspirates, lymph fluid, the external sections of the skin, respiratory, intestinal, and genitourinary tracts, tears, saliva, milk, cells (including but not limited to blood cells), tumors, organs, and also samples of in vitro cell culture constituent. In some embodiments, a biological sample is from a resection, bronchoscopic biopsy, or core needle biopsy of a primary, secondary or metastatic tumor, or a cellblock from pleural fluid. In addition, fine needle aspirate biological samples are also useful. In some embodiments, a biological sample is primary ascite cells. Samples can be fresh, frozen, fixed or optionally paraffin-embedded, frozen or subjected to other tissue preservation methods, including for example methods to preserve the phosphorylation status of polypeptides in the biological sample. A biological sample can also mean a sample of biological tissue or fluid that comprises protein or cells. Such samples include, but are not limited to, tissue isolated from subjects or animals. Biological samples may also include sections of tissues such as biopsy and autopsy samples, frozen sections taken for histological purposes, blood, plasma, serum, sputum, stool, tears, mucus, hair, and skin. Biological samples also include explants and primary and/or transformed cell cultures derived from patient tissues. A biological sample may be provided by removing a sample of cells from subject, but can also be accomplished by using previously isolated cells (e.g., isolated by another person, at another time, and/or for another purpose), or by performing the methods of the invention in vivo. Archival tissues, such as those having treatment or outcome history may also be used. Biological samples include, but are not limited to, tissue biopsies, scrapes (e.g. buccal scrapes), whole blood, plasma, serum, urine, saliva, cell culture, or cerebrospinal fluid. Biological samples also include tissue biopsies, cell culture. The sample can be obtained by removing a sample of cells from a subject, but can also be accomplished by using previously isolated cells (e.g. isolated by another person), or by performing the methods of the invention in vivo.

The term 'malignancy' and 'cancer' are used interchangeably herein, refers to diseases that are characterized by uncontrolled, abnormal growth of cells. Cancer cells can spread locally or through the bloodstream and lymphatic system to other parts of the body. The term "malignancy" or "cancer" are used interchangeably herein and refers to any disease of an organ or tissue in mammals characterized by poorly controlled or uncontrolled multiplication of normal or abnormal cells in that tissue and its effect on the body as a whole. Cancer diseases within the scope of the definition comprise benign neoplasms, dysplasias, hyperplasias as well as neoplasms showing metastatic growth or any other transformations like e.g. leukoplakias which often precede a breakout of cancer.

The terms "patient", "subject" and "individual" are used interchangeably herein, and refer to an animal, particularly a human, to whom treatment including prophylaxic treatment is provided. The term "subject" as used herein refers to human and non-human animals. The term "non-human animals" and "non-human mammals" are used interchangeably herein includes all vertebrates, e.g., mammals, such as non-human primates, (particularly higher primates), sheep, dog, rodent (e.g. mouse or rat), guinea pig, goat, pig, cat, rabbits, cows, and non-mammals such as chickens, amphibians, reptiles etc. In one embodiment, the subject is human. In another embodiment, the subject is an experimental animal or animal substitute as a disease model.

The term "effective amount" includes within its meaning a sufficient amount of a pharmacological composition to provide the desired effect. The exact amount required will vary depending on factors such as the level of phosphorylation (i.e. presence or absence of phosphorylation of topo I, such as phosphorylation of S10 of topo I), the type of tumor to be treated, the severity of the tumor, the drug resistance level of the tumor, the species being treated, the age and general condition of the subject, the particular topo I inhibitor being used as a treatment, the mode of administration and so forth. Thus, it is not possible to specify the exact "effective amount". However, for any given case, an appropriate "effective amount" may be determined by one of ordinary skill in the art using only routine experimentation. As used herein, the effective amount is the amount of an agent or treatment to reduce a symptom of the disease, for example, but not limited to, to reduce the size of a tumor, for example to reduce the size by about 10%, to attenuate the growth rate of the tumor, for example to reduce the rate at which a tumor grows by 10%. For example, an effective amount using the methods as disclosed herein would be considered as the amount sufficient to reduce a symptom of the cancer, for example at least one symptom of a cancer or malignancy by at least 10%. Further, an effective amount as used herein would also include an amount sufficient to prevent or delay the development of a symptom of the disease, alter the course of a symptom disease (for example but not limited to, slow the progression of a symptom of the disease), or reverse a symptom of the disease.

As used herein, the term "treating" includes reducing or alleviating at least one adverse effect or symptom of a condition, disease or disorder associated with cancer. As used herein, the term treating is used to refer to the reduction of a symptom and/or a biochemical marker of cancer, for example a reduction in at least one biochemical marker of cancer by at least 10%. For example but are not limited to, a reduction in a biochemical marker of cancer, for example a reduction in, as an illustrative example only, at least one of the following biomarkers; CD44, telomerase, TGF-α, TGF-β, erbB-2, erbB-3, MUC1, MUC2, CK20, PSA, CA125, FOBT, by 10%, or a reduction in the rate of proliferation of the cancer cells by 10%, would be considered effective treatments by the methods as disclosed herein. As alternative examples, a reduction in a symptom of cancer, for example, a slowing of the rate of growth of the cancer by 10% or a cessation of the increase in tumor size, or a reduction in the size of a tumor by 10% or a reduction in the tumor spread (i.e. tumor metastasis) by 10% would also be considered as affective treatments by the methods as disclosed herein.

The term "polynucleotide" as used herein, refers to single- or double-stranded polymer of deoxyribonucleotide, ribonucleotide bases or known analogies of natural nucleotides, or mixtures thereof. The term includes reference to the specified sequence as well as to the sequence complementary thereto, unless otherwise indicated.

The term "polypeptide" means a polymer made up of amino acids linked together by peptide bonds. The terms "polypeptide" and "protein" are used interchangeably herein, although for the purposes for the present invention, a polypeptide may constitute a portion or the full length protein.

The term "expression" as used herein refers to interchangeably to the expression of a polypeptide or protein and expression of a polynucleotide or gene. Expression of a polynucleotide may be determined, for example, by measuring the production of messenger RNA (mRNA) transcript levels. Expression of a protein or polypeptide may be determined, for example, by immunoassay using an antibody(ies) that bind with the polypeptide.

The term "endogenously expressed" or "endogenous expression" as used herein, refers to the expression of a gene product at normal levels and under normal regulation for that cell type.

In the context of this specification, the term "activity" as it pertains to a protein, polypeptide or polynucleotide means any cellular function, action, effect of influence exerted by the protein, polypeptide or polynucleotide, either by nucleic acid sequence or fragment thereof, or by the protein or polypeptide itself or any fragment thereof.

The term "nucleic acid" or "oligonucleotide" or "polynucleotide" used herein can mean at least two nucleotides covalently linked together. As will be appreciated by those in the art, the depiction of a single strand also defines the sequence of the complementary strand. Thus, a nucleic acid also encompasses the complementary strand of a depicted single strand. As will also be appreciated by those in the art, many variants of a nucleic acid can be used for the same purpose as a given nucleic acid. Thus, a nucleic acid also encompasses substantially identical nucleic acids and complements thereof. As will also be appreciated by those in the art, a single strand provides a probe for a probe that can hybridize to the target sequence under stringent hybridization conditions. Thus, a nucleic acid also encompasses a probe that hybridizes under stringent hybridization conditions.

The term "RNAi" as used herein refers to RNA interference (RNAi) a RNA-based molecule that inhibits gene expression. RNAi refers to a means of selective post-transcriptional gene silencing by destruction of specific mRNA by small interfering RNA molecules (siRNA). The siRNA is typically generated by cleavage of double stranded RNA, where one strand is identical to the message to be inactivated. As used herein, the term "RNAi" refers to any type of interfering RNA, including but are not limited to, siRNAi, shRNAi, endogenous microRNA and artificial microRNA. For instance, it includes sequences previously identified as siRNA, regardless of the mechanism of down-stream processing of the RNA (i.e. although siRNAs are believed to have a specific method of in vivo processing resulting in the cleavage of mRNA, such sequences can be incorporated into the vectors in the context of the flanking sequences described herein).

As used herein an "siRNA" refers to a nucleic acid that forms a double stranded RNA, which double stranded RNA has the ability to reduce or inhibit expression of a gene or target gene when the siRNA is present or expressed in the same cell as the target gene, for example where a target gene is for example DNA-PK. The double stranded RNA siRNA can be formed by the complementary strands. In one embodiment, a siRNA refers to a nucleic acid that can form a double stranded siRNA. The sequence of the siRNA can correspond to the full length target gene, or a subsequence thereof. Typically, the siRNA is at least about 15-50 nucleotides in length (e.g., each complementary sequence of the double stranded siRNA is about 15-50 nucleotides in length, and the double stranded siRNA is about 15-50 base pairs in length, preferably about 19-30 base nucleotides, preferably about 20-25 nucleotides in length, e.g., 20, 21, 22, 23, 24, 25, 26, 27, 28, 29, or 30 nucleotides in length).

As used herein "shRNA" or "small hairpin RNA" (also called stem loop) is a type of siRNA. In one embodiment, these shRNAs are composed of a short, e.g. about 19 to about 25 nucleotide, antisense strand, followed by a nucleotide loop of about 5 to about 9 nucleotides, and the analogous sense strand. Alternatively, the sense strand can precede the nucleotide loop structure and the antisense strand can follow.

The term "anti-cancer agent" or "anti-cancer drug" as used herein refers to any agent, compound or entity that would be capably of negatively affecting the cancer in the subject, for example killing cancer cells, inducing apoptosis in cancer cells, reducing the growth rate of cancer cells, reducing the number of mestatic cells, reducing tumor size, inhibiting tumor growth, reducing blood supply to a tumor or cancer cells, promoting an immune response against cancer cells or a tumor, preventing or inhibiting the progression of cancer, or increasing the lifespan of the subject with cancer. An anti-cancer therapy encompasses any immunotherapy or biological agent (biotherapy), chemotherapy agents, and radiotherapy agents. The combination of chemotherapy with biological therapy is known in the art as biochemotherapy.

The term "computer" can refer to any apparatus that is capable of accepting a structured input, processing the structured input according to prescribed rules, and producing results of the processing as output. Examples of a computer include: a computer; a general purpose computer; a supercomputer; a mainframe; a super mini-computer; a mini-computer; a workstation; a micro-computer; a server; an interactive television; a hybrid combination of a computer and an interactive television; and application-specific hardware to emulate a computer and/or software. A computer can have a single processor or multiple processors, which can operate in parallel and/or not in parallel. A computer also refers to two or more computers connected together via a network for transmitting or receiving information between the computers. An example of such a computer includes a distributed computer system for processing information via computers linked by a network.

The term "computer-readable medium" may refer to any storage device used for storing data accessible by a computer, as well as any other means for providing access to data by a computer. Examples of a storage-device-type computer-readable medium include: a magnetic hard disk; a floppy disk; an optical disk, such as a CD-ROM and a DVD; a magnetic tape; a memory chip.

The term "software" can refer to prescribed rules to operate a computer. Examples of software include: software; code segments; instructions; computer programs; and programmed logic.

The term a "computer system" may refer to a system having a computer, where the computer comprises a computer-readable medium embodying software to operate the computer.

The term "proteomics" may refer to the study of the expression, structure, and function of proteins within cells, including the way they work and interact with each other, providing different information than genomic analysis of gene expression.

Compositions or methods "comprising" one or more recited elements may include other elements not specifically recited. For example, a composition that comprises a fibril component peptide encompasses both the isolated peptide and the peptide as a component of a larger polypeptide sequence. By way of further example, a composition that comprises elements A and B also encompasses a composition consisting of A, B and C. The terms "comprising" means "including principally, but not necessary solely". Furthermore, variation of the word "comprising", such as "comprise" and "comprises", have correspondingly varied meanings. The term "consisting essentially" means "including principally, but not necessary solely at least one", and as such, is intended to mean a "selection of one or more, and in any combination." In the context of the specification, the term "comprising" means "including principally, but not necessary solely". Furthermore, variation of the word "comprising", such as "comprise" and "comprises", have correspondingly varied meanings.

The use of the word "a" or "an" when used in conjunction with the term "comprising" in the claims and/or the specification may mean "one" but is also consistent with the meaning of "one or more", "at least one" and "one or more than one."

Other than in the operating examples, or where otherwise indicated, all numbers expressing quantities of ingredients or reaction conditions used herein should be understood as modified in all instances by the term "about." The term "about" when used in connection with percentages can mean±1%.

This invention is further illustrated by the following examples which should not be construed as limiting. The contents of all references cited throughout this application, as well as the figures and tables are incorporated herein by reference.

It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

Methods to Identify a Cancer Responsive to a Topo I Inhibitor

In some embodiments, the methods disclosed herein encompass determining the phosphorylation status of topo I polypeptide (i.e. the presence of phosphorylation of topo I), for example the phosphorylation at the serine 10 residue of the topo I polypeptide in a biological sample, for example a biological sample comprising cancer cells from a subject with or at risk for developing a cancer.

One aspect of the present invention relates to a method to determine the likelihood of a topo I inhibitor being effective in a subject with, or at risk of developing cancer. In one embodiment the cancer is SCLC, colon or ovarian cancer, or a refractory cancer, for example, breast cancer or cervical cancer. In one embodiment, the method comprises detecting the presence of phosphorylation, in particular the presence of phosphorylation at the serine 10 (S10) amino acid residue on topoisomerase polypeptide in a biological subject, and in some embodiments, the biological subject is obtained from a subject. In one embodiment, a method to determine the likelihood of a topo I inhibitor being effective in a subject affected with, or at risk of developing cancer comprises determining the phosphorylation status of the topoisomerase I polypeptide in a biological sample. In particular embodiments of all aspects described herein, a method to determine the likelihood of a topo I inhibitor being effective in a subject affected with, or at risk of developing cancer comprises determining the presence of phosphorylation at serine 10 (S10) amino acid residue of the topoisomerase I polypeptide in a biological sample obtained from a subject. In particular, the presence of phosphorylation at serine 10 (S10) amino acid residue of the topoisomerase I polypeptide identifies that a topo I inhibitor is likely not to be effective in a subject, whereas the absence of a phosphate group (i.e. lack of phosphorylation at the serine 10 (S10) amino acid residue of the topoisomerase I polypeptide indicates that a topo I inhibitor is likely to be effective in a subject.

Another aspect of the invention relates to the use of methods, kits, machines, computer systems and computer readable media as disclosed herein to identify subjects that have cancers which are likely to be responsive to a topo I inhibitor, the methods, kits, machines, computer systems and computer readable media employing detection of phosphorylation at S10 of topoisomerase I polypeptide in a biological sample from a subject with cancer, where the absence of phosphorylation at S10 of topo I in the biological sample identifies a subject with cancer which is likely to be responsive to a topo I inhibitor. In some embodiments, a cancer comprises at least one cancer cell.

In all aspects of the invention as described herein, a topo I inhibitor is likely to be not to effective (i.e. to lack efficacy) in a subject with cancer if a biological subject obtained from the subject comprises a phosphorylated form of the topo I polypeptide (herein referred to as "phospho-topo I"). In a particular aspect of the invention, a topo I inhibitor is likely to not be effective (i.e. to lack efficacy) in the subject with cancer if a biological subject obtained from the subject comprises phosphorylation at the serine 10 (S10) amino acid residue of the topo I polypeptide (herein referred to as "phospho-S10 topo I"). The presence of phospho-topo I and/or phospho-S10 topoI in a biological sample indicates that the subject from which the biological sample was obtained is unresponsive or non-responsive to a topo I inhibitor. Stated another way for example, if there is lack of phosphorylation, in particular lack of phosphorylation at S10 of the topo I polypeptide in a biological sample indicates that the subject from which the biological sample was obtained is likely to be responsive to a topo I inhibitor.

Methods to Identify a Cancer Unresponsive to a Topo I Inhibitor

In another embodiment, the methods, kits, machines, computer systems and computer readable media as disclosed herein can be used to determine if a cancer in a subject is unresponsive to a topo I inhibitor such as CPT or analogues thereof where the methods, kits, machines, computer systems or computer readable media assess a biological sample from a subject with cancer, and if a biological sample is determined to have a phosphorylation of topo I, in particular the phosphorylation of serine 10 (S10) on topo I (i.e. phospho-S10-topoI), it identifies a subject having or likely having a cancer which is unresponsive to a topo I inhibitor, such as CPT and derivatives and analogues thereof.

In some embodiments of this aspect and all aspect described herein, the presence of phospho-S10-topoI can be determined by a machine, computer system or computer readable media as described herein, wherein the presence of phosphorylation of topo I, in particular the presence of phospho-S10-topoI is determined by a determination module, followed by comparative analysis with a reference sample comparison with stored data, for instance in stored reference data in a comparison module and displaying the retrieved data with a display module method.

The term "biological sample" is intended to include tissues, cells and biological fluids isolated from a subject, as well as tissues, cells and fluids present within a subject. In some embodiments, the methods as disclosed herein provide for the detection of the phosphorylation status of topo I using commonly known methods of ordinary skill in the art, which include for example but are not limited to; enzyme linked immunosorbent assays (ELISAs), Western blots, immunoprecipitations, immunofluorescence etc.

In some embodiments, the method also encompasses techniques for detecting the phosphorylation status of topo I polypeptide, in particular the phospho-S10 topo I in cancer cell in vivo. As a non-limiting example, the methods as disclosed here encompass introducing into a subject a labeled antibody or protein-binding molecule specific for phospho-S10 topo I. In some embodiments, the antibodies can be labeled with markers whose presence and location in a subject can be detected by standard imaging techniques, for example such markers, include but are not limited to radioactive, fluorescence and bioluminescence markers etc. In one embodiment, the biological sample contains cancer cells from a subject.

In some embodiments, the level of phosphorylation of topo I of a biological sample is compared against a reference level of phosphorylation of topo I using the methods, kits, machines, computer systems and computer readable media as disclosed herein. A reference level of phosphorylation of topo I is also referred to herein as "reference data". In some embodiments, the reference level of phospho-topo I is obtained from a control biological sample or a reference biological sample. In some embodiments, a reference biological sample comprises cells taken from the same subject or a different subject, for example a biological sample of a physiologically matched tissue can comprise non-cancerous cells. In some embodiments, a reference biological sample comprises cells taken from the same subject at an earlier timepoint (i.e. at a time point 0 or "$t_o$") and as such, a reference sample can be used as reference data which can be compared with the phosphorylation status of topo I in a biological sample taken from the same subject at one or more later timepoint (i.e. $t_1$, $t_2$, $t_3$, $t_4$ etc). In some embodiments, a reference biological sample comprises a physiologically matched tissue, or can comprise non-cancerous cells. Alternatively, a reference biological sample can be obtained from a control subject. In some embodiments, a reference biological sample is contacted with an protein-binding molecule capable of interactions with the topo I polypeptide to determine the phosphorylation status of topo I, such that the phosphorylation status of topo I in the reference biological sample can be compared with the levels of phosphorylation of topo I polypeptide in a biological sample from the subject using the kits, methods, machines, computer systems and media as disclosed herein. In some embodiments, where a biological sample from a subject has a greater level of phospho-topo I, such as a greater level of phospho-S10-topo I as compared to a reference biological sample, for example, if the level of phospho-topo I, such as phospho-S10-topo I in the subjects' biological sample is greater, for example at least about 0.5-fold, or at least about 1.0-fold, or 1.2-fold greater or at least 1.5 fold greater or at least two-fold more than the level of phospho-topo I, such as phospho-S10-topo I in the reference biological sample, the cancer is identified to be likely to be unresponsive to a topo I inhibitor.

In some embodiments, the methods as disclosed herein provide a diagnostic test for the activity of topo I inhibitors in the treatment of cancer, i.e. efficacy of a topo I inhibitor such as CPT to reduce cell viability. In one embodiment, a diagnostic test useful in the methods as disclosed herein detects the phosphorylation status of topo I, such as the presence of phospho-S10 topo I, and the presence of phospho-S10 topo I indicates that a topo I inhibitor is likely to be less effective in the treatment of cancer in a subject when compared to if there is lack of, or minimal presence of phospho-S10 topo I. Thus, in some embodiments, detection of high levels of phospho-S10 topo I in a biological sample comprising cancer cells from a subject can be used as a diagnostic to identify cancers which are likely to be non-responsive to a topo I inhibitor treatment. In related embodiments, the comparison of the phosphorylation status of topo I protein, such as phospho-S10 topo I to non-phosphorylated topo I or topo I polypeptide which is not phosphorylated on S10 amino acid residue can be determined between treated and untreated biopsy samples, cell lines, transgenic animals, or extracts from any of these, to determine the effect of a given treatment topo I inhibitor as compared to an untreated control.

Methods to Detect Phosphorylation of a topo I Polypeptide

In all aspects of the present invention, the phosphorylation status (i.e. degree of phosphorylation) of a topo I polypeptide can be determined by any means known by a person of ordinary skill in the art. In all aspects of the invention, the degree of phosphorylation can be determined using a protein-binding molecule or protein binding entity using standard methods known by one of ordinary skill in the art. One can use any protein-binding molecule, including for example but not limited to, antibody-based binding moieties and antibodies and fragment thereof, to determine the phosphorylation status of the topo I polypeptide, such as the presence of phosphorylated topo I (i.e. phospho-topo I) and/or the presence of phospho-S10 topo I polypeptide. Examples of protein-binding molecules include, but are not limited to immunoglobulin molecules and immunologically active determinants of immunoglobulin molecules, e.g., molecules that contain an antigen binding site which specifically binds (immunoreacts with) to the phosphorylated form of topo I, in particular the phospho-S10 topo I polypeptide. One can detect the presence of phospho-topo I, and in particular the presence of phospho-S10 topo I polypeptide by detecting a signal from the binding of a labeled protein-binding molecule specific for phospho-S10 topo I polypeptide.

In one embodiment, a protein-binding molecule or antibody-based binding moiety is detectably labeled by linking the antibody to an enzyme. The enzyme, in turn, when exposed to it's substrate, will react with the substrate in such a manner as to produce a chemical moiety which can be detected, for example, by spectrophotometric, fluorometric or by visual means. Enzymes which can be used to detectably label the antibodies of the present invention include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholinesterase.

Detection can also be accomplished using any of a variety of other immunoassays. For example, by radioactively labeling an antibody, it is possible to detect the antibody through the use of radioimmune assays. The radioactive isotope can be detected by such means as the use of a gamma counter or a scintillation counter or by audioradiography. Isotopes which are particularly useful for the purpose of the present invention are $^3H$, $^{131}I$, $^{35}S$, $^{14}C$, $^{32}P$, and preferably all isotopes of atoms in a phosphate group.

It is also possible to label an antibody with a fluorescent compound. When the fluorescently labeled antibody is exposed to light of the proper wavelength, its presence can then be detected due to fluorescence. Among the most commonly used fluorescent labeling compounds are CYE dyes, fluorescein isothiocyanate, rhodamine, phycoerytherin, phycocyanin, allophycocyanin, o-phthaldehyde and fluorescamine.

An antibody or protein-binding molecule can also be detectably labeled using fluorescence emitting metals such as 152Eu, or others of the lanthanide series. These metals can be attached to the antibody using such metal chelating groups as diethylenetriaminepentaacetic acid (DTPA) or ethylenediaminetetraacetic acid (EDTA). An antibody or protein-binding molecule also can be detectably labeled by coupling it to a chemiluminescent compound. The presence of the chemiluminescent-antibody is then determined by detecting the presence of luminescence that arises during the course of a chemical reaction. Examples of particularly useful chemiluminescent labeling compounds are luminol, luciferin, isoluminol, theromatic acridinium ester, imidazole, acridinium salt and oxalate ester.

Accordingly, in all aspects of the present invention, the phosphorylation status (i.e. degree of phosphorylation) of a topo I polypeptide can be determined can be using an to a protein-binding agent, also referred to herein as "protein-binding entity" or an "affinity reagent" can be used, in particular, antibodies. For instance, the affinity reagents, in particular, antibodies such as anti-phospho-S10 topo I antibodies can be used in an immunoassay, particularly in an ELISA (Enzyme Linked Immunosorbent Assay). In embodiments where the level of phospho topo I, such as level of phospho-S10 topo I can be measured in a biological sample using methods commonly known in the art, and include, for example but not limited to; isoform-specific chemical or enzymatic cleavage of isoform proteins, immunoblotting, immunohistochemical analysis, ELISA, and mass spectrometry.

As mentioned above, levels of phospho topo I, such as level of phospho-S10 topo I can be detected by immunoassays, such as enzyme linked immunoabsorbant assay (ELISA), radioimmunoassay (RIA), Immunoradiometric assay (IRMA), Western blotting, immunocytochemistry or immunohistochemistry, each of which are described in more detail below. Immunoassays such as ELISA or RIA, which can be extremely rapid, are more generally preferred. Antibody arrays or protein chips can also be employed, see for example U.S. Patent Application Nos: 20030013208A1; 20020155493A1; 20030017515 and U.S. Pat. Nos. 6,329, 209; 6,365,418, which are herein incorporated by reference in their entirety.

Immunoassays

The most common enzyme immunoassay is the "Enzyme-Linked Immunosorbent Assay (ELISA)." ELISA is a technique for detecting and measuring the concentration of an antigen using a labeled (e.g. enzyme linked) form of the antibody. There are different forms of ELISA, which are well known to those skilled in the art. The standard techniques known in the art for ELISA are described in "Methods in Immunodiagnosis", 2nd Edition, Rose and Bigazzi, eds. John Wiley & Sons, 1980; Campbell et al., "Methods and Immunology", W. A. Benjamin, Inc., 1964; and Oellerich, M. 1984, J. Clin. Chem. Clin. Biochem., 22:895-904.

In a "sandwich ELISA", an antibody (e.g. anti-enzyme) is linked to a solid phase (i.e. a microtiter plate) and exposed to a biological sample containing antigen (e.g. enzyme). The solid phase is then washed to remove unbound antigen. A labeled antibody (e.g. enzyme linked) is then bound to the bound-antigen (if present) forming an antibody-antigen-antibody sandwich. Examples of enzymes that can be linked to the antibody are alkaline phosphatase, horseradish peroxidase, luciferase, urease, and B-galactosidase. The enzyme linked antibody reacts with a substrate to generate a colored reaction product that can be measured.

In a "competitive ELISA", antibody is incubated with a sample containing antigen (i.e. enzyme). The antigen-antibody mixture is then contacted with a solid phase (e.g. a microtiter plate) that is coated with antigen (i.e., enzyme). The more antigen present in the sample, the less free antibody that will be available to bind to the solid phase. A labeled (e.g., enzyme linked) secondary antibody is then added to the solid phase to determine the amount of primary antibody bound to the solid phase.

In an "immunohistochemistry assay" a section of tissue is tested for specific proteins by exposing the tissue to antibodies that are specific for the protein that is being assayed. The antibodies are then visualized by any of a number of methods to determine the presence and amount of the protein present. Examples of methods used to visualize antibodies are, for example, through enzymes linked to the antibodies (e.g., luciferase, alkaline phosphatase, horseradish peroxidase, or beta-galactosidase), or chemical methods (e.g., DAB/Substrate chromagen). The sample is then analysed microscopically, most preferably by light microscopy of a sample stained with a stain that is detected in the visible spectrum, using any of a variety of such staining methods and reagents known to those skilled in the art.

Alternatively, "Radioimmunoassays" can be employed. A radioimmunoassay is a technique for detecting and measuring the concentration of an antigen using a labeled (e.g. radioactively or fluorescently labeled) form of the antigen. Examples of radioactive labels for antigens include 3H, 14C, and 125I. The concentration of antigen enzyme in a biological sample is measured by having the antigen in the biological sample compete with the labeled (e.g. radioactively) antigen for binding to an antibody to the antigen. To ensure competitive binding between the labeled antigen and the unlabeled antigen, the labeled antigen is present in a concentration sufficient to saturate the binding sites of the antibody. The higher the concentration of antigen in the sample, the lower the concentration of labeled antigen that will bind to the antibody.

In a radioimmunoassay, to determine the concentration of labeled antigen bound to antibody, the antigen-antibody complex must be separated from the free antigen. One method for separating the antigen-antibody complex from the free antigen is by precipitating the antigen-antibody complex with an anti-isotype antiserum. Another method for separating the antigen-antibody complex from the free antigen is by precipitating the antigen-antibody complex with formalin-killed S. aureus. Yet another method for separating the antigen-antibody complex from the free antigen is by performing a "solid-phase radioimmunoassay" where the antibody is linked (e.g., covalently) to Sepharose beads, polystyrene wells, polyvinylchloride wells, or microtiter wells. By comparing the concentration of labeled antigen bound to antibody to a standard curve based on samples having a known concentration of antigen, the concentration of antigen in the biological sample can be determined.

An "Immunoradiometric assay" (IRMA) is an immunoassay in which the antibody reagent is radioactively labeled. An IRMA requires the production of a multivalent antigen conjugate, by techniques such as conjugation to a protein e.g., rabbit serum albumin (RSA). The multivalent antigen conjugate must have at least 2 antigen residues per molecule and the antigen residues must be of sufficient distance apart to allow binding by at least two antibodies to the antigen. For example, in an IRMA the multivalent antigen conjugate can be attached to a solid surface such as a plastic sphere. Unlabeled "sample" antigen and antibody to antigen which is radioactively labeled are added to a test tube containing the multivalent antigen conjugate coated sphere. The antigen in the sample competes with the multivalent antigen conjugate for antigen antibody binding sites. After an appropriate incubation period, the unbound reactants are removed by washing and the amount of radioactivity on the solid phase is determined. The amount of bound radioactive antibody is inversely proportional to the concentration of antigen in the sample.

Other techniques can be used to detect the phosphorylation status of topo I, in particular to detect the presence of phospho-S10 topo I polypeptide in a biological sample can be performed according to a practitioner's preference, and based upon the present disclosure and the type of biological sample (i.e. plasma, urine, tissue sample etc). One such technique is Western blotting (Towbin et at, Proc. Nat. Acad. Sci. 76:4350 (1979)), wherein a suitably treated sample is run on an SDS-PAGE gel before being transferred to a solid support, such as a nitrocellulose filter. Detectably labeled anti-phospho S10 antibodies or protein binding molecules can then be used to assess the phosphorylation status of topo I, where the intensity of the signal from the detectable label corresponds to the amount of phosphorylation of topo I. Levels of the amount of phosphorylation of topo I and the amount of the total topo I polypeptide present can also be quantified, for example by densitometry.

In one embodiment, the phosphorylation status of topo I, in particular the phosphorylation status of S10 residue on the topo I polypeptide in a biological sample can be determined by mass spectrometry such as MALDI/TOF (time-of-flight), SELDI/TOF, liquid chromatography-mass spectrometry (LC-MS), gas chromatography-mass spectrometry (GC-MS), high performance liquid chromatography-mass spectrometry (HPLC-MS), capillary electrophoresis-mass spectrometry, nuclear magnetic resonance spectrometry, or tandem mass spectrometry (e.g., MS/MS, MS/MS/MS, ESI-MS/MS, etc.). See for example, U.S. Patent Application Nos: 20030199001, 20030134304, 20030077616, which are herein incorporated by reference.

In particular embodiments, these methodologies can be combined with the machines, computer systems and media to produce an automated system for determining the presence of phospho-topo I, and in particular phospho-S10 topo I in a biological sample and analysis to produce a printable report which identifies at least one of the following: (i) the level of phospho-S10 topo I in a biological sample (ii) the presence of phospho-S10 topo I in a biological sample, (iii) the % or ratio of phospho-S10 topo I: non-phosphorylated S10 topo I, (iv) the % chance a subject is likely to be non-responsive to treatment with a topo I inhibitor, (v) the % chance a subject is likely to be responsive to treatment with a topo I inhibitor, (vi) a positive indication a subject is likely to be responsive to a topo I inhibitor, or (vii) an indication a subject is likely to be unresponsive to a topo I inhibitor.

Mass spectrometry methods are well known in the art and have been used to quantify and/or identify biomolecules, such as proteins (see, e.g., Li et al. (2000) Tibtech 18:151-160; Rowley et al. (2000) Methods 20: 383-397; and Kuster and Mann (1998) Curr. Opin. Structural Biol. 8: 393-400). Further, mass spectrometric techniques have been developed that permit at least partial de novo sequencing of isolated proteins. Chait et al., Science 262:89-92 (1993); Keough et al., Proc. Natl. Acad. Sci. USA. 96:7131-6 (1999); reviewed in Bergman, EXS 88:133-44 (2000).

In certain embodiments, a gas phase ion spectrophotometer is used. In other embodiments, laser-desorption/ionization mass spectrometry is used to analyze the sample. Modern laser desorption/ionization mass spectrometry ("LDI-MS") can be practiced in two main variations: matrix assisted laser desorption/ionization ("MALDI") mass spectrometry and surface-enhanced laser desorption/ionization ("SELDI"). In MALDI, the analyte is mixed with a solution containing a matrix, and a drop of the liquid is placed on the surface of a substrate. The matrix solution then co-crystallizes with the biological molecules. The substrate is inserted into the mass spectrometer. Laser energy is directed to the substrate surface where it desorbs and ionizes the biological molecules without significantly fragmenting them. See, e.g., U.S. Pat. No. 5,118,937 (Hillenkamp et al.), and U.S. Pat. No. 5,045,694 (Beavis & Chait) which are incorporated herein by reference.

In SELDI, the substrate surface is modified so that it is an active participant in the desorption process. In one variant, the surface is derivatized with adsorbent and/or capture reagents that selectively bind the protein of interest. In another variant, the surface is derivatized with energy absorbing molecules that are not desorbed when struck with the laser. In another variant, the surface is derivatized with molecules that bind the protein of interest and that contain a photolytic bond that is broken upon application of the laser. In each of these methods, the derivatizing agent generally is localized to a specific location on the substrate surface where the sample is applied. See, e.g., U.S. Pat. No. 5,719,060 and WO 98/59361 which are incorporated herein by reference. The two methods can be combined by, for example, using a SELDI affinity surface to capture an analyte and adding matrix-containing liquid to the captured analyte to provide the energy absorbing material.

For additional information regarding mass spectrometers, see, e.g., Principles of Instrumental Analysis, 3rd edition, Skoog, Saunders College Publishing, Philadelphia, 1985; and Kirk-Othmer Encyclopedia of Chemical Technology, 4.sup.th ed. Vol. 15 (John Wiley & Sons, New York 1995), pp. 1071-1094.

Detection of the presence or level of phospho-topo I, and in particular phospho-S10 topo I will typically depend on the detection of signal intensity. This, in turn, can reflect the quantity and character of a polypeptide bound to the substrate. For example, in certain embodiments, the signal strength of peak values from spectra of a first sample and a second sample can be compared (e.g., visually, by computer analysis etc.), to determine the relative amounts of particular biomolecules. Software programs such as the Biomarker Wizard program (Ciphergen Biosystems, Inc., Fremont, Calif.) can be used to aid in analyzing mass spectra. The mass spectrometers and their techniques are well known to those of skill in the art.

In some embodiment of this aspect and all aspects disclosed herein, a biological sample can be monitored using radioactive labeling, in particular, to an inverse radioactive labeling, preferably with iodine isotopes. Preferably, an inverse radioactive labeling is performed using $^{125}I$ and $^{131}I$ isotopes. In another embodiment, a subject, for example a human subject can be subjected to a radioactive labeling, in particular, to an inverse radioactive labeling, preferably with iodine isotopes, such as but not limited to $^{125}$I and $^{131}$I isotopes.

In all aspects of the present invention, the phosphorylation status (i.e. degree of phosphorylation) of a topo I polypeptide can be determined based on gel electrophoresis techniques, in particular SDS-PAGE (Sodium Dodecylsulfate Polyacrylamide Gel Elektrophoresis), especially two dimensional PAGE (2D-PAGE), preferably two dimensional SDS-PAGE (2D-SDS-PAGE). According to a particular example, the assay is based on 2D-PAGE, in particular, using immobilized pH gradients (IPGs) with a pH range preferably over pH 4-9.

In all aspects of the present invention, the phosphorylation status (i.e. degree of phosphorylation) of a topo I polypeptide can be determined can be using gel electrophoresis techniques, in particular, the above mentioned techniques may be combined with other protein separation methods, particularly methods known to those skilled in the art, in particular, chromatography and/or size exclusion. In all aspects of the present invention, the phosphorylation status (i.e. degree of phosphorylation) of a topo I polypeptide can be determined, if appropriate, using a combination of any of the above mentioned methods with a combination of detection methods which are well known to those skilled in the art, such as, but not limited to antibody detection and/or mass spectrometry.

Since the difference between non-responsiveness and responsiveness to topoisomerase inhibitors is due to the phosphorylation or non-phosphorylation of topo I polypeptide respectively, thus all methods enabling the detection of subtle or extreme differences in the stoichiometry of phosphate or oxygen atoms in proteins are within the scope of this disclosure. In this regard, in some aspects of the present invention, methods of elemental analysis, measurement of the state of ionization or differential electrical conductivity are useful and are encompassed within the scope of this disclosure. According to a further example, methods enabling the measurement of differences in the degradation rate of a topoisomerase I polypeptide, as well as stable isotope content of proteins, in particular, of chemically modified proteins, or degradation products thereof are also encompassed as part of this disclosure.

In a further embodiment of all aspects of the present invention, the phosphorylation status (i.e. degree of phosphorylation) of a topo I polypeptide can be determined can be using mass spectrometry as disclose herein in the Examples, and in particular, MALDI (Matrix Assisted Laser Desorption/Ionization) and/or SELDI (Surface enhanced Laser Desorption/Ionization). In an alternative embodiment, resonance techniques, in particular, plasma surface resonance, can be used.

In some cases, it may be advantageous to achieve a separation of a topoisomerase I proteins from a heterogeneous population of proteins in a biological sample for example using a means of one of the above outlined methods before cleaving the proteins. Such a cleavage step can be performed by applying enzymes, chemicals or other suitable reagents which are known to those skilled in the art. In an alternative embodiment, one may perform a cleavage step and subsequent separation of the cleaved topoisomerase I polypeptide fragments, in particular, followed by, for example, measurements of topo I polypeptide concerning its abundance and/or degree of phosphorylation using any one of the methods, kits, machines, computer systems or media as disclosed herein. In some embodiments of this aspect of the invention, the cleaved topoisomerase I polypeptide fragments can be labeled and, optionally separated where the protein spots which correspond to cleaved topoisomerase I polypeptide fragments can be visualized by imaging techniques, for instance using the PROTEP TOPO® imaging technique.

In some embodiments, a protein-binding agents or antibodies or useful in the methods as disclosed herein bind or have affinity for phosphorylated topo I polypeptide, in particular to phosphorylation on serine 10 residue of topo I polypeptide.

In some embodiments, protein-binding moieties such as antibodies can be utilized to detect the presence of phosphorylation of topo I polypeptide by itself (i.e. individually), or when the topo I polypeptide exists in complex with other polypeptides, for example when topo I is complexed with any, or a combination of polypeptides which triggers its degradation by the ubiquitination pathway, for example, DNA-PK, BRAC1 and/or BRAC1/BARD1 complex. Additionally, in other embodiments, protein-binding moieties such as antibodies can be utilized to detect the presence of phosphorylation of topo I polypeptide when it is post-translationally modified, for example when topo I polypeptide is ubiquitinated. In some embodiments, protein binding moieties such as antibodies can bind to topo I proteins individually or in a complex, and in some embodiments a protein-binding moiety such as an antibody can be labeled with a detectable label.

In some embodiments, antibodies and protein-binding molecules are labeled. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin.

In all aspects of the present invention, the phosphorylation status of topo I polypeptide can be determined by using immunological techniques using a phospho-topo I antibody, such as an anti-phospho-topoI-S10 antibody using common methods known by a person of ordinary skill in the art, e.g., antibody techniques such as immunohistochemistry, immunocytochemistry, FACS scanning, immunoblotting, radioimmunoassays, western blotting, immunoprecipitation, enzyme-linked immunosorbant assays (ELISA), and derivative techniques that make use of antibodies directed against phosphorylated topo I, such as a phospho-topo I antibody or anti-phospho-topoI-S10 antibody.

Any method to detect topo I protein phosphorylation known by a person of ordinary skill in the art are useful in the methods, kits, machines and computer systems and media as disclosed herein to detect the level of phosphorylation, such as the level of phosphorylation of serine 10 of topo I protein. For example, immunohistochemistry ("IHC") and immunocytochemistry ("ICC") techniques can be used. IHC is the application of immunochemistry to tissue sections, whereas ICC is the application of immunochemistry to cells or tissue imprints after they have undergone specific cytological preparations such as, for example, liquid-based preparations. Immunochemistry is a family of techniques based on the use of a specific antibody, wherein antibodies are used to specifically target molecules inside or on the surface of cells. The antibody typically contains a marker that will undergo a biochemical reaction, and thereby experience a change color, upon encountering the targeted molecules. In some instances, signal amplification may be integrated into the particular protocol, wherein a secondary antibody, that includes the marker stain, follows the application of a primary specific antibody.

Immunohistochemical assays are well known to those of skill in the art (e.g., see Jalkanen, et al., J. Cell. Biol. 101: 976-985 (1985); Jalkanen, et al., J. Cell. Biol. 105:3087-3096 (1987).

In some embodiments, antibodies, polyclonal, monoclonal and chimeric antibodies useful in the methods as disclosed herein can be purchased from a variety of commercial suppliers, or may be manufactured using well-known methods, e.g., as described in Harlow et al., Antibodies: A Laboratory Manual, 2nd Ed; Cold. Spring Harbor Laboratory Press, Cold Spring Harbor, N.Y. (1988). In general, examples of antibodies useful in the present invention include anti-serine antibodies. Such antibodies can be purchased, for example, from Sigma-Aldrich, CalBiochem, Abcam, Santa-Cruz Biotechnology, novus Bio, U.S. biologicals, Millipore, LifeSpan, Abnova, CellSignalling etc.

Typically, for immunohistochemistry, tissue obtained from a subject and fixed by a suitable fixing agent such as alcohol, acetone, and paraformaldehyde, is sectioned and reacted with an antibody. Conventional methods for immunohistochemistry are described in Harlow and Lane (Eds) (1988) In "Antibodies A Laboratory Manual", Cold Spring Harbor Press, Cold Spring Harbor, New York; Ausbel et al (Eds) (1987), in Current Protocols In Molecular Biology, John Wiley and Sons (New York, N.Y.). Biological samples appropriate for such detection assays include, but are not limited to, cells, tissue biopsy, whole blood, plasma, serum, sputum, cerebrospinal fluid, breast aspirates, pleural fluid, urine and the like.

In some embodiments, direct labeling techniques can be used, where a labeled antibody is utilized. For indirect labeling techniques, the sample is further reacted with a labeled substance.

In some embodiments, immunocytochemistry may be utilized where, in general, tissue or cells are obtained from a subject are fixed by a suitable fixing agent such as alcohol, acetone, and paraformaldehyde, to which is reacted an antibody. Methods of immunocytological staining of human samples is known to those of skill in the art and described, for example, in Brauer et al., 2001 (FASEB J, 15, 2689-2701), Smith Swintosky et al., 1997.

Immunological methods are particularly useful in the methods as disclosed herein, because they require only small quantities of biological material, and are easily performed and at multiple different locations. In some embodiments, such an immunological method useful in the methods as disclosed herein uses a "lab-on-a-chip" device, involving a single device to run a single or multiple biological samples and requires minimal reagents and apparatus and is easily performed, making the "lab-on-a-chip" devices which detect the phosphorylation status, in particular the phosphorylation status of S10 residue of a topo I protein is ideal for rapid, on-site diagnostic tests to identify if a biological sample obtained from a subject is likely to be responsive to a topo I inhibitor. In some embodiments, the immunological methods can be done at the cellular level and thereby necessitate a minimum of one cell. Preferably, several cells are obtained from a subject affected with or at risk for developing cancer and assayed using the methods, kits, machines, computer systems and media as disclosed herein.

Antibodies useful in the methods as disclosed herein to detect the level of phosphorylation of topo I, such as phosphorylation at S10 of topo I (herein referred to as an "anti-phospho-topo I S10 antibody") can be polyclonal, monoclonal, chimeric antibodies, humanized antibodies, tribodies, midibodies, recombinant antibodies and any antibody, or fragment thereof, commonly known by persons of ordinary skill in the art. In some embodiments, an intact antibody, or a fragment thereof (e.g., Fab or F(ab)$_2$) can be used. Antibodies reactive to, or bind specifically to phosphorylated topo I, in particular the topo I protein which is phosphorylated on serine S10 residue be readily raised in animals such as rabbits or mice by immunization with an antigenic fragment of topo I as discussed in more detail below. In some embodiments, an antigenic fragment of topo I useful to generate phospho-topo I antibodies and/or phospho-topo I S10 antibodies comprise the peptide of SEQ ID NO: 1. Immunized mice are particularly useful for providing sources of B cells for the manufacture of hybridomas, which in turn are cultured to produce large quantities of monoclonal antibodies.

In one embodiment of this invention, the inhibitor to the gene products identified herein can be an antibody molecule or the epitope-binding moiety of an antibody molecule and the like. Antibodies provide high binding avidity and unique specificity to a wide range of target antigens and haptens. Monoclonal antibodies useful in the practice of the present invention include whole antibody and fragments thereof and are generated in accordance with conventional techniques, such as hybridoma synthesis, recombinant DNA techniques and protein synthesis.

Useful monoclonal antibodies and fragments can be derived from any species (including humans) or can be formed as chimeric proteins which employ sequences from more than one species. Human monoclonal antibodies or "humanized" murine antibody are also used in accordance with the present invention. For example, murine monoclonal antibody can be "humanized" by genetically recombining the nucleotide sequence encoding the murine Fv region (i.e., containing the antigen binding sites) or the complementarily determining regions thereof with the nucleotide sequence encoding a human constant domain region and an Fc region. Humanized targeting moieties are recognized to decrease the immunoreactivity of the antibody or polypeptide in the host recipient, permitting an increase in the half-life and a reduction the possibly of adverse immune reactions in a manner similar to that disclosed in European Patent Application No. 0,411,893 A2. The murine monoclonal antibodies should preferably be employed in humanized form. Antigen binding activity is determined by the sequences and conformation of the amino acids of the six complementarily determining regions (CDRs) that are located (three each) on the light and heavy chains of the variable portion (Fv) of the antibody. The 25-kDa single-chain Fv (scFv) molecule, composed of a variable region (VL) of the light chain and a variable region (VH) of the heavy chain joined via a short peptide spacer sequence, is the smallest antibody fragment developed to date. Techniques have been developed to display scFv molecules on the surface of filamentous phage that contain the gene for the scFv. scFv molecules with a broad range of antigenic-specificities can be present in a single large pool of scFv-phage library. Some examples of high affinity monoclonal antibodies and chimeric derivatives thereof, useful in the methods of the present invention, are described in the European Patent Application EP 186,833; PCT Patent Application WO 92/16553; and U.S. Pat. No. 6,090,923, which are incorporated herein in their entirety by reference.

Chimeric antibodies are immunoglobin molecules characterized by two or more segments or portions derived from different animal species. Generally, the variable region of the chimeric antibody is derived from a non-human mammalian antibody, such as murine monoclonal antibody, and the immunoglobin constant region is derived from a human immunoglobin molecule. Preferably, both regions and the combination have low immunogenicity as routinely determined.

One limitation of scFv molecules is their monovalent interaction with target antigen. One of the easiest methods of improving the binding of a scFv to its target antigen is to increase its functional affinity through the creation of a multimer. Association of identical scFv molecules to form diabodies, triabodies and tetrabodies can comprise a number of identical Fv modules. These reagents are therefore multivalent, but monospecific. The association of two different scFv molecules, each comprising a VH and VL domain derived from different parent Ig will form a fully functional bispecific diabody. A unique application of bispecific scFvs is to bind two sites simultaneously on the same target molecule via two (adjacent) surface epitopes. These reagents gain a significant avidity advantage over a single scFv or Fab fragments. A number of multivalent scFv-based structures has been engineered, including for example, miniantibodies, dimeric miniantibodies, minibodies, (scFv)$_2$, diabodies and triabodies. These molecules span a range of valence (two to four binding sites), size (50 to 120 kDa), flexibility and ease of production. Single chain Fv antibody fragments (scFvs) are predominantly monomeric when the VH and VL domains are joined by, polypeptide linkers of at least 12 residues. The monomer scFv is thermodynamically stable with linkers of 12 and 25 amino acids length under all conditions. The noncovalent diabody and triabody molecules are easy to engineer and are produced by shortening the peptide linker that connects the variable heavy and variable light chains of a single scFv molecule. The scFv dimers are joined by amphipathic helices that offer a high degree of flexibility and the miniantibody structure can be modified to create a dimeric bispecific (DiBi) miniantibody that contains two miniantibodies (four scFv molecules) connected via a double helix. Gene-fused or disulfide bonded scFv dimers provide an intermediate degree of flexibility and are generated by straightforward cloning techniques adding a C-terminal Gly4Cys sequence. scFv-CH3 minibodies are comprised of two scFv molecules joined to an IgG CH3 domain either directly (LD minibody) or via a very flexible hinge region (Flex minibody). With a molecular weight of approximately 80 kDa, these divalent constructs are capable of significant binding to antigens. The Flex minibody exhibits impressive tumor localization in mice. Bi- and trispecific multimers can be formed by association of different scFv molecules. Increase in functional affinity can be reached when Fab or single chain Fv antibody fragments (scFv) fragments are complexed into dimers, trimers or larger aggregates. The most important advantage of multivalent scFvs over monovalent scFv and Fab fragments is the gain in functional binding affinity (avidity) to target antigens. High avidity requires that scFv multimers are capable of binding simultaneously to separate target antigens. The gain in functional affinity for scFv diabodies compared to scFv monomers is significant and is seen primarily in reduced off-rates, which result from multiple binding to two or more target antigens and to rebinding when one Fv dissociates. When such scFv molecules associate into multimers, they can be designed with either high avidity to a single target antigen or with multiple specificities to different target antigens. Multiple binding to antigens is dependent on correct alignment and orientation in the Fv modules. For full avidity in multivalent scFvs target, the antigen binding sites must point towards the same direction. If multiple binding is not sterically possible then apparent gains in functional affinity are likely to be due the effect of increased rebinding, which is dependent on diffusion rates and antigen concentration. Antibodies conjugated with moieties that improve their properties are also contemplated for the instant invention. For example, antibody conjugates with PEG that increases their half-life in vivo can be used for the present invention. Immune libraries are prepared by subjecting the genes encoding variable antibody fragments from the B lymphocytes of naive or immunized animals or patients to PCR amplification. Combinations of oligonucleotides which are specific for immunoglobulin genes or for the immunoglobulin gene families are used. Immunoglobulin germ line genes can be used to prepare semisynthetic antibody repertoires, with the complementarity-determining region of the variable fragments being amplified by PCR using degenerate primers. These single-pot libraries have the advantage that antibody fragments against a large number of antigens can be isolated from one single library. The phage-display technique can be used to increase the affinity of antibody fragments, with new libraries being prepared from already existing antibody fragments by random, codon-based or site-directed mutagenesis, by shuffling the chains of individual domains with those of fragments from naive repertoires or by using bacterial mutator strains.

Alternatively, a SCID-hu mouse, for example the model developed by Genpharm, can be used to produce antibodies, or fragments thereof. In one embodiment, a new type of high avidity binding molecule, termed peptabody, created by harnessing the effect of multivalent interaction is contemplated. A short peptide ligand was fused via a semirigid hinge region with the coiled-coil assembly domain of the cartilage oligomeric matrix protein, resulting in a pentameric multivalent binding molecule. In some embodiments, proteins-binding agents can be targeted to tissue- or tumor-specific targets by using bispecific antibodies, for example produced by chemical linkage of an anti-ligand antibody (Ab) and an Ab directed toward a specific target. To avoid the limitations of chemical conjugates, molecular conjugates of antibodies can be used for production of recombinant bispecific single-chain Abs directing ligands and/or chimeric inhibitors at cell surface molecules. Alternatively in some embodiments, two or more protein-binding molecules can be administered, for example in some embodiments a protein binding molecule can be an antibody that is conjugated to another a different antibody. Each antibody is reactive with a different target site epitope (associated with the same or a different target site antigen). The different antibodies with the agents attached accumulate additively at the desired target site. Antibody-based or non-antibody-based targeting moieties can be employed to deliver a ligand or the inhibitor to a target site. Preferably, a natural binding agent for an unregulated or disease associated antigen is used for this purpose.

Anti-phospho-topo I S10 Antibodies.

In all aspects of the present invention, the methods, kits, machines and computer systems and media can use anti-phospho-S10-topo I antibodies to detect the phosphorylation status of topo I, in particular to detect the presence of phospho-S10 topo I polypeptide. Suitable anti-phospho-S10-topo I antibodies, include, but are not limited to polyclonal antibodies, monoclonal antibodies, chimeric antibodies, humanized antibodies, human antibodies, single chain antibodies and Fab fragments.

Anti-phospho-topo I S10 antibodies can be prepared from antigenic fragments of the topo I polypeptide comprising the serine 10 residue. Typically an antigenic polypeptide contains at least about 5, and preferably at least about 10 or more amino acids. In one embodiment, an antigenic polypeptide useful in the generation of an anti-phospho-S10 topo I antibody is MSGDHLHND(pS)QIEADFR (SEQ ID NO: 1), where the Serine is phosphorylated (pS). In another embodiment, an antigenic polypeptide useful in the generation of an anti-phospho-S10 topo I antibody is ND(pS)QIEAD-FRLNDC (SEQ ID NO: 4), where the Serine is phosphorylated (pS). The anti-phospho-S10 topo I antibody used in the examples was generated using the phosphorylated peptide of SEQ ID NO: 4.

Methods for the generation of suitable antibodies will be readily appreciated by those skilled in the art. For example, a suitable monoclonal antibody, typically containing Fab portions, may be prepared using the hybridoma technology described in Antibodies—A Laboratory Manual Harlow and Lane, Eds. Cold Spring Harbor Laboratory, N.Y. (1988), the disclosure of which is incorporated herein by reference.

Similarly, there are various procedures known in the art which may be used for the production of polyclonal antibodies to polypeptides of interest as disclosed herein. For the production of polyclonal antibodies, various host animals, including but not limited to rabbit mice, rats, sheep, goats, etc, can be immunized by injection with a polypeptide, or fragment or analogue thereof. Further, the polypeptide or fragment or analogue thereof can be conjugated to an immunogenic carrier, e.g., bovine serum albumin (BSA) or keyhole limpet hemocyanin (KLH). Also, various adjuvants may be used to increase the immunological response, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacillus Calmette-Guerin) and *Corynebacterium parvum*.

Screening of a candidate anti-phospho-S10-topo I antibody which binds to with specific affinity to topo I polypeptide that is phosphorylated on the serine 10 residue can also be accomplished by a variety of techniques known in the art. For example, such assays for immunospecific binding of antibodies include, but are not limited to, radioimmunoassays, ELISAs (enzyme-linked immunosorbent assay), sandwich immunoassays, immunoradiometric assays, gel diffusion precipitation reactions, immunodiffusion assays, in situ immunoassays, Western blots, precipitation reactions, agglutination assays, complement fixation assays, immunofluorescence assays, protein A assays, and Immunoelectrophoresis assays, and the like (see, for example, Ausubel et al., eds, 1994, Current Protocols in Molecular Biology, Vol. 1, John Wiley & Sons, Inc., New York). Antibody binding of a candidate anti-phospho-S10-topo I antibody can be detected by virtue of a detectable label on the primary antibody. Alternatively, an anti-phospho-S10-topo I primary antibody can be detected by virtue of its binding with a secondary antibody or reagent which is appropriately labeled. Numerous methods are known by persons of ordinary skill in the art to detecting binding in an immunoassay and are within the scope of the present invention.

Biological Sample

Accordingly in one embodiment of this aspect and all other aspects described herein, a biological sample as defined herein can include a human biological sample, preferably a microdissected human samples, are derived from a small tissue fraction, particularly from a tumor tissue fraction. In some embodiments, the tissue tumor fraction is from SCLC, colon or ovarian cancer, or from a refractory cancer, including but not limited to a breast or cervical cancer tissue fraction. In some embodiments, the human samples are preferably harvested by biopsy and/or surgical extraction, and in some embodiments, the human sample can be stored, for example as frozen biological sample prior to subjecting to the detection of phosphorylation status of topo I polypeptide using the methods, kits, machines, computer systems and media as disclosed herein.

In some embodiments, the biological sample is treated after it is obtained from a subject to "fix" the phosphorylation status of phospho-S10 topo I polypeptide, such that there is not a change in phosphorylation status (i.e. a dephosphorylation or increase in phosphorylation) of topo I polypeptude from the time the tissue (i.e. biological sample) was harvested from the subject and the time it is analysed by the methods, kits, machines, computer systems and computer readable media as disclosed herein. In some embodiments, this is important, because phosphorylation status can rapidly alter (i.e. dephosphoryle or phosphorylate) if the phosphorylation status is not stable after removal of a biological sample or tissue from a subject, thus dephosphorylation may increase or phosphorylation may increase leading to inaccuracies (i.e. false positives or false negatives) in the detection and analysis as disclosed herein. Accordingly, in some embodiments, a biological sample, such as tissue biopsy is optionally treated to "fix" the phosphorylation status of topoI polypeptide before the biological sample is subject to analysis by the methods, kits, machines, computer systems and computer readable media as disclosed herein. Methods to fix a biological sample, such as a tissue biopsy are well known by a skilled artisan, and include formaldehyde, formalin, FAA fixative and other fixatives and methods commonly known by a skilled artisan.

Topoisomerase I Inhibitors

In some embodiments of all aspect of the invention described herein, a topo I inhibitor is any agent which substantially decreases the biological activity of the topo I polypeptide in vitro, in vivo or ex vivo. Exemplary topo I inhibitors are, for example but not limited to camptothecin (CTP) and analogues thereof including but not limited to irinotecan and topotecan, and derivatives thereof.

In one aspect of the present invention, topoisomerase I inhibitors can be any topoisomerase I inhibitor commonly known by persons of ordinary skill in the art. For example, Camptothecin (CPT) represents the most extensively studied mammalian topoisomerase I inhibitor. See R. C. Gallo et al., J. Natl. Cancer Inst., 46, 789 (1971) and B. C. Giovanella et al., Cancer Res., 51 3052 (1991). The broad spectrum of potent antineoplastic activity observed for camptothecin has prompted further efforts to identify other agents which can effectively poison mammalian topoisomerase I. For instance camptothecin analogues are disclosed in U.S. Pat. Nos. 5,364, 858, 5,106,742, 5,468,754; 5,604,233; 5,674,873; which are incorporated herein in their entirety by reference.

Camptothecin is a pentacyclic alkaloid initially isolated from the wood and bark of Camptotheca acuminata by Wall et al (M. E. Wall, M. C. Wani, C. E. Cook, K. H. Palmer, A. T. McPhail, and G. A. Sim, J. Am. Chem. Soc., 94, 388 (1966). Camptothecin is highly biologically active and displays strong inhibitory activity toward the biosynthesis of nucleic acids. Additionally, camptothecin exhibits potent anti-tumor activity against experimentally transplanted carcinoma such as leukemia L-1210 in mice or Walker 256 tumor in rats. Several methods for the synthesis of camptothecin and camptothecin analogs are known. These synthetic methods include (i) methods in which naturally occurring camptothecin is synthetically modified to produce a number of analogs and (ii) totally synthetic methods. U.S. Pat. Nos. 4,604,463; 4,545,880; and 4,473,692, which are incorporated herein by reference, as well as European Patent Application 0074256 are examples of the former type of synthetic strategy. Additional examples of this strategy can be found in Japanese Patents 84/46,284; 84/51,287; and 82/116,015. These methods required naturally occurring camptothecin which is difficult to isolate and hence these methods are not suitable for the production of large quantities of camptothecin or analogs.

Examples of a variety of totally synthetic routes to camptothecin and camptothecin analogs can be found in the following references: Sci. Sin. (Engl. Ed), 21(1), 87-98 (1978); Fitoterpapia, 45(3), 87-101 (1974); Yakugaku Zashi, 92(6), 743-6 (1972); J. Org. Chem., 40(14), 2140-1 (1975); Hua Hsueh Hsueh Pao, 39(2), 171-8 (1981); J. Chem. Soc., Perkin Trans 1, (5), 1563-8 (1981); Heterocycles, 14(7), 951-3 (1980); J. Amer. Chem. Soc., 94(10), 3631-2 (1972); J. Chem. Soc. D, (7), 404 (1970) and U.S. Pat. No. 4,031,098, which is incorporated herein in its entirety by reference. Wani et al, J. Med. Chem., 23, 554 (1980) discloses a synthesis of camptothecin and camptothecin analogs which involves the reaction of a tricyclic compound with a suitably substituted orthoaminoaldehyde to yield desoxycamptothecin. Desoxycamptothecin is then treated with oxygen to give camptothecin analogs.

Camptothecin and camptothecin analogs are agents that target and inhibit the intranuclear enzyme topoisomerase I. Camptothecin includes but is not limited to 20 (S)-camptothecin, an analog of 20 (S)-camptothecin, a derivative of 20 (S)-camptothecin, a predrug of 20 (S)-camptothecin or pharmaceutical active metabolites thereof, are collectively referred to herein as CPT.

According to any one of the aspects of the invention as disclosed herein, CPT may be 20 (S)-camptothecin or any analog or derivative of 20 (S)-camptothecin. Examples of 20 (S)-camptothecin analogs include, but are not limited to 9-nitro-20 (S)-camptothecin and 9-amino-20 (S)-camptothecin. Examples of 20 (S)-camptothecin derivatives include, but are not limited to 9-methyl-camptothecin, 9-chloro-camptothecin, 9-fluoro-camptothecin, 7-ethyl camptothecin, 10-methyl-camptothecin, 10-chloro-camptothecin, 10-bromo-camptothecin, 10-fluoro-camptothecin, 9-methoxy-camptothecin, 11-fluoro-camptothecin, 7-ethyl-10-hydroxy camptothecin, 10,11-methylenedioxy camptothecin, 10,11-ethylenedioxy camptothecin, 7-(4-methylpiperazinomethylene)-10,11-methylenedioxy camptothecin, camptothecin 20-0-propionate, camptothecin 20-0-butyrate, camptothecin 20-O-valerate, camptothecin 20-O-heptanoate, camptothecin 20-O-nonanoate, camptothecin 20-O-crotonate, camptothecin 20-0-2',3'-epoxy-butyrate, nitrocamptothecin 20-0-acetate, nitrocamptothecin 20-0-propionate, and nitrocamptothecin 20-0-butyrate.

"Camptothecin", as it is referred to in the present invention, includes the plant alkaloid 20 (S)-camptothecin, water insoluble or soluble analogs and derivatives of 20 (S)-camptothecin, prodrugs of camptothecin, and metabolites of 20 (S)-camptothecin. Examples of camptothecin derivatives include, but are not limited to, 9-nitro-20 (S)-camptothecin, 9-amino-20 (S)-camptothecin, 9-methyl-camptothecin, 9-chloro-camptothecin, 9-fluoro-camptothecin, 7-ethyl camptothecin, 10-methyl-camptothecin, 10-chloro-camptothecin, 10-bromo-camptothecin, 10-fluoro-camptothecin, 9-methoxy-camptothecin, 11-fluoro-camptothecin, 7-ethyl-10-hydroxy camptothecin, 10,11-methylenedioxy camptothecin, and 10,11-ethylenedioxy camptothecin, and 7-(4-methylpiperazinomethylene)-10,11-methylenedioxy camptothecin.

Prodrugs of camptothecin include, but are not limited to, esterified camptothecin derivatives as described in U.S. Pat. No. 5,731,316, such as camptothecin 20-0-propionate, camptothecin 20-0-butyrate, camptothecin 20-O-valerate, camptothecin 20-O-heptanoate, camptothecin 20-O-nonanoate, camptothecin 20-0-crotonate, camptothecin 20-0-2',3'-epoxy-butyrate, nitrocamptothecin 20-O-acetate, nitrocamptothecin 20-0-propionate, and nitrocamptothecin 20-0-butyrate.

Native, unsubstituted, camptothecin can be obtained by purification of the natural extract, or may be obtained from the Stehlin Foundation for Cancer Research (Houston, Tex.). Substituted camptothecins can be obtained using methods known in the literature, or can be obtained from commercial suppliers. For example, 9-nitro-camptothecin may be obtained from SuperGen, Inc. (San Ramon, Calif.), and 9-amino-camptothecin may be obtained from Idec Pharmaceuticals (San Diego, Calif.). Camptothecin and various of its analogs and derivatives may also be obtained from standard fine chemical supply houses, such as Sigma Chemicals.

Camptothecin and camptothecin derivatives useful in all aspect described herein can be modified for optimal delivery. For instance, for optimal delivery methods camptothecin and camptothecin derivatives can be conjugated to any molecule, for example, IT 101 is a conjugate of CYCLOSERT™, and the potent anti-cancer compound camptothecin, which is disclosed in U.S. Pat. No. 7,270,808, which is incorporated herein in its entirety by reference. TOCOSOL Camptothecin is a camptothecin compound that is a conjugate of SN-38. SN-38 is the active ingredient in irinotecan, a camptothecin analog. Preclinical data suggest that TOCOSOL Camptothecin may be more effective and better tolerated than irinotecan, and will be easier and more convenient to administer. TOCOSOL camptothecin is disclosed in U.S. Pat. No. 7,223,770 which is incorporated herein in its entirety by reference.

Second-generation camptothecin derivatives have been optimized for improved water solubility to facilitate intravenous drug administration. Highlights resulting from various programs at different companies and institutions are irinotecan 2 and topotecan 3, two compounds which are successfully used in clinical practice, and SN-38 4, exatecan 5, liposomal lurtotecan 6 (OSI-211) and CKD-602 7, which are in advanced stages of clinical development. The chemical structures of these compounds are shown in FIGS. 1A and 1B of U.S. Patent Application US20080280935, which is incorporated herein in its entirety by reference.

SN-38 is a camptothecin derivative that contains a hydroxyl group at the C10 position and an ethyl group at the C7 position. Irinotecan is a camptothecin derivative (it may also be viewed as a derivative of SN-38) that contains a sidechain at the C10 position and an ethyl group at the C7 position. Irinotecan was discovered at Yakult Honsha and was first approved in Japan in 1994 (CAMPTOTESIN®) for lung, cervical and ovarian cancer. Today it is marketed in the U.S. by Pharmacia (CAMPTOSAR®) and by Aventis in Europe (CAMPTO®). Irinotecan is a prodrug which is cleaved in vivo by carboxylic esterases, particularly by hCE-2, to release the active metabolite SN-38.

The synthesis of irinotecan has been described in the chemical literature and in patents. A common approach to the synthesis of irinotecan is to form SN-38 and then add a sidechain to the C10 position of SN-38, to thereby form irinotecan. U.S. Pat. No. 4,604,463, which is incorporated herein by reference in its entirety, is one example of a patent that describes this approach, wherein either an activated form of the sidechain is separately formed and then reacted with SN-38, or the C10 hydroxyl group is activated and then in a separate reaction the sidechain is added. Another method to synthesis of irinotecan has been described in U.S. Patent Application US20080280935, which is incorporated herein in its entirety by reference.

Topotecan topoisomerase I inhibitor can be produced as described in U.S. Pat. No. 6,660,861, which is incorporated herein by reference. Other topoisomerase I inhibitors can be used, for example, Hoechst 33342 (1), 2'-(4-ethoxyphenyl)-5-(4-methyl-1-piperazinyl)-2,5'-bi-1H-benzimidazole is an inhibitor of topoisomerase I, and is disclosed in U.S. Pat. No. 5,807,874 which is incorporated herein in its entirety by reference.

Topotecan, a semisynthetic analog of camptothecin, was shown to inhibit both acute and chronic HIV-1 infections in vitro. J. L. Zhang, et al. "Topoisomerase inhibits human immunodeficiency virus type 1 infection through a topisomerase-independent mechanism in a cell line with altered topoisomerase I" Antimicrob. Agents Chemother. 41: 977-981 (1997). The antiviral effects of topotecan were observed not only in the topoisomerase-mutated CPT-K5 cell line but also in peripheral blood mononuclear cells (PBMC) acutely infected with clinical isolates and in OM10.1 cells latently infected with HIV and activated by tumor necrosis factor alpha (TNF-a). It was again hypothesized that this camptothecin targets factors in virus replication other than cellular topoisomerase I and inhibits cytokine-mediated activation in latently infected cells by means other than cytotoxicity.

Other topo I inhibitors include, for example, but not limited to, antibodies (polyclonal or monoclonal), neutralizing antibodies, antibody fragments, peptides, proteins, peptide-mimetics, aptamers, oligonucleotides, hormones, small molecules, nucleic acids, nucleic acid analogues, carbohydrates or variants thereof that function to inactivate the nucleic acid and/or protein of the gene products identified herein, and those as yet unidentified. Nucleic acids include, for example but not limited to, DNA, RNA, oligonucleotides, peptide nucleic acid (PNA), pseudo-complementary-PNA (pcPNA), locked nucleic acid (LNA), RNAi, microRNAi, siRNA, shRNA etc. Topo I inhibitors can also be chemicals, small molecules, chemical entities, nucleic acid sequences, nucleic acid analogues or protein or polypeptide or analogue or fragment thereof. In some embodiments, a nucleic acid topo I inhibitor is DNA or RNA, and nucleic acid analogues, for example can be PNA, pcPNA and LNA. A nucleic acid topo I inhibitor can be single or double stranded, and can be selected from a group comprising; nucleic acid encoding a protein of interest, oligonucleotides, PNA, etc. Such nucleic acid sequences include, for example, but not limited to, nucleic acid sequence encoding proteins that act as transcriptional repressors, antisense molecules, ribozymes, small inhibitory nucleic acid sequences, for example but not limited to RNAi, shRNAi, siRNA, micro RNAi (mRNAi), antisense oligonucleotides etc.

Alternatively, a topo I inhibitor can be a protein and/or peptide topo I inhibitor or fragment thereof. For example, topo I inhibitor can be, for example but not limited to mutated proteins; therapeutic proteins and recombinant proteins. Proteins and peptides inhibitors can also include for example; mutated proteins, genetically modified proteins, peptides, synthetic peptides, recombinant proteins, chimeric proteins, antibodies, humanized proteins, humanized antibodies, human antibodies, single chain antibodies and Fab fragments, chimeric antibodies, modified proteins and fragments thereof.

In some embodiments, a topo I inhibitor is a nucleic acid, nucleic acid analogues, peptides, phage, phagemids, polypeptides, peptidomimetics, ribosomes, aptamers, antibodies, small or large organic or inorganic molecules, or any combination thereof.

Methods to Treat a Subject Identified to be Responsive to a TopoI Inhibitor.

Exemplarily examples of topo I inhibitors are for example but not limited to, camptothecin (CTP) and analogues thereof including but not limited to irinotecan and topotecan, and derivatives thereof disclosed in the section entitled "topo I inhibitors" herein.

Another aspect of the present invention relates to increasing the efficacy of topoisomerase I inhibitors. For example, in one such an aspect and all other aspects described herein, where a biological sample has been determined to have a positive phosphorylation status of the topo I polypeptide (i.e. the biological sample comprises phosphorylation of topoisomerase I protein), in particular where the biological sample has been determined to have phosphorylation of S10 residue of topo I polypeptide using the methods, kits, machines, computer systems and media as disclosed herein, a subject from which the biological sample was obtained can be administered an agent which decreases the phosphorylation of topo I, for example the subject can be administered an agent which dephosphorylates S10 of the topo I polypeptide concurrently with the administration of a topo I inhibitor. In some embodiments, an agent which dephosphorylates topo I, such as an agent which dephosphorylates S10 of topo I can be administered prior to, concurrent with, or subsequent to the administration of a topo I inhibitor as that term is defined herein.

Accordingly, another aspect of the present invention relates to administering to a subject an agent which increases the sensitivity (i.e. decreases the non-responsiveness) of a tumor cell to a topoisomerase I inhibitor, where an agent which increases the sensitivity to a topo I inhibitor (i.e. a topo I inhibitor sensitivity agent) is for example an agent which results in the dephosphorylation of topo I, preferably the dephosphorylation of S10 of topo I. Such methods are particularly useful when a subject has been identified to likely to be non-responsive to a topoisomerase I inhibitor using the methods, kits, machines, computer systems and media as disclosed herein. As discussed above, a topo I inhibitor which can be administered subsequent to, concurrent with or prior to administration of an agent which results in the dephosphorylation of topo I, preferably the dephosphorylation of S10 of topo I is camptothecin (CPT), or CTP analogues such as topotecan and irinotecan and derivatives thereof, including but not limited CPT compounds, CPT metabolites, derivatives or analogues thereof having a skeleton similar to CPT.

Those skilled in the art will appreciate that a topo I inhibitor to which the present invention refers are not limited to the above-mentioned specific agents but include any compound or entity that functions as a topo I inhibitor, i.e. any agent which decreases the biological activity of the topo I polypeptide.

Antagonists or Inhibitor Agents of DNA-PK

In some embodiments of this aspect of the invention which relates to increasing the efficacy of topoisomerase I inhibitors, an agent which increases the sensitivity (i.e. decreases the non-responsiveness and is referred to herein as a topo I inhibitor sensitivity agent) of a tumor cell to a topoisomerase I inhibitor is an anti-phospho-S10 topo I antibody. In an alternative embodiment, a topo I inhibitor sensitivity agent is an inhibitor of the kinase DNA-PK. In some embodiments, an inhibitor of the kinase DNA-PK is NU7026, 2-morpholin-4-yl)-benzo[h]chromen-4-one, or derivatives or analogues thereof, as disclosed herein in the examples. Other examples of such inhibitors of DNA-PK include those disclosed in U.S. Pat. Nos. 7,402,607, 7,226,918, and in U.S. Applications US2007/238729, US2004/192687, US2008,0242664, US2008/0038277, US2007/0167441 and US2009/0035394 which are all incorporated herein in their entirety by reference. Other examples of such inhibitors of DNA-PK include, for example, but not limited to, antibodies (polyclonal or monoclonal), neutralizing antibodies, antibody fragments, peptides, proteins, peptide-mimetics, aptamers, oligonucleotides, hormones, small molecules, nucleic acids, nucleic acid analogues, carbohydrates or variants thereof that function to inactivate the nucleic acid and/or protein of the gene products identified herein, and those as yet unidentified. Nucleic acids include, for example but not limited to, DNA, RNA, oligonucleotides, peptide nucleic acid (PNA), pseudo-complementary-PNA (pcPNA), locked nucleic acid (LNA), RNAi, microRNAi, siRNA, shRNA etc. The inhibitors can be selected from a group of a chemical, small molecule, chemical entity, nucleic acid sequences, nucleic acid analogues or protein or polypeptide or analogue or fragment thereof. In some embodiments, the nucleic acid is DNA or RNA, and nucleic acid analogues, for example can be PNA, pcPNA and LNA. A nucleic acid may be single or double stranded, and can be selected from a group comprising; nucleic acid encoding a protein of interest, oligonucleotides, PNA, etc. Such nucleic acid sequences include, for example, but not limited to, nucleic acid sequence encoding proteins that act as transcriptional repressors, antisense molecules, ribozymes, small inhibitory nucleic acid sequences, for example but not limited to RNAi, shRNAi, siRNA, micro RNAi (mRNAi), antisense oligonucleotides etc. A protein and/or peptide inhibitor or fragment thereof, can be, for example, but not limited to mutated proteins; therapeutic proteins and recombinant proteins. Proteins and peptides inhibitors can also include for example; mutated proteins, genetically modified proteins, peptides, synthetic peptides, recombinant proteins, chimeric proteins, antibodies, humanized proteins, humanized antibodies, chimeric antibodies, modified proteins and fragments thereof.

Accordingly, in some embodiments of this aspect and all other aspects described herein, a topo I inhibitor is administered in combination with an agent which increases the sensitivity of a cell to said topo I inhibitor, wherein in one embodiment an agent is an agent which increases dephosphorylation of topo I polypeptide, such as decreases phosphorylation at serine 10 of topo I polypeptide, and in an alternative embodiment, the agent is an agent which inhibits the biological activity of DNA-PK, thus inhibiting phosphorylation of topo I by DNA-PK. In some embodiments, inhibition of DNA-PK can occur via inhibition of nucleic acid transcripts encoding DNA-PK, for example inhibition of messenger RNA (mRNA). In alternative embodiments, inhibition of DNA-PK is inhibition of the expression and/or inhibition of activity of the gene product of DNA-PK, for example the polypeptide or protein of DNA-PK. As used herein, the term "gene product" refers to RNA transcribed from a gene, or a polypeptide encoded by a gene or translated from RNA.

In some embodiments, inhibition of DNA-PK is by an agent. One can use any agent, for example but are not limited to nucleic acids, nucleic acid analogues, peptides, phage, phagemids, polypeptides, peptidomimetics, ribosomes, aptamers, antibodies, small or large organic or inorganic molecules, or any combination thereof. In some embodiments, agents useful in methods of the present invention include agents that function as inhibitors of DNA-PK, for example inhibitors of mRNA encoding DNA-PK.

Agents useful in the methods as disclosed herein can also inhibit gene expression (i.e. suppress and/or repress the expression of the gene). Such agents are referred to in the art as "gene silencers" and are commonly known to those of ordinary skill in the art. Examples include, but are not limited to a nucleic acid sequence, for an RNA, DNA or nucleic acid analogue, and can be single or double stranded, and can be selected from a group comprising nucleic acid encoding a protein of interest, oligonucleotides, nucleic acids, nucleic acid analogues, for example but are not limited to peptide nucleic acid (PNA), pseudo-complementary PNA (pc-PNA), locked nucleic acids (LNA) and derivatives thereof etc. Nucleic acid agents also include, for example, but are not limited to nucleic acid sequences encoding proteins that act as transcriptional repressors, antisense molecules, ribozymes, small inhibitory nucleic acid sequences, for example but are not limited to RNAi, shRNAi, siRNA, micro RNAi (miRNA), antisense oligonucleotides, etc.

As used herein, agents useful in the method as inhibitors of DNA-PK can be any type of entity, for example but are not limited to chemicals, nucleic acid sequences, nucleic acid analogues, proteins, peptides or fragments thereof. In some embodiments, the agent is any chemical, entity or moiety, including without limitation, synthetic and naturally-occurring non-proteinaceous entities. In certain embodiments the agent is a small molecule having a chemical moiety. For example, in some embodiments, the chemical moiety is a pyrimidione-based compound as disclosed herein.

In alternative embodiments, agents useful in the methods as disclosed herein are proteins and/or peptides or fragment thereof, which inhibit the gene expression of DNA-PK or the function of the DNA-PK protein. Such agents include, for example but are not limited to protein variants, mutated proteins, therapeutic proteins, truncated proteins and protein fragments. Protein agents can also be selected from a group comprising mutated proteins, genetically engineered proteins, peptides, synthetic peptides, recombinant proteins, chimeric proteins, antibodies, midibodies, minibodies, triabodies, humanized proteins, humanized antibodies, chimeric antibodies, modified proteins and fragments thereof.

Alternatively, agents useful in the methods as disclosed herein as inhibitors of DNA-PK can be a chemicals, small molecule, large molecule or entity or moiety, including without limitation synthetic and naturally-occurring non-proteinaceous entities. In certain embodiments the agent is a small molecule having the chemical moieties as disclosed herein.

In particular embodiments the antagonist is a nucleic-acid based inhibitor of expression of polynucleotide encoding DNA-PK or fragments thereof. Suitable molecules include small interfering RNA (siRNA) species, antisense constructs, such as antisense oligonucleotides, and catalytic antisense nucleic acid constructs. Suitable molecules can be manufactured by chemical synthesis, recombinant DNA procedures or, in the case of antisense RNAi by transcription in vitro or in vivo when linked to a promoter, by methods known to those skilled in the art.

One suitable technology for inhibiting gene expression, known as RNA interference (RNAi), (see, e.g. Chuang et al. (2000) PNAS USA 97: 4985) may be used for the purposes of the present invention, according to known methods in the art (for example Fire et al. (1998) Nature 391: 806-811; Hammond, et al. (2001) Nature Rev, Genet. 2: 110-1119; Hammond et al. (2000) Nature 404:293-296; Bernstein et al. (2001) Nature 409: 363-366; Elbashir et al (2001) Nature 411: 494-498; WO 99/49029 and WO 01/70949, the disclosures of which are incorporated herein by reference), to inhibit the expression of DNA-PK. RNAi refers to a means of selective post-transcriptional gene silencing by destruction of specific mRNA by small interfering RNA molecules (siRNA). The siRNA is typically generated by cleavage of double stranded RNA, where one strand is identical to the message to be inactivated. Double-stranded RNA molecules may be synthesized in which one strand is identical to a specific region of the mRNA transcript of DNA-PK and introduced directly. Alternatively corresponding double stranded DNA (dsDNA) can be employed, which can be converted into dsRNA. Methods for the synthesis of suitable siRNA molecules for use in RNAi and for achieving post-transcriptional gene silencing are known to those of skill in the art. Those skilled in the art will also appreciate that a range of suitable siRNA constructs capable of inhibiting the expression of DNA-PK can be identified and generated based on knowledge of the sequence of the gene in question using routine procedures known to those skilled in the art without undue experimentation.

The isolated inhibitory nucleic acid construct comprising a nucleic acid sequence specific to a least a portion of the polynucleotide encoding DNA-PK, wherein the nucleic acid construct substantially inhibits the expression of DNA-PK in tumor cells. Alternatively, inhibitory nucleic acid constructs may comprise of a nucleic acid sequences specific to at least a portion of a polynucleotide encoding one or more genes which regulate the expression of DNA-PK. Genes that regulate the expression of DNA-PK comprise, for example, but not limited to, transcription factors, co-activators, activators, enhancers and cofactors of DNA-PK.

Those skilled in the art will appreciate that there need not necessarily be 100% nucleotide sequence match between the target sequence and the siRNA sequence. The capacity for mismatch there between is dependent largely on the location of the mismatch within the sequences.

In particular embodiments of the invention suitable inhibitory nucleic acid molecules may be administered to the tumor cells in a vector. The vector may be a plasmid vector, a viral vector, or any other suitable vehicle adapted for the insertion and foreign sequence and for the introduction into eukaryotic cells. The vector can be an expression vector capable of directing the transcription of the DNA sequence of inhibitory nucleic acid molecules into RNA. Viral expression vectors can be selected from a group comprising, for example, reteroviruses, lentiviruses, Epstein Barr virus-, bovine papilloma virus, adenovirus- and adeno-associated-based vectors or hybrid virus of any of the above. In one embodiment, the vector is episomal. The use of a suitable episomal vector provides a means of maintaining the inhibitory nucleic add molecule in the tumor cells in high copy number extra chromosomal DNA thereby eliminating potential effects of chromosomal integration.

A further means of substantially inhibiting the expression of DNA-PK may be achieved by introducing catalytic antisense nucleic acid constructs, such as ribozymes, which are capable of cleaving RNA transcripts and thereby preventing the production of wildtype protein. Ribozymes are targeted to and anneal with a particular sequence by virtue of two regions of sequence complementary to the target flanking the ribozyme catalytic site. After binding the ribozyme cleaves the target in a site specific manner. The design and testing of ribozymes which specifically recognize and cleave sequences of isoforms of DNA-PK can be achieved by techniques well known to those in the art (for example Lleber and Strauss, (1995) Mol Cell Biol 15:540.551, the disclosure of which is incorporated herein by reference).

Alternative antagonists of DNA-PK may include antibodies. Suitable antibodies include, but are not limited to polyclonal antibodies, monoclonal antibodies, chimeric antibodies, humanized antibodies, human antibodies, single chain antibodies and Fab fragments.

Antibodies may be prepared from discrete regions of fragments of the polypeptide of interest. An antigenic polypeptide contains at least about 5, and preferably at least about 10 amino acids.

Methods for the generation of suitable antibodies will be readily appreciated by those skilled in the art. For example, a suitable monoclonal antibody, typically containing Fab portions, may be prepared using the hybridoma technology described in Antibodies—A Laboratory Manual Harlow and Lane, Eds. Cold Spring Harbor Laboratory, N.Y. (1988), the disclosure of which is incorporated herein by reference.

Similarly, there are various procedures known in the art which may be used for the production of polyclonal antibodies to polypeptides of interest as disclosed herein. For the production of polyclonal antibodies, various host animals, including but not limited to rabbit mice, rats, sheep, goats, etc, can be immunized by injection with a polypeptide, or fragment or analogue thereof. Further, the polypeptide or fragment or analogue thereof can be conjugated to an immunogenic carrier, e.g., bovine serum albumin (BSA) or keyhole limpet hemocyanin (KLH). Also, various adjuvants may be used to increase the immunological response, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacillus Calmette-Guerin) and *Corynebacterium parvum*.

Screening for the desired antibody can also be accomplished by a variety of techniques known in the art. Assays for immunospecific binding of antibodies may include, but are not limited to, radioimmunoassays, ELISAs (enzyme-linked immunosorbent assay), sandwich immunoassays, immunoradiometric assays, gel diffusion precipitation reactions, immunodiffusion assays, in situ immunoassays, Western blots, precipitation reactions, agglutination assays, complement fixation assays, immunofluorescence assays, protein A assays, and Immunoelectrophoresis assays, and the like (see, for example, Ausubel et al., eds, 1994, Current Protocols in Molecular Biology, Vol. 1, John Wiley & Sons, Inc., New York). Antibody binding may be detected by virtue of a detectable label on the primary antibody. Alternatively, the primary antibody may be detected by virtue of its binding with a secondary antibody or reagent which is appropriately labeled. Numerous methods are known by persons of ordinary skill in the art to detecting binding in an immunoassay and are within the scope of the present invention.

Also included within the scope of the present invention are alternative forms to inhibit the expression of DNA-PK, including, for example, small molecule or other non-nucleic acid or non-proteinaceous inhibitors. Such inhibitors may be identified by those skilled in the art by screening using routine techniques.

Automated Methods to Determine of the Phosphorylation Status of Topo I Using Machines, Computer Systems and Computer Readable Media.

In all aspects of the invention, methods to determine the phosphorylation status of topo I, in particular the presence of phospho-S10-topo I polypeptide can be performed using an automated machine or system. Such machines and systems generate a report, such as displaying a report on a visible screen or a printable report which indicates the phosphorylation status of topo I, such as the presence or absence of phospho-S10-topo I polypeptide in a biological sample and report of the biological sample is likely to be unresponsive or responsive to a topo I inhibitor respectively.

Accordingly, some embodiments of the invention also provide for a machine, computer systems and computer readable media for performing the steps of (i) determining the phosphorylation status of topo I, in particular the presence of phospho-S10-topo I polypeptide and (ii) indicating or reporting whether a subject has a likelihood of being responsive to a topo I inhibitor, and thus prognostic indicator if a topo I inhibitor is likely to be effective the treatment of cancer in the subject.

Embodiments of this aspect of the present invention are described through functional modules, which are defined by computer executable instructions recorded on computer readable media and which cause a computer to perform method steps when executed. The modules have been segregated by function for the sake of clarity. However, it should be understood that the modules need not correspond to discreet blocks of code and the described functions can be carried out by the execution of various code portions stored on various media and executed at various times. Furthermore, it should be appreciated that the modules may perform other functions, thus the modules are not limited to having any particular functions or set of functions.

Data Processing Systems:

One aspect of the present invention and all other aspect described herein, a machine can be used to determine phosphorylation status of topo I polypeptides in a biological sample, for example, a machine for obtaining data regarding a biological sample from a subject comprising: a biological sample container to hold the biological sample; a determination module configured to detect the presence of phosphorylation of a topoisomerase I polypeptide, for example the detection of phospho-S10 topo I in the biological sample which produces output data, in some embodiments the output data in a computer readable media format; a storage device configured to store the output data from the determination module; a comparison module adapted to compare the output data from the determination module with data stored on the storage device, such as stored reference data and control data, and a display module for displaying a page of retrieved content for the user on a client computer, wherein (i) the retrieved content is the presence of topoisomerase I polypeptide, and/or (ii) the retrieved content is the presence or absence of phosphorylation of the topoisomerase I polypeptide, for example the retrieved content is the presence or absence of phospho-S10 topo I and/or (iii) the retrieved content is the absence of phosphorylation of topoisomerase I, for example the absence of phospho-S10 topo I, which is a signal that the subject likely to be responsive to topoisomerase I inhibitor; and/or (iv) the retrieved content is the presence of phosphorylation of topoisomerase I, such as the presence of phospho-S10 topo I polypeptide which is a signal that the subject likely to be unresponsive to topoisomerase I inhibitor.

Computer Systems:

One aspect of the present invention is a computer system that can be used to determine if a subject is responsive to a topo I inhibitor. In such an embodiment, a computer system is connected to a determination module and is configured to obtain output data from a determination module regarding a biological specimen, where a determination module is configured to detect the presence of phosphorylation of a topoisomerase I polypeptide, for example the presence of phospho-S10 topo I polypeptide within a subject or in a biological sample obtained from the subject; and where the computer system comprises (a) a storage device configured to store data output from the determination module as well as reference data; where the storage device is connected to (b) a comparison module which in one embodiment, is adapted to compare the output data stored on the storage device with stored reference data, and in alternative embodiments, adapted to compare the output data with itself, where the comparison module produces report data and is connected to (c) a display module for displaying a page of retrieved content (i.e. report data from the comparison module) for the user on a client computer, wherein the retrieved content comprises any one or a combination of the following; (i) the presence or absence of phosphorylation of the topoisomerase I polypeptide, for example the retrieved content is the presence or absence of phospho-S10 topo I; (ii) the absence of phosphorylation of topoisomerase I, for example the absence of phospho-S10 topo I, (iii) the presence of phosphorylation of topoisomerase I, such as the presence of phospho-S10 topo I polypeptide, (iv) a positive test result (i.e. a positive phosphorylation status such as positive S10 topo I phosphorylation status) which indicates that the subject is likely to be more unresponsive to a topoI inhibitor than a subject having a cancer with a negative phosphorylation status, (v) a negative test result (i.e. a negative phosphorylation status such a negative S10 topo I phosphorylation status) which indicates that the subject is likely to be more responsive to a topoI inhibitor than a subject having a cancer with a positive phosphorylation.

In some embodiments the comparison module compares the output data stored on the storage device with itself or stored reference data, and calculates a positive S10 topo I phosphorylation status (i.e. the presence of phospho-S10 topo I polypeptide) which indicates a positive test result and generates report data to indicate that the subject is likely to be more unresponsive to a topoI inhibitor than a subject having a cancer with a negative phosphorylation status, where the report data from the comparison module is retrieved from the display module and displayed on the display module.

One aspect of the present invention and all other aspect described herein, one can use a computer readable media to determine phosphorylation status of topo I polypeptides from a subject having or at risk of having cancer, for example, a computer readable media having computer readable instructions recorded thereon to define software modules including a determination module and a comparison module for implementing a method on a computer, said method comprising: a storage device configured to store data reference data and output data from a determination module which has measured the presence or absence of the phosphorylation of topo I polypeptide, such as the presence or absence of phospho-S10 topo I polypeptide; a comparison module which generates report data, where the comparison module is adapted to compare the data stored on the storage device, for example a comparison of output data from the determination module with itself or alternatively with reference data, and a display module for displaying a page of retrieved content which is the report data from the comparison module for the user on a client computer, wherein the retrieved content comprises any one or a combination of the following; (i) the presence or absence of phosphorylation of the topoisomerase I polypeptide, for example the retrieved content is the presence or absence of phospho-S10 topo I; (ii) the absence of phosphorylation of topoisomerase I, for example the absence of phospho-S10 topo I, (iii) the presence of phosphorylation of topoisomerase I, such as the presence of phospho-S10 topo I polypeptide, (iv) a positive test result (i.e. a positive phosphorylation status such as positive S10 topo I phosphorylation status) which indicates that the subject is likely to be more unresponsive to a topoI inhibitor than a subject having a cancer with a negative phosphorylation status, (v) a negative test result (i.e. a negative phosphorylation status such a negative S10 topo I phosphorylation status) which indicates that the subject is likely to be more responsive to a topoI inhibitor than a subject having a cancer with a positive phosphorylation.

In some embodiments of this aspect and all other aspects of the present invention, a function module of embodiments of the invention include a determination module, a storage device, a comparison module and a display module. The modules can be executed on one, or multiple, computers, or by using one, or multiple, computer networks.

In some embodiments of this aspect and all other aspects of the present invention, the present invention therefore provides for automated machines, computer systems and computer readable media for performing methods of determining whether a subject is likely to be responsive to an topo I inhibitor based on the phosphorylation status of topo I, in particular the presence of phospho-S10 topo I polypeptide which would indicate that a topo I inhibitor is likely to lack efficacy in a subject (i.e. the subject is likely unresponsive to a topo I inhibitor) expression profiles or sequence information.

Figure 15:
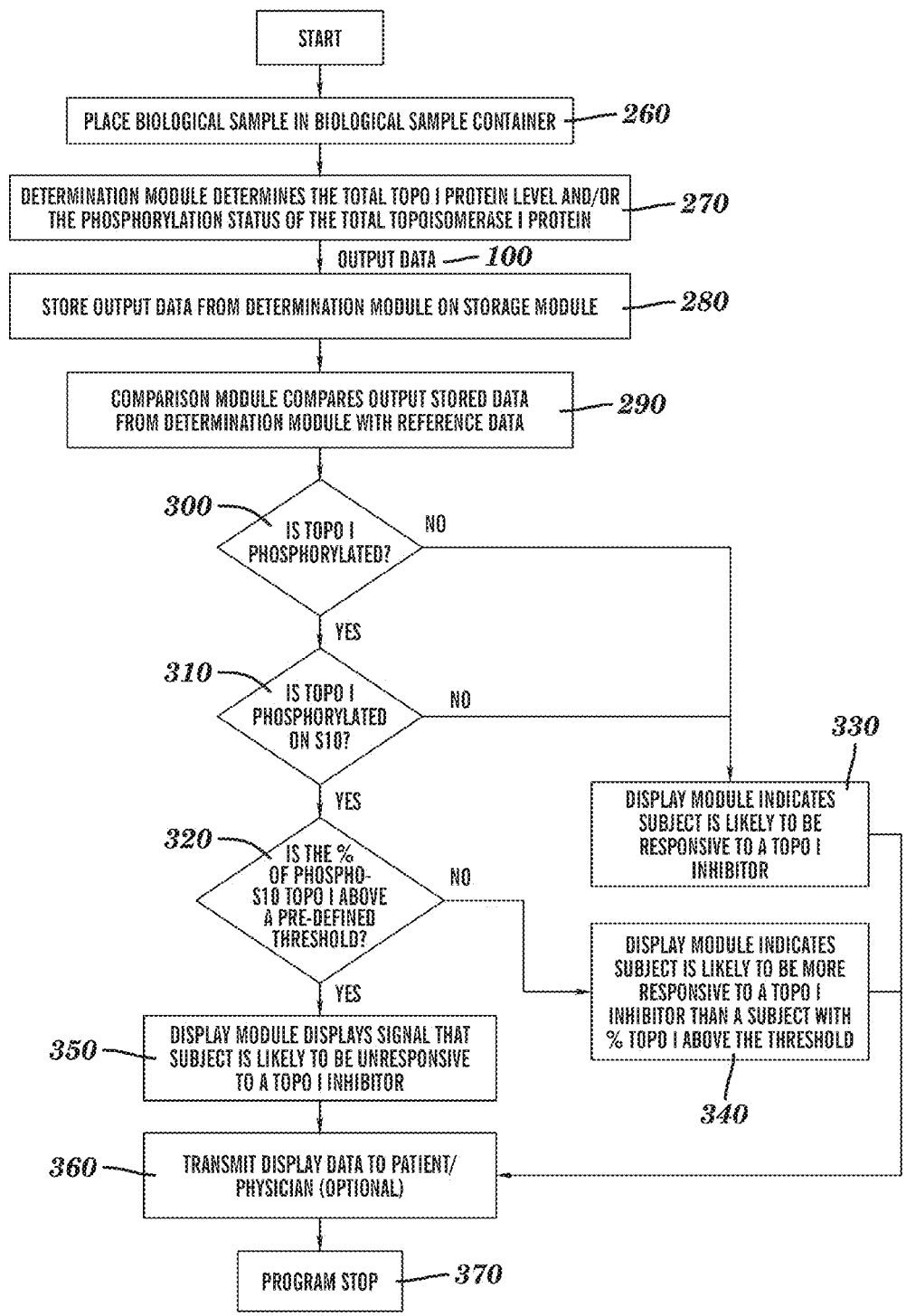
FIG. 15 shows a flow chart of a instructions for analyzing if a subject is responsive to a topo I inhibitor.
Figure 16:
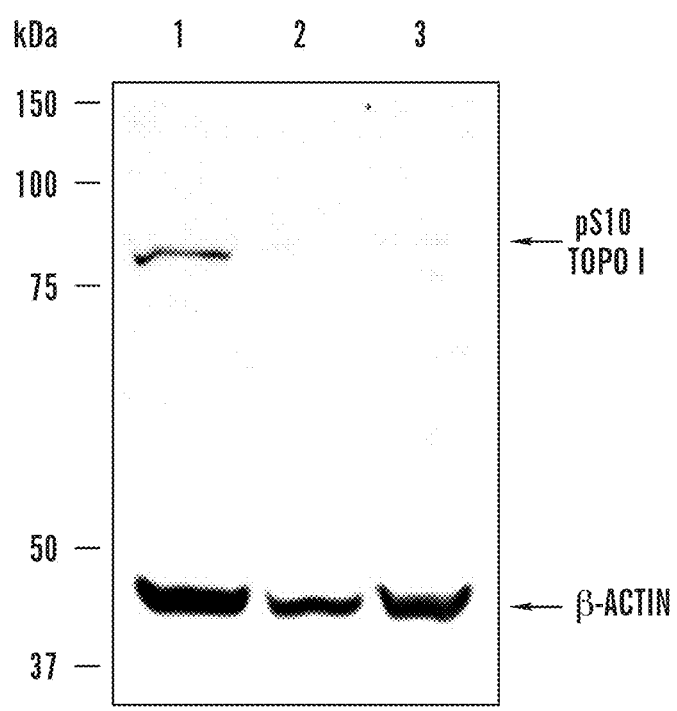
FIG. 16 shows a higher level of S10 topoI phosphorylation in CPT resistant cells.

Computer system 150, and computer readable medium shown in FIG. 15, are merely an illustrative embodiments of the invention for performing methods of determining whether a subject will likely be responsive to a topo I inhibitor based on the protein phosphorylation profile of topo I, in particular the % of phospho-S10 topo I protein as compared to total topo I protein level, and is not intended to limit the scope of the invention. Variations of computer systems, and computer readable medium, are possible and are intended to fall within the scope of the invention.

The modules of the machine, or used in the computer readable medium, may assume numerous configurations. For example, function may be provided on a single machine or distributed over multiple machines.

Figure 12:
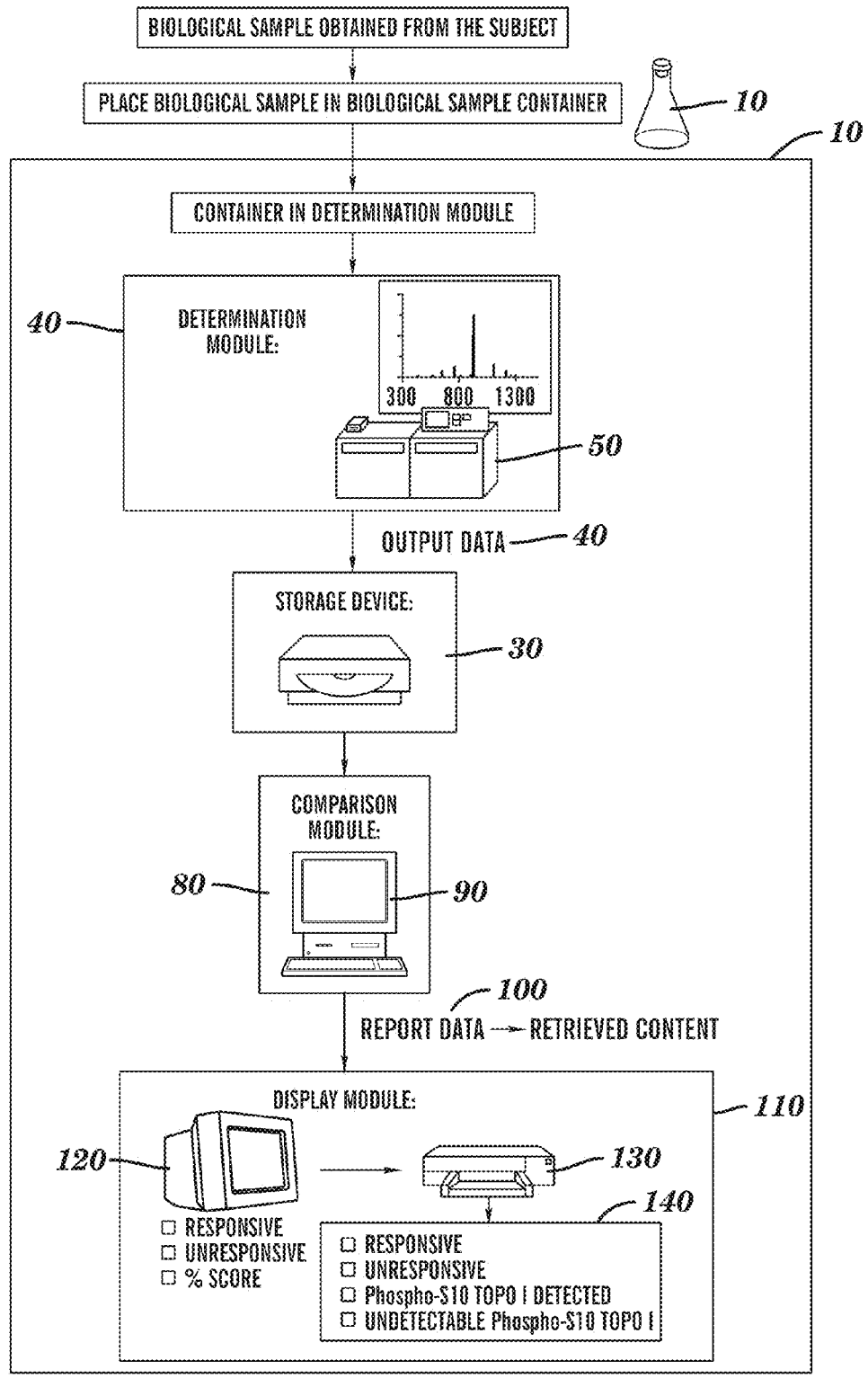
FIG. 12, shows a simplified block diagram of an embodiment of the present invention which relates to a machine for determining if a subject is responsive to a topo I inhibitor.

Referring now to the drawings, FIG. 12 depicts a block diagram of a machine 10 for determining if a subject is responsive to a topo I inhibitor according to an embodiment of the invention. The biological sample 20 is obtained from the subject, and placed into a biological sample container 30. The container 30 is placed in the determination module 40, where the determination module is a means for measuring and determining the phosphorylation status of topo I, for example but not limited to using mass spectrometry 50 or another means such as an immuno-detection means, for example using a protein binding molecule such as, but not limited to an anti-phospho-S10 topo I antibody. In some embodiments, a means to determine the phosphorylation status of topo I, for example the presence or level of phospho-S10 topo I is by an antibody array comprising a protein-binding molecules such as but not limited to anti-topo I antibodies and anti-phospho-S10 topo I antibodies. In some embodiments, the determination module 40 also determines the total level of topo I polypeptide (i.e. the combined total of phosphorylated and non-phosphorylated topo I protein level). The output data 60 is stored in the storage module 70, which can also comprise reference data. A comparison module 80 comprises computer readable media 90 such as a comparison software program or algorithm to compare the level of phosphorylation of S10 of topo I with the stored reference data, and in some embodiments the comparison module 80 calculates the % of phospho-S10 topo I protein in the biological sample from the total amount of topo I protein. The comparison module 80 produces report data 105, which is retrieved as retrieved content 100 which is displayed by a display module 110, which is a means to display the retrieved content 100 from the comparison module 80. In some embodiments, the display module 110 can be a computer screen 120, or a report 140 printed from a printer 130. The display module 110 can also be include displays 120, printers 130, speakers, cathode ray tubes (CRTs), plasma displays, light-emitting diode (LED) displays, liquid crystal displays (LCDs), printers, vacuum florescent displays (VFDs), surface-conduction electron-emitter displays (SEDs), field emission displays (FEDs), etc. In one embodiment, the displayed content is a positive indication that the subject is not responsive to a topo I inhibitor. In some embodiments the displayed information is a score of the % likely efficacy of the topo I inhibitor being effective. As an illustrative example only, a 60% score is displayed where the comparison module calculates that approximately 60% of the total topo I polypeptide is not phosphorylated on the S10 residue and approximately 40% of the total topo I polypeptide exists as phospho-S10 topo I, and where a 60% score indicates that a topo I inhibitor is likely to be about 60% responsive in the subject with cancer as compared to a subject which has a cancer where there the serine 10 on topo I polypeptide is non-phosphorylated (i.e. such a subject where absence of phospho-S10-topo I is detected indicates a that a topo I inhibitor is likely to be 100% responsive).

Figure 13:
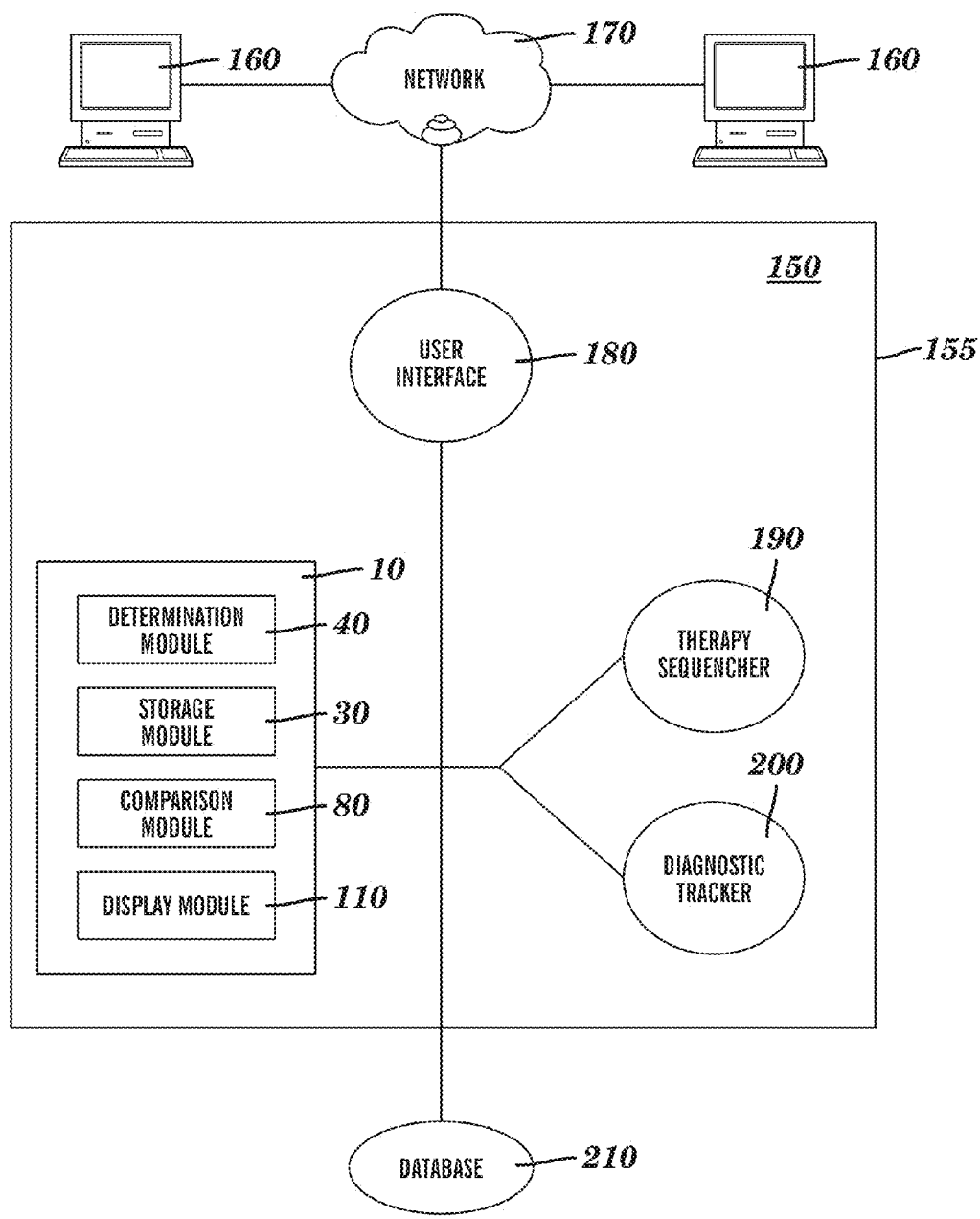
FIG. 13 of a machine 10 for determining if a subject is responsive to a topo I inhibitor according an embodiment of the invention.

FIG. 13 shows a flow diagram of an automated computer system 150 for determining if a subject is responsive to a topo I inhibitor an embodiment of the invention. Illustratively, a system 150 may be adapted to be accessed by a physicians, medical professionals, and/or their assistants using a stand alone computer (not shown), or one or more plurality of networked computers 160 acting as clients. Such clients 160, in turn, may include one or more conventional personal computers and workstations, operating either as a "fat" client or a "thin" client. It should be understood, nevertheless, that other clients 102, such as Web-enabled hand-held devices (e.g., the Palm V® organizer manufactured by Palm, Inc., Santa Clara, Calif. U.S.A., Windows CE devices, and "smart" phones), which use the wireless access protocol (i.e., WAP), and Internet appliances fall within the spirit and scope of the present invention.

Clients 160 of the above types may access system 150 by way of a network 170. Network 170 may include a number of computers and associated devices that are connected by communication facilities. A network may involve permanent connections such as cables, or temporary connections such as those made through telephone or other communication links Examples of a network include: an internet, such as the Internet; an intranet; a local area network (LAN); a wide area network (WAN); and a combination of networks, such as an internet and an intranet. By use of the term "network", it should be understood that the foregoing is not intended to limit the present invention to any particular wireline or wireless network, such as local area networks (i.e., LANs), metropolitan area networks (i.e., MANs), or wide area networks (i.e., WANs). Network 170 may include the Internet (also known as the "World Wide Web"), but it may similarly include intranets, extranets, and virtual private networks (i.e., VPNs) and the like.

In accordance with an embodiment of the invention, system 150 may include a user interface 180, a database 210, a machine 10, comprising a determination module 40, a storage module 30, a comparison module 80 and a display module 110; a therapy sequencer 190, and a diagnostic tracker 220. Collectively, user interface 180, a machine 10, therapy sequencer 190, and diagnostic tracker 120 may comprise a topo I inhibitor prognostic application 155.

User interface 180 may be used to interact with system 115, including viewing data and data comparisons graphically. User interface 180 may permit a user to specify, for example, which subject to analyze, which subject or timepoint to collect data for, which data display to use, etc.

Database 210 may include data collected from patients. Database 210 may include aggregated or statistically processed data. The data may be collected from healthy patients and/or from diseased patients. The data may be classified according to disease type, for example what type of cancer, as well as clinical trial information, topo I inhibitor responsiveness, biographic and demographic subject information. Database 210 may also include data correlating specific topo I inhibitor efficacy with the subjects genetic background and other relevant subject information.

Machine 10 may analyze patient data and/or data from the database. Machine 10 may compare a patient sample to statistically processed data from database 210 to assist in diagnosis and prognosis of a subject cancer and responsiveness to topo I inhibitors. For example, machine 10 may compare a protein topo I phosphorylation profile from a patient with breast cancer to statistically processed data of topo I phosphorylation profiles from other breast cancer patients to determine which types of breast cancer are responsive to topo I inhibitors, and may suggest one or more anti-cancer therapies, including topo I inhibitors which can be used to treat the cancer.

Therapy sequencer 190 may suggest and sequence the course of treatment. Such treatment suggestion could be a single treatment with a topo I inhibitor where the subject is identified to be responsive to a topo I inhibitor, or a combination of agents, for example a combination of a topo I inhibitor and a topo I inhibitor sensitivity agent where a subject is identified to be unresponsive to a topo I inhibitor. In alternative embodiments, the suggested treatment with an anti-cancer agent which is not a topo I inhibitor where the subject is identified to be unresponsive to a topo I inhibitor. Alternatively, the suggested therapy could be multiple doses of topo I inhibitor where the subject has a some, but not all the topo I polypeptide phosphorylated on serine 10.

Diagnostic tracker 200 may track progress of a patient within the course of treatment.

Figure 14:
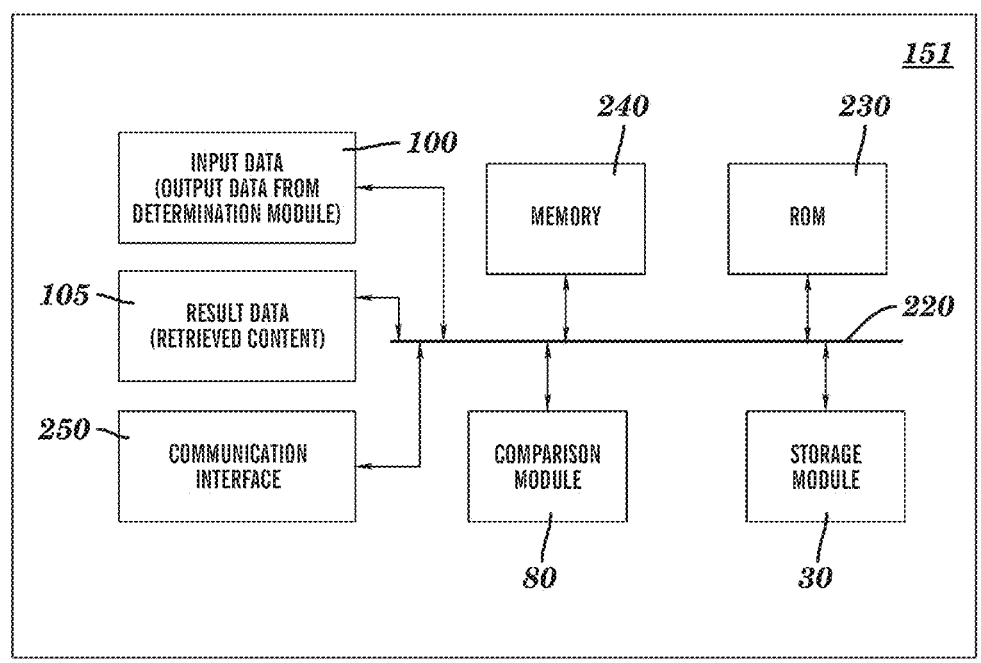
FIG. 14 depicts an exemplary block diagram of a computer system 151 that may be configured to execute the prognostic application 155 illustrated in FIG. 13.

FIG. 14 depicts an exemplary block diagram of a computer system 151 that may be configured to execute the prognostic application 155 illustrated in FIG. 13. Computer 160 may include one or more components that may include a bus 220, a comparison module 80, a memory 240, a read only memory (ROM) 230, a storage device 30, an display data 110, an determination module 40, and a communication interface 250. Bus 220 may include one or more interconnects that permit communication among the components of computer 160, a comparison module 80, a memory 240, a read only memory (ROM) 230, a storage device 30, an display data 110, an determination module 40, and a communication interface 250.

A comparison module 80 can be any type of processor, microprocessor, or processing logic that may interpret and execute instructions (e.g., a field programmable gate array (FPGA)). A comparison module 80 may comprise a single device (e.g., a single core) and/or a group of devices (e.g., multi-core). A comparison module 80 may include logic configured to execute computer-executable instructions configured to implement one or more embodiments. The instructions may reside in the memory 240 or ROM 230, and may include instructions associated with the computer readable media 260.

Memory 240 may be a computer-readable medium 260 that may be configured to store instructions configured to implement one or more embodiments. The memory 240 may be a primary storage accessible to the comparison module 240 and may comprise a random-access memory (RAM) that may include RAM devices, such as Dynamic RAM (DRAM) devices, flash memory devices, Static RAM (SRAM) devices, etc. [0076]ROM 230 may include a non-volatile storage that may store information and computer-executable instructions or computer readable media 260 for the comparison module 80. The computer-executable instructions 260 may include instructions executed by the comparison module 80.

Storage device 30 may be configured to store information and instructions for the comparison module 80. Examples of storage device 30 may include a magnetic disk, optical disk, flash drive, etc. The information and computer-executable instructions and information may be stored on a medium contained in the storage device 30. Examples of media may include a magnetic disk, optical disk, flash memory, etc. Storage device 30 may include a single storage device or multiple storage devices. Moreover, storage device 30 may attach directly to computer 160 and/or may be remote with respect to computer 160 and connected thereto via a network 170 and/or another type of connection, such as a dedicated link or channel.

Determination module 40 may include any mechanism or combination of mechanisms that may permit information to be input into computer 160 from, e.g., a user. Determination module 40 may include logic configured to receive information for computer 160 from, e.g. a user. Examples of methods to input data into the determination module 40 may include a keyboard, mouse, touch sensitive display device, microphone, pen-based pointing device, and/or biometric input device, etc.

Display module 110 may include any mechanism or combination of mechanisms that may output information from computer 160. Display module 110 may include logic configured to output information from computer 160. Embodiments of display module 110 may include displays, printers, speakers, cathode ray tubes (CRTs), plasma displays, light-emitting diode (LED) displays, liquid crystal displays (LCDs), printers, vacuum florescent displays (VFDs), surface-conduction electron-emitter displays (SEDs), field emission displays (FEDs), etc.

Communication interface 250 may include logic configured to interface computer 160 with network 170 and enable computer 160 to exchange information with other entities connected to network 170. Communication interface 250 may include any transceiver-like mechanism that enables computer 160 to communicate with other devices and/or systems, such as a client, a server, a license manager, a vendor, etc. The communications may occur over a communication medium, such as a data network. Communication interface 250 may include one or more interfaces that are connected to the communication medium. The communication medium may be wired or wireless. Communication interface 250 may be implemented as a built-in network adapter, network interface card (NIC), Personal Computer Memory Card International Association (PCMCIA) network card, card bus network adapter, wireless network adapter, Universal Serial Bus (USB) network adapter, modem or any other device suitable for interfacing computer 160 to any type of network.

It should be noted that embodiments may be implemented using some combination of hardware and/or software. It should be further noted that a computer-readable medium that comprises computer-executable instructions for execution in a processor may be configured to store various embodiments. The computer-readable medium may include volatile memories, non-volatile memories, flash memories, removable discs, non-removable discs and so on. In addition, it should be noted that various electromagnetic signals such as wireless signals, electrical signals carried over a wire, optical signals carried over optical fiber and the like may be encoded to carry computer-executable instructions and/or computer data that embodiments of the invention on e.g., a communication network.

Embodiments may be embodied in many different ways as a software component. For example, it may be a stand-alone software package, or it may be a software package incorporated as a "tool" in a larger software product, such as, for example, a medical diagnostic product. It may be downloadable from a network, for example, a website, as a stand-alone product or as an add-in package for installation in an existing software application. It may also be available as a client-server software application, or as a web-enabled software application.

FIG. 15 shows a flow chart of a instructions for analyzing if a subject is responsive to a topo I inhibitor. In block 260, a biological sample is placed in a biological sample container. Examples of biological samples may be biopsy tissue, samples grown in culture, laser microdissected cells, FACs sorted cells, blood cells, fine needle aspirant, core biopsy, non-cellular bodily fluid etc. In block 270, the phosphorylation status is determined by the determination module 40 using any analysis technique of a skilled artisan as disclosed herein, including for example, RPMA, ELISA, suspension bead array (e.g. Lumuinex), surface Plasmon resonance, evanescent wave, cantilever based nano-sensors, immunofluorescence, immunohistochemistry, MRI etc. The output data 100 from the determination module 40 is stored on the storage device 30. In block 280 the output data 100 is stored on the storage module 40, and in block 290, the comparison module compares the output data 100 with the stored reference data on the storage device 40. In block 300, the analysis performed by the comparison module determines if there is presence of phospho-topo I in the biological sample as compared to reference data, and if the analysis determines the presence of phospho-topo I, the analysis progresses of block 310 to determine if there is the presence of phospho-S10 topo I, whereas if the analysis determines the absence of phospho-topo I, the display module 110 indicates the subject is more responsive to a topo I inhibitor as compared to a subject with cancer that has the presence of phospho-S10 topo I (330). In block 320, if the analysis determines the absence of phospho-S10-topo I, the display module 110 indicates the subject is more responsive to a topo I inhibitor as compared to a subject with cancer that has the presence of phospho-S10 topo I (330). If the analysis determines the presence of phospho-S10 topo I, the analysis progresses to block 320 to calculate the % of phospho-S10 topo I of total topo I polypeptide amount, and if the % of phospho-S10 topo I is above a pre-determined threshold level, the display module 110 indicates the subject is less likely to be responsive (i.e. subject is likely to be responsive) to a topo I inhibitor as compared to a subject with cancer that has absence of phospho-S10 topo I (340). If the % of phospho-S10 topo I is below a pre-determined threshold level, the display module 110 indicates the subject is likely to be responsive to a topo I inhibitor as compared to a subject with cancer that has absence of phospho-S10 topo I, shown in block 350. In block 360, the result data or display data is optionally transmitted to a patient or physician. Block 370 is program end point. Illustratively, a computer may take the form of a computer workstation such as SGI Octane R1000, and IBM compatible PC (both windows and Linux platforms) and other similar computer systems.

Accordingly, in some embodiments the system, or comparison module can determine if a subject is above a certain pre-defined threshold level, and produce output data 100 indicate that the subject is likely to be identified to be unresponsive to a topo I inhibitor. In some embodiments, a pre-defined threshold level is level 3, wherein the % of phospho-S10 topo I polypeptide (from the total topo I polypeptide) is about 25% or above, a subject is likely to be unresponsive to a topo I inhibitor as compared to a subject with a threshold level below 3 (i.e. less than 25%). Accordingly, in some embodiments, a pre-defined threshold level to identify if a subject is unresponsive to a topo I inhibitor is a 25% or greater, wherein a subject having a % of phospho-S10 topo I inhibitor to total topo I polypeptide of 25% or greater (i.e. about at least 30% or at least about 40% or a least about 50% or at least about 60% or more) is identified as being unresponsive to a topo I inhibitor, whereas a subject having a % of phospho-S10 topo I inhibitor to total topo I polypeptide of less than 25% (i.e. about 20% or about 10% or about 5% or about 2% or less) is identified as being responsive, or partially responsive to a topo I inhibitor.

In some embodiments, the analysis (block 300) performed by the comparison module determines the % of phospho-S10 topo I polypeptide of total topo I polypeptide and the output data 100 from the determination module 40 classifies the % of phospho-S10 topo I polypeptide of total topo I polypeptide in the biological sample into specific classifications, for example, grades 1, 2, 3 and 4 as disclosed herein. For example, the output data 100 can grade (i.e. the level of phospho-S10 topo I polypeptide as compared to non-phospho S10 topo I polypeptide) which can be categorized on 4 levels. For example but not limited to, level 1 is about a 0% to 10% level phospho-S10 topo I polypeptide and indicates a subject is likely to be fully responsive to a topo I inhibitor, level 2 is about a 10-25% level phospho-S10 topo I polypeptide and indicates a subject is likely to be partially responsive to a topo I inhibitor; level 3 is a 25-50% level of level phospho-S10 topo I polypeptide and indicates a subject is likely to be unresponsive to a topo I inhibitor, and level 4 is any level of level phospho-S10 topo I polypeptide above 50%, for example at least 50%, or at least about 60% or at least about 70% or at least about 80% or at least about 90% or at least about 100% indicates a subject is likely to be completely non-responsive to a topo I inhibitor. In some embodiments, the output data 100 is a grade of 1 to 4, where the grade represents the degree of phospho-S10 topo I polypeptide as compared to degree of non-phospho S10 topo I polypeptide in the biological sample. In some embodiments, the output data is a grade of 1 of 4 grades; grades 1 (0-10%), 2 (10-25%), 3 (25-50%) or 4 (>50%), where level 1 indicates a subject is likely to be responsive to a topo I inhibitor, where level 2 indicates a subject is likely to be partially responsive (i.e. about 50% or less responsive) to a topo I inhibitor as compared to level 1, where level 3 indicates a subject is likely to be unresponsive to a topo I inhibitor as compared to a subject classified as level 1 (i.e. a subject will likely have about 10% or less efficacy of a topo I inhibitor), and where level 4 indicates a subject is likely to be completely unresponsive to a topo I inhibitor as compared to a subject classified as a level 1 (i.e. a subject will likely have about 5% or about a 2% or less efficacy of a topo I inhibitor).

As discussed herein, the machine and computer system and computer readable media comprises various modules as discussed in detail below. As can be appreciated by one of ordinary skill in the art, each of the modules comprise various sub-routines, procedures, definitional statements, and macros. Each of the modules are typically separately compiled and linked into a single executable program. Therefore, the following description of each of the modules is used for convenience to describe the functionality of the system. Thus, the processes that are undergone by each of the modules may be arbitrarily redistributed to one of the other modules, combine together in a single module, or made available in, for example, a shareable dynamic link library.

Determination Module.

The determination module has computer executable instructions to provide sequence information in computer readable form.

As an example, determination modes for determining the binding of a protein-binding molecule to a protein, for example but not limited to the binding of an anti-phospho-S10 antibody to a topo I polypeptide which is phosphorylated at serine 10 (S10) include for example but are not limited to automated immunohistochemistry apparatus, for example, robotically automated immunohistochemistry apparatus which in an automated system section the tissue or biological sample specimen, prepare slides, perform immunohistochemistry procedure and detect intensity of immunostaining, such as intensity of anti-phospho-S10 topo I antibody staining in the biological sample or tissue and produce output data. Examples of such automated immunohistochemistry apparatus are commercially available, for example such Autostainers 360, 480, 720 and Labvision PT module machines from LabVision Corporation, which are disclosed in U.S. Pat. Nos. 7,435,383; 6,998,270; 6,746,851, 6,735,531; 6,349,264; and 5,839;091 which are incorporated herein in their entirety by reference. Other commercially available automated immunohistochemistry instruments are also encompassed for use in the present invention, for example, but not are limited BOND™ Automated Immunohistochemistry & In Situ Hybridization System, Automate slide loader from GTI vision. Automated analysis of immunohistochemistry can be performed by commercially available systems such as, for example, IHC Scorer and Path EX, which can be combined with the Applied spectral Images (ASI) CytoLab view, also available from GTI vision or Applied Spectral Imaging (ASI) which can all be integrated into data sharing systems such as, for example, Laboratory Information System (LIS), which incorporates Picture Archive Communication System (PACS), also available from Applied Spectral Imaging (ASI) (see world-wide-web: spectral-imaging.com). Other a determination module can be an automated immunohistochemistry systems such as NexES® automated immunohistochemistry (IHC) slide staining system or Bench-Mark® LT automated IHC instrument from Ventana Discovery SA, which can be combined with VIAS™ image analysis system also available Ventana Discovery. BioGenex Super Sensitive MultiLink® Detection Systems, in either manual or automated protocols can also be used as the detection module, preferably using the BioGenex Automated Staining Systems. Such systems can be combined with a BioGenex automated staining systems, the i6000™ (and its predecessor, the OptiMax® Plus), which is geared for the Clinical Diagnostics lab, and the GenoMx 6000™, for Drug Discovery labs. Both systems BioGenex systems perform "All-in-One, All-at-Once" functions for cell and tissue testing, such as Immunohistochemistry (IHC) and In Situ Hybridization (ISH).

As used herein, "sequence information" refers to any nucleotide and/or amino acid sequence, including but not limited to full-length nucleotide and/or amino acid sequences, partial nucleotide and/or amino acid sequences, or mutated sequences. Moreover, information "related to" the sequence information includes detection of the presence or absence of a sequence (e.g., detection of a mutation or deletion), determination of the concentration of a sequence in the sample (e.g. amino acid sequence expression levels, or nucleotide (RNA or DNA) expression levels), and the like.

As an example, determination modules for determining phosphorylation status of topo I polypeptide, for instance the detecting the total level of topo I polypeptide amount and/or the level of phospho-S10 topo I polypeptide may include known systems for automated protein expression analysis including but not limited Mass Spectrometry systems including MALDI-TOF, or Matrix Assisted Laser Desorption Ionization-Time of Flight systems; SELDI-TOF-MS Protein-Chip array profiling systems, e.g. Machines with Ciphergen Protein Biology System II™ software; systems for analyzing gene expression data (see for example U.S. 2003/0194711); systems for array based expression analysis, for example HT array systems and cartridge array systems available from Affymetrix (Santa Clara, Calif. 95051) AutoLoader, Complete GeneChip® Instrument System, Fluidics Station 450, Hybridization Oven 645, QC Toolbox Software Kit, Scanner 3000 7G, Scanner 3000 7G plus Targeted Genotyping System, Scanner 3000 7G Whole-Genome Association System, GeneTitan™ Instrument, GeneChip® Array Station, HT Array; an automated ELISA system (e.g. DSX® or DS2® form Dynax, Chantilly, Va. or the ENEASYSTEM III®, Triturus®, The Mago® Plus); Densitometers (e.g. X-Rite-508-Spectro Densitometer®, The HYRYS™ 2 densitometer); automated Fluorescence insitu hybridization systems (see for example, U.S. Pat. No. 6,136,540); 2D gel imaging systems coupled with 2-D imaging software; microplate readers; Fluorescence activated cell sorters (FACS) (e.g. Flow Cytometer FACSVantage SE, Becton Dickinson); radio isotope analyzers (e.g. scintillation counters).

Algorithms for identifying protein phosphorylation profiles, such as the total amount of phospho-S10 topo I polypeptide or alternative the % of phospho-S10 topo I polypeptide of the total topo I polypeptide available in a biological sample can include the use of optimization algorithms such as the mean variance algorithm, e.g. J MP Genomics algorithm available from JMP Software.

As used herein, "expression level information" refers to any nucleotide and/or amino acid expression level information, including but not limited to full-length nucleotide and/or amino acid sequences, partial nucleotide and/or amino acid sequences, or mutated sequences. Moreover, information "related to" the expression level information includes detection of the presence or absence of a sequence (e.g., presence or absence of an amino acid sequence or nucleotide sequence), determination of the concentration of a sequence in the sample (e.g. amino acid sequence levels, or nucleotide (RNA or DNA) expression levels), and the like Storage Module In some embodiments, the topo I phosphorylation information determined in the determination module can be read by the storage device. As used herein the "storage device" is intended to include any suitable computing or processing apparatus or other device configured or adapted for storing data or information. Examples of electronic apparatus suitable for use with the present invention include stand-alone computing apparatus; communications networks, including local area networks (LAN), wide area networks (WAN), Internet, Intranet, and Extranet; and local and distributed processing systems. Storage devices also include, but are not limited to: magnetic storage media, such as floppy discs, hard disc storage medium, and magnetic tape; optical storage media such as compact disc; electronic storage media such as RAM, ROM, EPROM, EEPROM and the like; general hard disks and hybrids of these categories such as magnetic/optical storage media. The medium is adapted or configured for having recorded thereon sequence information or expression level information. The data are typically provided in digital form that can be transmitted and read electronically, e.g., via the Internet, on diskette, or any other mode of electronic or non-electronic communication.

Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, other types of volatile and non-volatile memory, any other medium which can be used to store the desired information and which can accessed by a computer, and any suitable combination of the foregoing. The computer readable media does not encompass a data signal or a carrier wave, preferably the computer readable medium is of physical form.

In some embodiments of this aspect and all other aspects of the present invention, a computer readable media can be any available media that can be accessed by a computer. By way of example, and not a limitation, computer readable media may comprise computer storage media and communication media.

As used herein, "stored" refers to a process for encoding information on the storage device. Those skilled in the art can readily adopt any of the presently known methods for recording information on known media to generate manufactures comprising the sequence information or expression level information.

In some embodiments of this aspect and all other aspects of the present invention a variety of software programs and formats can be used to store the phosphorylation information or expression level information on the storage device. Any number of data processor structuring formats (e.g., text file or database) can be employed to obtain or create a medium having recorded thereon the sequence information or expression level information.

In some embodiments of this aspect and all other aspects of the present invention, the reference data stored in the storage device to be read by the comparison module is sequence information data obtained from a control biological sample of the same type as the biological sample to be tested. Alternatively, the reference data are a database, e.g., a part of the entire genome sequence of an organism, or a protein family of sequences, or an expression level profile (RNA, protein or peptide). In one embodiment the reference data are sequence information or expression level profiles that are indicative of a specific disease or disorder.

In one embodiment, the reference data is the reference phosphorylation status of topo I polypeptide of SEQ ID NO: 2.

In some embodiments of this aspect and all other aspects of the present invention, the reference data are electronically or digitally recorded and annotated from databases including, but not limited to GenBank (NCBI) protein and DNA databases such as genome, ESTs, SNPS, Traces, Celara, Ventor Reads, Watson reads, HGTS, etc.; Swiss Institute of Bioinformatics databases, such as ENZYME, PROSITE, SWISS-2DPAGE, Swiss-Prot and TrEMBL databases; the Melanie software package or the ExPASy WWW server, etc., the SWISS-MODEL, Swiss-Shop and other network-based computational tools; the Comprehensive Microbial Resource database (The institute of Genomic Research). The resulting information can be stored in a relational data base that may be employed to determine homologies between the reference data or genes or proteins within and among genomes.

Comparison Module

By providing phosphorylation information or expression level information in computer-readable form, one can use the phosphorylation information or expression level information in readable form in the comparison module to compare a specific phosphorylation or expression profile with the reference data within the storage device. For example, search programs can be used to identify relevant reference data the phosphorylation status or expression level information that match a particular subject (reference data, e.g. data obtained from a control reference biological sample from the same subject, for example at an earlier timepoint, i.e. $t_1, t_2, t_3$ when comparing against a timepoint of $t_4$ or above) or direct comparison of the determined phosphorylation and/or topo I polypeptide expression level can be compared to the reference data phospho-S10 topo I level or total topo I protein expression level (e.g. data obtained from a control sample). The comparison made in computer-readable form provides computer readable content which can be processed by a variety of means. The content can be retrieved from the comparison module, the retrieved content.

In some embodiments of this aspect and all other aspects of the present invention, the "comparison module" can use a variety of available software programs and formats for the comparison operative to compare sequence information determined in the determination module to reference data. In one embodiment, the comparison module is configured to use pattern recognition techniques to compare sequence information from one or more entries to one or more reference data patterns. The comparison module may be configured using existing commercially-available or freely-available software for comparing patterns, and may be optimized for particular data comparisons that are conducted. The comparison module provides computer readable information related to the sequence information that can include, for example, detection of the presence or absence of a sequence (e.g., detection of a mutation or deletion (protein or DNA), information regarding distinct alleles, or omission or repetition of sequences); determination of the concentration of a sequence in the sample (e.g. amino acid sequence/protein expression levels, or nucleotide (RNA or DNA) expression levels), or determination of an expression profile.

In one embodiment, the comparison module permits the comparison of information of the protein phosphorylation of topo I polypeptide from the output data of the determination module, in particular the information of phospho-S10 topo I polypeptide with reference data.

In one embodiment, the comparison module performs comparisons with mass-spectrometry spectra, for example comparisons of peptide fragment sequence information can be carried out using spectra processed in MATLB with script called "Qcealign" (see for example WO2007/022248, herein incorporated by reference) and "Qpeaks" (Spectrum Square Associates, Ithaca, N.Y.), or Ciphergen Peaks 2.1™ software. The processed spectra can then be aligned using alignment algorithms that align sample data to the control data using minimum entropy algorithm by taking baseline corrected data (see for example WO2007/022248, herein incorporated by reference). The retrieved content can be further processed by calculating ratios. For example, the retrieved content can be processed by a simple algorithm to calculate the % phosphorylated protein over the total protein present. In one example, the % of phospho-S10 topo I is calculated as follows: the amount of phospho-S10-topo I polypeptide (molar value)/the amount of total topo I polypeptide (molar value)×

100. Thus, the comparison module allows protein expression profiles can be discerned and protein phosphorylation profiles can be discerned.

In one embodiment, the comparison module compares the protein phosphorylation profiles. In one embodiment, the comparison module compares gene expression profiles. For example, detection of gene expression profiles can be determined using Affymetrix Microarray Suite software version 5.0 (MAS 5.0) to analyze the relative abundance of a gene or genes on the basis of the intensity of the signal from probe sets and the MAS 5.0 data files can be transferred into a database and analyzed with Microsoft Excel and GeneSpring 6.0 software (Silicon genetics). The detection algorithm of MAS 5.0 software can be used to obtain a comprehensive overview of how many transcripts are detected in given samples and allows a comparative analysis of 2 or more microarray data sets.

In some embodiments of this aspect and all other aspects of the present invention, the comparison module compares the phosphorylation status of topo I, or protein phosphorylation profiles for instance the phospho-S10 topo I protein phosphorylation profiles. Any available comparison software can be used, including but not limited to, the Ciphergen Express (CE) and Biomarker Patterns Software (BPS) package, Ciphergen Biosystems, Inc., CA, USA. Comparative analysis can be done with protein chip system software (e.g. The Proteinchip suite for Bio-Rad Laboratories).

In one embodiment, computational algorithms such as expectation-maximization (EM), subtraction and PHASE are used in methods for statistical estimation of haplotypes (see, e.g., Clark, A. G. Inference of haplotypes from PCR-amplified samples of diploid populations. Mol Biol Evol 7, 111-22. (1990); Stephens, M., Smith, N. J. & Donnelly, P. A new statistical method for haplotype reconstruction from population data. Am J Hum Genet 68, 978-89. (2001); Templeton, A. R., Sing, C. F., Kessling, A. & Humphries, S. A cladistic analysis of phenotype associations with haplotypes inferred from restriction endonuclease mapping. II. The analysis of natural populations. Genetics 120, 1145-54. (1988)).

In some embodiments of this aspect and all other aspects of the present invention, the comparison module, or any other module of the invention, may include an operating system (e.g., UNIX) on which runs a relational database management system, a World Wide Web application, and a World Wide Web server. World Wide Web application includes the executable code necessary for generation of database language statements [e.g., Standard Query Language (SQL) statements]. Generally, the executables will include embedded SQL statements. In addition, the World Wide Web application may include a configuration file which contains pointers and addresses to the various software entities that comprise the server as well as the various external and internal databases which must be accessed to service user requests. The Configuration file also directs requests for server resources to the appropriate hardware—as may be necessary should the server be distributed over two or more separate computers. In one embodiment, the World Wide Web server supports a TCP/IP protocol. Local networks such as this are sometimes referred to as "Intranets." An advantage of such Intranets is that they allow easy communication with public domain databases residing on the World Wide Web (e.g., the GenBank or Swiss Pro World Wide Web site). Thus, in a particular preferred embodiment of the present invention, users can directly access data (via Hypertext links for example) residing on Internet databases using a HTML interface provided by Web browsers and Web servers.

In some embodiments of this aspect and all other aspects of the present invention, a computer-readable data embodied on one or more computer-readable media may define instructions, for example, as part of one or more programs, that, as a result of being executed by a computer, instruct the computer to perform one or more of the functions described herein (e.g., in relation to computer system 150, or computer readable medium 260), and/or various embodiments, variations and combinations thereof. Such instructions may be written in any of a plurality of programming languages, for example, Java, J, Visual Basic, C, C#, or C++, Fortran, Pascal, Eiffel, Basic, COBOL, etc., or any of a variety of combinations thereof. The computer-readable media on which such instructions are embodied may reside on one or more of the components of either of computer system 150 [machine 10], or computer readable medium 260 described herein, may be distributed across one or more of such components, and may be in transition there between.

In some embodiments of this aspect and all other aspects of the present invention, a computer-readable media may be transportable such that the instructions stored thereon can be loaded onto any computer resource to implement the aspects of the present invention discussed herein. In addition, it should be appreciated that the instructions stored on the computer-readable medium, described above, are not limited to instructions embodied as part of an application program running on a host computer. Rather, the instructions may be embodied as any type of computer code (e.g., software or microcode) that can be employed to program a processor to implement aspects of the present invention. The computer executable instructions may be written in a suitable computer language or combination of several languages. Basic computational biology methods are described in, e.g. Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001).

Instructions can be provided to the computer systems 150 which refers to a number of computer-implemented steps for processing information in the system. Instructions can be implemented in software, firmware or hardware and include any type of programmed step undertaken by modules of the electronic financing system. The computer system 150 can be connected to a local network. One example of the Local Area Network may be a corporate computing network, including access to the Internet, to which computers and computing devices comprising the financing system are connected. In one embodiment, the LAN conforms to the Transmission Control Protocol/Internet Protocol (TCP/IP) industry standard. Transmission Control Protocol Transmission Control Protocol (TCP) is a transport layer protocol used to provide a reliable, connection-oriented, transport layer link among computer systems. The network layer provides services to the transport layer. Using a two-way handshaking scheme, TCP provides the mechanism for establishing, maintaining, and terminating logical connections among computer systems. TCP transport layer uses IP as its network layer protocol. Additionally, TCP provides protocol ports to distinguish multiple programs executing on a single device by including the destination and source port number with each message. TCP performs functions such as transmission of byte streams, data flow definitions, data acknowledgments, lost or corrupt data re-transmissions, and multiplexing multiple connections through a single network connection. Finally, TCP is responsible for encapsulating information into a datagram structure.

In alternative embodiments, the LAN may conform to other network standards, including, but not limited to, the International Standards Organization's Open Systems Interconnection, IBM's SNA, Novell's Netware, and Banyan VINES. The computer system may comprise a microprocessor. A microprocessor may be any conventional general purpose single- or multi-chip microprocessor such as a Pentiumw processor, a PentiumX Pro processor, a 8051 processor, a MISS, processor, a Power PC'processor, of an ALPHAZ processor. In addition, the microprocessor may be any conventional special purpose microprocessor such as a digital signal processor or a graphics processor. The microprocessor typically has conventional address lines, conventional data lines, and one or more conventional control lines.

In some embodiments, the computer system 150 as described herein can include any type of electronically connected group of computers including, for instance, the following networks: Internet, Intranet, Local Area Networks (LAN) or Wide Area Networks (WAN). In addition, the connectivity to the network may be, for example, remote modem, Ethernet (IEEE 802.3), Token Ring (IEEE 802.5), Fiber Distributed Datalink Interface (FDDI) or Asynchronous Transfer Mode (ATM). Note that computing devices may be desktop, server, portable, hand-held, set-top, or any other desired type of configuration. As used herein, an Internet includes network variations such as public internet, a private internet, a secure internet, a private network, a public network, a value-added network, an intranet, and the like.

The computer systems and comparison module can use a variety of operating Systems. For example the computer system 150 can be used in connection with various operating systems such as: UNIX, Disk Operating System (DOS), OS/2, Windows 3. X, Windows 95, Windows 98, and Windows NT. The computer system 150 as described herein can be programmed in any programming language, for example the system may be written in any programming language such as C, C++, BASIC, Pascal, Java, and FORTRAN and ran under the well-known operating system. C, C++, BASIC, Pascal, Java, and FORTRAN are industry standard programming languages for which many commercial compilers can be used to create executable code.

In one embodiment of the invention, the computer system can comprise a pattern comparison software can be used to determine whether patterns of protein phosphorylation profiles are indicative of a subject being responsive to a topo I inhibitor, or the likelihood of efficacy of a topo I inhibitor in the treatment of a cancer.

In some embodiments of this aspect and all other aspects of the present invention, a comparison module provides computer readable data that can be processed in computer readable form by predefined criteria, or criteria defined by a user, to provide a retrieved content that may be stored and output as requested by a user using a display module.

In some embodiments of this aspect and all other aspects of the present invention, the retrieved content can be an expression profile, and/or a protein phosphorylation profile of one or more proteins. In one embodiment the retrieved content is the presence of phospho-S10-topo I protein, and in another embodiment, the retrieved content is the level of phospho-S10-topo I, for example the level (i.e. %) of topo I protein which exists as phospho-S10-topo I as compared to the total amount of topo I polypeptide. In one embodiment, the retrieved content is a positive or negative regarding the presence or absence of phospho-S10-topo I protein. In anther embodiment, the retrieved content is a positive indicator that the biological sample is unresponsive to a topo I inhibitor and in another embodiment the retrieved content is an indicator that the biological sample is likely to be responsive to a topo I inhibitor.

Display Module

In some embodiments of this aspect and all other aspects of the present invention, a page of the retrieved content which is the report data from the comparison module is displayed on a computer monitor 120. In one embodiment of the invention, a page of the retrieved content is displayed through printable media 130 and 140. The display module 120 can be any computer adapted for display of computer readable information to a user, non limiting examples include, for example, general-purpose computers such as those based on Intel PENTIUM-type processor, Motorola PowerPC, Sun UltraSPARC, Hewlett-Packard PA-RISC processors, any of a variety of processors available from Advanced Micro Devices (AMD), or any other type of processor. Other displays modules include; speakers, cathode ray tubes (CRTs), plasma displays, light-emitting diode (LED) displays, liquid crystal displays (LCDs), printers, vacuum florescent displays (VFDs), surface-conduction electron-emitter displays (SEDs), field emission displays (FEDs), etc In some embodiments of this aspect and all other aspects of the present invention, a World Wide Web browser is used for providing a user interface for display of the retrieved content. It should be understood that other modules of the invention can be adapted to have a web browser interface. Through the Web browser, a user may construct requests for retrieving data from the comparison module. Thus, the user will typically point and click to user interface elements such as buttons, pull down menus, scroll bars, etc. conventionally employed in graphical user interfaces. The requests so formulated with the user's Web browser are transmitted to a Web application which formats them to produce a query that can be employed to extract the pertinent information related to the sequence information, the retrieved content, e.g. display of an indication of the presence or absence of mutation or deletion (DNA or protein); display of expression levels of an amino acid sequence (protein); display of nucleotide (RNA or DNA) expression levels; or display of expression, SNP, or mutation profiles, or haplotypes. In one embodiment, the sequence information of the reference sample data is also displayed.

The display module 110 also displays whether the retrieved content is indicative of the subject being responsive or non-responsive to a topo I inhibitor, e.g. whether the subject has increased phospho-S10 topo I inhibitor as compared to a reference control subject which does not have phospho-S10 topo I polypeptide indicates the subject is more likely to be unresponsive to a topo I inhibitor compared the control subject. In one embodiment, the retrieved content is a positive or negative regarding the presence or absence of a phospho-S10 topo I polypeptide is displayed, where a positive indication indicates the subject is likely to be more unresponsive to a topo I inhibitor, where a negative indication indicates the subject is likely to be more responsive to a topo I inhibitor.

Selection of Subjects Amenable to Determining their Responsiveness to a Topo I Inhibitor Treatment.

Embodiments of the invention provide methods for the determination of the likelihood of a topo I inhibitor treatment to be ineffective, predicted on the inventor's finding of the presence of phospho-S10 topo I in a biological sample from a subject. Subjects amenable to testing the phosphorylation status of topo I polypeptide, for example the levels of phospho-S10 topo using the methods, kits, machines, computer systems and media as disclosed herein include subjects at risk of a cancer, as well as subjects at risk of developing cancer.

In one embodiment, the cancer tissue is breast cancer of the triple-negative subtype. Embodiments of the invention also provide methods for altering the sensitivity (i.e. increasing the sensitivity) of a tumor cell to a topo I inhibitor treatments, in particular CPT or analogues thereof, by co-administering an agent which dephosphorylates S10 on the topo I polypeptide and/or inhibits phosphorylation at S10 of topo I, for example an antagonists to DNA-PK.

Accordingly, the methods of the invention relate to the analysis and treatment of a variety of tumor cell types, to a topo I inhibitor treatment. For example, the tumor cell types can be selected from a group comprising of gastrointestinal cancer, gastric cancer, squamous cell carcinomas (SCC), head and neck cancer, lung cancer, non-small cell lung cancer (NSCLC) and small-cell lung cancer (SCLC), lymphoma, sarcoma, primary and metastic melanoma, thymoma, non-Hodgkin's lymphoma, Hodgkin's lymphoma, cancer of the nervous system, brain cancer, bone-marrow cancer, bone cancer, kidney cancer, uterine cancer, cervical cancer, colon cancer, retina cancer, skin cancer, bladder cancer, colon cancer, esophageal cancer, testicular cancer, cervical cancer, liver cancer, renal cancer, pancreatic cancer, genital-urinary cancer, gastrointestinal, gum cancer, tongue cancer, kidney cancer, nasopharynx cancer, stomach cancer, endometrial cancer and bowel tumor cell cancer, adrenocarcinomas such as prostate cancer, ovarian cancer, breast cancer, and pancreatic cancer.

In some embodiments, subjects amenable to testing for the phosphorylation status of topo I protein, and in particular the level of phospho-S10 topo I polypeptide using the methods, kits, machines, computer systems and media as disclosed herein include subjects with breast cancer, in particular the triple negative subtype breast cancer, which is characterized by ER/PR-negative also lacking HER2 expression. In alternative embodiments, subjects amenable to testing using the methods as disclosed herein are subjects with squamous cell carcinomas (SCC) or prostate cancer.

In some embodiments, subjects amenable to testing for the phosphorylation status of topo I protein, and in particular the level of phospho-S10 topo I polypeptide using the methods, kits, machines, computer systems and media as disclosed herein include any subject currently being administered or about to be administered a topo I inhibitor based treatment, such as such as CPT or an analogue, mimetic or derivatives thereof. In alternative embodiments, subjects amenable to the diagnostic tests as disclosed herein to determine the phosphorylation status of topo I protein, and in particular the level of phospho-S10 topo I polypeptide using the methods, kits, machines, computer systems and media as disclosed herein, include any subject that has been administered a topo I inhibitor, such as CPT or analogues or derivatives thereof, in the past and was found that such treatment was not effective, or the subject is, or has had cancer remission. Testing of such subjects using the methods, kits, machines, computer systems and media as disclosed herein is useful to determine if the failure of the prior administration of a topo I inhibitor treatment was due to the phosphorylation status of topo I protein, and in particular the presence of phospho-S10 topo I polypeptide, and thus identifies a subject not likely to be responsive to such a topo I inhibitor treatment. Accordingly, a physician can direct such subjects to be administered an alternative treatment regime not involving a topo I inhibitor in future cancer treatments or prophylactic cancer treatments.

In some embodiments, subjects amenable to testing for the phosphorylation status of topo I protein, and in particular the level of phospho-S10 topo I polypeptide using the methods, kits, machines, computer systems and media as disclosed herein include are adult and pediatric oncology subjects which have cancers such as solid phase tumors/malignancies, locally advanced tumors, human soft tissue sarcomas, metastatic cancer, including lymphatic metastases, blood cell malignancies including multiple myeloma, acute and chronic leukemias, and lymphomas, head and neck cancers including mouth cancer, larynx cancer and thyroid cancer, lung cancers including small cell carcinoma and non-small cell cancers, breast cancers including small cell carcinoma and ductal carcinoma, gastrointestinal cancers including esophageal cancer, stomach cancer, colon cancer, colorectal cancer and polyps associated with colorectal neoplasia, pancreatic cancers, liver cancer, urologic cancers including bladder cancer and prostate cancer, malignancies of the female genital tract including ovarian carcinoma, uterine (including endometrial) cancers, and solid tumor in the ovarian follicle, kidney cancers including renal cell carcinoma, brain cancers including intrinsic brain tumors, neuroblastoma, askocytic brain tumors, gliomas, metastatic tumor cell invasion in the central nervous system, bone cancers including osteomas, skin cancers including malignant melanoma, tumor progression of human skin keratinocytes, squamous cell carcinoma, basal cell carcinoma, hemangiopericytoma and Kaposi's sarcoma.

In some embodiments, subjects amenable to testing for the phosphorylation status of topo I protein, and in particular the level of phospho-S10 topo I polypeptide using the methods, kits, machines, computer systems and media as disclosed herein include subjects with cancers such as, but are not limited to, bladder cancer; breast cancer; brain cancer including glioblastomas and medulloblastomas; cervical cancer; choriocarcinoma; colon cancer including colorectal carcinomas; endometrial cancer; esophageal cancer; gastric cancer; head and neck cancer; hematological neoplasms including acute lymphocytic and myelogenous leukemia, multiple myeloma, AIDS associated leukemias and adult T-cell leukemia lymphoma; intraepithelial neoplasms including Bowen's disease and Paget's disease, liver cancer; lung cancer including small cell lung cancer and non-small cell lung cancer; lymphomas including Hodgkin's disease and lymphocytic lymphomas; neuroblastomas; oral cancer including squamous cell carcinoma; osteosarcomas; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, synovial sarcoma and osteosarcoma; skin cancer including melanomas, Kaposi's sarcoma, basocellular cancer, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; transitional cancer and renal cancer including adenocarcinoma and Wilm's tumor.

In some embodiments, subjects amenable to testing for the phosphorylation status of topo I protein, and in particular the level of phospho-S10 topo I polypeptide using the methods, kits, machines, computer systems and media as disclosed herein include subjects identified with or having increased risk of cancer, for example subjects identified to carry a genetic mutation or polymorphism associated with an increase risk of developing cancer. Such mutations and genetic susceptibility genes and loci are commonly known by persons skilled in the art, for example some of the more commonly known genes where a mutation is associated with increase in cancer include, but are not limited to; BRAC1, BRAC2, EGFR, EIF4A2, ERBB2, RB1, CDKN2A, P53, INK4a, APC, MLH1, MSH2, MSH6, WTI, NF1, NF2, and VHL (see http://www.cancer.org/docroot/ETO/content/ETO_1_4x_oncogenes_and_tumor_suppressor_genes.asp).

In some embodiments, subjects amenable to determination of the phosphorylation status of topo I protein, and in particular the level of phospho-S10 topo I polypeptide using the methods, kits, machines, computer systems and media as disclosed have been identified to have cancer as determined by a number of cancer screens commonly known by persons of ordinary skill in the art, for example a number of biochemical and genetic markers or other biomarkers. Biomarkers are defined as cellular, biochemical, molecular or genetic alterations by which a normal, abnormal or simply biologic process can be recognized or monitored. Biomarkers are measurable in biological media, such as human tissues, cells or fluids. Biomarkers could be used to identify pathological processes before individuals become symptomatic or to identify individuals who are responsive to cancer.

Several classes of biomarkers in cancer cells and bodily fluids have been studied, mostly in laboratories examining specific observations but also in limited clinical settings. Several biomarkers have shown only limited utility: e.g., CD44, telomerase, transforming growth factor-α (TGF-α)3, transforming growth factor-β (TGF-β), epidermal growth factor receptor erbB-2 (erbB-2), epidermal growth factor receptor erbB-3 (erbB-3), mucin 1 (MUC1), mucin 2 (MUC2) and cytokeratin 20 (CK20). Other biomarkers are used in clinical practice and include, for example Prostate specific antigen (PSA) and cancer antibody or tumor marker 125 (CA125). Several protein markers can be used as cancer biomarkers, for example but not limited to, Fecal occult blood test (FOBT), which is a protein biomarker shown to decrease cause-specific mortality in cancer screens.

In some embodiments, the biological sample obtained from the subject is from a biopsy tissue sample, and in some embodiments, the sample is from a tumor or cancer tissue sample. The testing for the phosphorylation status of topo I protein, and in particular the level of phospho-S10 topo I polypeptide can be determined using the methods, kits, machines, computer systems and media as disclosed herein and include, without limitation known, any automated method operated by the skilled artisan, for example by automated immunohistochemical methods, or machines such as mass spectrometry.

Application of the Methods, Kits, Machines, Computer Systems, Computer Readable Media:

In the research context, embodiments of the invention may provide a method for drug screening and reporting of drug effects in preclinical and clinical trials. The inventive methods can be used to identify which subjects are likely to be responsive to a topo I inhibitor, assess the effectiveness of topo I inhibitors in a population of subjects alone or in combination with other anticancer drugs and other therapeutic agents, improve the quality and reduce costs of clinical trials, discover the subset of positive responders to a particular class of topoisomerase I inhibitor (i.e. stratifying patient populations), improve therapeutic success rates, and/or reduce sample sizes, trial duration and costs of clinical trials.

In the health care context, embodiments of the invention may provide a service to physicians that will enable the physicians to tailor optimal personalized patient therapies. For example, a biological sample taken from a subject can be sent by the pathologist and/or clinical oncologist to a laboratory facility, for example, one such lab is operated by Theranostics Health, LLC. The laboratory may analyze the phosphorylation status of topo I in the biological sample and provide a report to the physician or health care provider. The laboratory may provide the treating pathologist or clinical oncologist with a report indicating if the subject from which the biological sample was taken is responsive or unresponsive to a topo I inhibitor and optionally provide a listing the topo I inhibitors which can be used should the subject be identified as being responsive, or alternative anti-cancer agents which are not topo I inhibitors, or a list of topo I inhibitor sensitivity agents to be used in combination with a topo I inhibitor should the subject be identified to be unresponsive to a topo I inhibitor. This may enable a physician to tailor therapy to the individual subject's tumor or other disorder, prescribe the right therapy to the right patient at right time, provide a higher treatment success rate, spare the patient unnecessary toxicity and side effects, reduce the cost to patients and insurers of unnecessary or dangerous ineffective medication, and improve patient quality of life, eventually making cancer a managed disease, with follow up assays as appropriate. Physicians can use the reported information to tailor optimal personalized patient therapies instead of the current "trial and error" or one size fits all methods used to prescribe chemotherapy under current systems. The inventive methods may establish a system of personalized medicine.

In some embodiments of the present invention may be defined in any of the following numbered paragraphs:

1. A machine for obtaining data regarding a biological sample from a subject comprising:
   a. a biological sample container to hold the biological sample;
   b. a determination module configured to detect the presence of phosphorylation of a topoisomerase I polypeptide in the biological sample;
   c. a storage device configured to store data output from the determination module;
   d. a comparison module adapted to compare the data stored on the storage device with a control data, and
   e. a display module for displaying a page of retrieved content for the user on a client computer, wherein
      (i) the retrieved content is the presence of topoisomerase I polypeptide, and/or
      (ii) the retrieved content is the presence or absence of phosphorylation of the topoisomerase I polypeptide, and/or
      (iii) the retrieved content is the absence of phosphorylation of topoisomerase I and a signal that the subject likely to be responsive to topoisomerase I inhibitor; and/or
      (iv) the retrieved content is the presence of phosphorylation of topoisomerase I and a signal that the subject likely to be unresponsive to topoisomerase I inhibitor.

2. The machine of paragraph 1, wherein the determination module measures the level of phosphorylation of topoisomerase I polypeptide.

3. The machine of paragraph 1, wherein the determination module measures the level of phosphorylation of serine 10 (S10) of the topoisomerase I polypeptide.

4. The machine of paragraphs 2 of 3, wherein the level of phosphorylation is measured using a protein-binding moiety.

5. The machine of paragraph 4, wherein the determination module contacts the biological sample with at least one protein binding moiety.

6. The machine of paragraph 5, wherein the protein binding moiety is selected from the group consisting of; antibodies; recombinant antibodies, chimeric antibodies, tribodies, midibodies, protein-binding agents, small molecule, recombinant protein, peptides, aptamers, avimers and derivatives or fragments thereof.

7. The machine of paragraph 6, wherein the determination module detects the presence of phosphorylation of topoisomerase I using a method selected from the group consisting of; immunoblot analysis, immunohistochemical analysis; ELISA, isoform-specific chemical or enzymatic cleavage, protein array or mass spectrometry.

8. The machine of paragraph 1, wherein the biological sample comprises a cancer or at least one cancer cell.

9. The machine of paragraph 8, wherein the cancer cell is a cancer stem cell.

10. The machine of paragraph 1, wherein the biological sample is selected from the group consisting of: a tissue sample, a tumor sample, a biopsy sample, an ex vivo cultivated sample, a ex vivo cultivated tumor sample, a surgically dissected tissue sample, a blood sample, plasma sample, a cancer sample, a lymph fluid sample, a primary ascite sample.

11. The machine of paragraph 8, wherein the cancer is selected from the group consisting of: small cell lung cancer (SCLC), colon cancer, ovarian cancer, breast cancer and cervical cancer.

12. The machine of paragraph 8, wherein the cancer is a refractory cancer.

13. The machine of paragraph 8, wherein the cancer is selected from the group of: gastrointestinal cancer, prostate cancer, ovarian cancer, breast cancer, squamous cell carcinomas (SCC), squamous cell carcinomas (SCC) of the head, neck lung and esophagus, head and neck cancer, lung cancer, non-small cell lung cancer, cancer of the nervous system, brain cancer, bone-marrow cancer, bone cancer, kidney cancer, retina cancer, skin cancer, bladder cancer, colon cancer, esophageal cancer, testicular cancer, cervical cancer, liver cancer, renal cancer, pancreatic cancer, genital-urinary cancer, gastrointestinal, gum cancer, tongue cancer, kidney cancer, nasopharynx cancer, stomach cancer, endometrial cancer and bowel tumor cell cancer.

14. The machine of paragraph 11, wherein the breast cancer is a triple-negative subtype breast cancer; or a cancer which lacks the expression of estrogen receptor (ER), the progesterone receptor (PR) and lacks Her-2 expression.

15. The machine of paragraph 1, wherein a topoisomerase I inhibitor is camptothecin (CPT) or an analogue or mimetic thereof.

16. The machine of paragraph 1, wherein an analogue of CPT consist of the group consisting of: topotecan and irinotecan.

17. The machine of paragraph 1, wherein the subject is a subject identified to have, or likely to have cancer.

18. The machine of paragraph 1, where in the subject is a human subject.

19. A computer system for obtaining data regarding a biological specimen comprising:
(a) a determination module configured to receive phosphorylation information, wherein the phosphorylation information comprises:
    (i) the level of phosphorylation of topoisomerase I polypeptide; or
    (ii) whether there is phosphorylation on serine 10 (S10) of topoisomerase I;
(b) a storage device configured to store data output from the determination module;
(c) a comparison module adapted to compare the data stored on the storage device with reference data, and to provide a retrieved content, and
(d) a display module for displaying a page of the retrieved content for the user, wherein
    (i) the retrieved content is the presence of topoisomerase I polypeptide, and/or
    (ii) the retrieved content is the presence or absence of phosphorylation of the topoisomerase I polypeptide, and/or
    (iii) the retrieved content is the absence of phosphorylation of topoisomerase I and a signal that the subject is likely to be responsive to topoisomerase I inhibitor; and/or
    (iv) the retrieved content is the presence of phosphorylation of topoisomerase I and a signal that the subject is likely to be unresponsive to topoisomerase I inhibitor.

20. The computer system of paragraph 19, wherein the determination module measures the level of phosphorylation of topoisomerase I polypeptide.

21. The computer system of paragraph 19, wherein the determination module measures the level of phosphorylation of serine 10 (S10) of the topoisomerase I polypeptide.

22. The computer system of paragraphs 20 of 21, wherein the level of phosphorylation is measured using a protein-binding moiety.

23. The computer system of paragraph 22, wherein the determination module contacts the biological sample with at least one protein binding moiety.

24. The computer system of paragraph 23, wherein the protein binding moiety is selected from the group consisting of; antibodies; recombinant antibodies, chimeric antibodies, tribodies, midibodies, protein-binding agents, small molecule, recombinant protein, peptides, aptamers, avimers and derivatives or fragments thereof.

25. The computer system of paragraph 24, wherein the determination module detects the presence of phosphorylation of topoisomerase I using a method selected from the group consisting of; immunoblot analysis, immunohistochemical analysis; ELISA, isoform-specific chemical or enzymatic cleavage, protein array or mass spectrometry.

26. The computer system of paragraph 19, wherein the biological sample comprises a cancer or at least one cancer cell.

27. The computer system of paragraph 19, wherein a topoisomerase I inhibitor is camptothecin (CPT) or an analogue or mimetic thereof.

28. The computer system of paragraph 27, wherein an analogue of CPT consist of the group consisting of: topotecan and irinotecan.

29. The computer system of paragraph 19, wherein the subject is a subject identified to have, or likely to have cancer.

30. The computer system of paragraph 19, where in the subject is a human subject.

31. A computer readable medium having computer readable instructions recorded thereon to define software modules including a determination module and a comparison module for implementing a method on a computer, said method comprising:
(a) storing data about phosphorylation information of a topoisomerase I polypeptide, wherein the phosphorylation information comprises (i) the level of phosphorylation of topoisomerase I polypeptide; or
(ii) whether there is phosphorylation on serine 10 (S10) of topoisomerase I; output from the determination module
(b) comparing with the comparison module the data stored on the storage device with reference data, and to provide a retrieved content, and
(c) displaying the retrieved content for the user, wherein the phosphorylation level of a topoisomerase I polypeptide is a profile, wherein the profile is indicative of the responsiveness of a cancer to a topoisomerase I inhibitor; wherein the absence of detection of phosphorylation of a topoisomerase I polypeptide is indicative of a cancer likely to be responsive to a topoisomerase I inhibitor, and the presence of more than 10% phosphorylation is indicative that the cancer is likely to be non-responsive to a topoisomerase I inhibitor.

32. The computer readable medium of paragraph 31, wherein the determination module measures the level of phosphorylation of topoisomerase I polypeptide.

33. The computer readable medium of paragraph 31, wherein the determination module measures the level of phosphorylation of serine 10 (S10) of the topoisomerase I polypeptide.

34. The computer readable medium of paragraphs 32 and 33, wherein the level of phosphorylation is measured using a protein-binding moiety.

35. The computer readable medium of paragraph 34, wherein the determination module contacts the biological sample with at least one protein binding moiety.

36. The computer readable medium of paragraph 35, wherein the protein binding moiety is selected from the group consisting of; antibodies; recombinant antibodies, chimeric antibodies, tribodies, midibodies, protein-binding agents, small molecule, recombinant protein, peptides, aptamers, avimers and derivatives or fragments thereof.

37. The computer readable medium of paragraph 31, wherein the determination module detects the presence of phosphorylation of topoisomerase I using a method selected from the group consisting of; immunoblot analysis, immunohistochemical analysis; ELISA, isoform-specific chemical or enzymatic cleavage, protein array or mass spectrometry.

38. The computer readable medium of paragraph 31, wherein the biological sample comprises a cancer or at least one cancer cell.

39. The computer readable medium of paragraph 31, wherein a topoisomerase I inhibitor is camptothecin (CPT) or an analogue or mimetic thereof.

40. The computer readable medium of paragraph 39, wherein an analogue of CPT consist of the group consisting of: topotecan and irinotecan.

41. The computer readable medium of paragraph 31, wherein the subject is a subject identified to have, or likely to have cancer.

42. The computer readable medium of paragraph 31, where in the subject is a human subject.

43. The use of the machine of paragraph 1 to identify the likelihood of a cancer to be responsive to a topoisomerase I inhibitor, wherein a cancer is likely to be responsive to a topoisomerase I inhibitor when the machine displays from its display module the absence of phosphorylation of a topoisomerase I polypeptide.

44. The use of the machine of paragraph 1 to identify the likelihood of a cancer to be responsive to a topoisomerase I inhibitor, wherein a cancer is likely to be responsive to a topoisomerase I inhibitor when the machine displays from its display module the absence of phosphorylation of serine 10 (S10) on a topoisomerase I polypeptide.

45. The use of the computer system of paragraph 19 to identify the likelihood of a cancer to be responsive to a topoisomerase I inhibitor, wherein a cancer is likely to be responsive to a topoisomerase I inhibitor when the machine displays from its display module the absence of phosphorylation of a topoisomerase I polypeptide.

46. The use of the computer system of paragraph 19 to identify the likelihood of a cancer to be responsive to a topoisomerase I inhibitor, wherein a cancer is likely to be responsive to a topoisomerase I inhibitor when the machine displays from its display module the absence of phosphorylation of serine 10 (S10) on a topoisomerase I polypeptide.

47. The use of the computer readable medium of paragraph 31 to identify the likelihood of a cancer to be responsive to a topoisomerase I inhibitor, wherein a cancer is likely to be responsive to a topoisomerase I inhibitor when the machine displays from its display module the absence of phosphorylation of a topoisomerase I polypeptide.

48. The use of the computer readable medium of paragraph 31 to identify the likelihood of a cancer to be responsive to a topoisomerase I inhibitor, wherein a cancer is likely to be responsive to a topoisomerase I inhibitor when the machine displays from its display module the absence of phosphorylation of serine 10 (S10) on a topoisomerase I polypeptide.

49. A method of identifying the likelihood of a cancer to be unresponsive to a topoisomerase I inhibitor, the method comprising measuring the level of phosphorylation of topoisomerase I polypeptide in at least one cancer cell, wherein the presence of phosphorylation identifies the cancer as being more likely to be unresponsive to a topoisomerase inhibitor as compared to a cancer wherein the absence of phosphorylation of topoisomerase I is detected.

50. A method for treating cancer in a subject, the methods comprising:
(i) measuring the level of phosphorylation of topoisomerase I polypeptide in a biological sample comprising cancer cells obtained from the subject;
(ii) detecting the level of topoisomerase I polypeptide, wherein if the topoisomerase I polypeptide is phosphorylated the cancer is identified as being unresponsive to a topoisomerase I inhibitor, or wherein if the topoisomerase I polypeptide is not phosphorylated the cancer is identified as being likely to be responsive to a topoisomerase I inhibitor;
(iii) administering to a subject an anti-cancer agent other than a topoisomerase I inhibitor where the cancer is identified as being unresponsive to a topoisomerase I inhibitor.

51. The method of paragraphs 49 or 50, wherein the phosphorylation of the topoisomerase I polypeptide is phosphorylation of serine 10 (S10) of topoisomerase I polypeptide.

52. The method of paragraphs 49 or 50, wherein the topoisomerase I inhibitor is camptothecin (CPT) or an analogue or mimetic thereof.

53. The method of paragraph 52, wherein an analogue of CPT consist of the group consisting of: topotecan and irinotecan.
54. The method of paragraphs 49 or 50, wherein the subject is human.
55. A protein binding moiety with specific affinity for phosphorylated topoisomerase I, wherein the phosphorylated topoisomerase I comprises a phosphate group at the serine 10 (S10) amino acid residue.
56. The protein binding moiety of paragraph 55, wherein the protein binding moiety is an antibody or a fragment thereof.
57. The protein binding moiety of paragraph 55, wherein the protein binding moiety is selected from the group consisting of: antibodies; recombinant antibodies, chimeric antibodies, tribodies, midibodies, protein-binding agents, small molecule, recombinant protein, peptides, aptamers, avimers and derivatives or fragments thereof.
58. Use of a protein binding moiety of paragraph 55 to identify the likelihood of a cancer to be unresponsive to a topoisomerase I inhibitor according to the method of paragraph 49 or 50.
59. A kit comprising the protein binding moiety of paragraph 55.

EXAMPLES

The examples presented herein relate to the methods, kits, machines and computer systems and media to identify the presence of phosphorylation of a topoisomerase I polypeptide in a biological sample, in particular the presence of phosphorylation at the serine 10 (S10) residue of topo I polypeptide, and determination of responsiveness or efficacy to topoI inhibitors such as, for example but not limited to camptothecin (CPT), or CTP analogues such as topotecan and irinotecan and derivatives thereof. Throughout this application, various publications are referenced. The disclosures of all of the publications and those references cited within those publications in their entireties are hereby incorporated by reference into this application in order to more fully describe the state of the art to which this invention pertains. The following examples are not intended to limit the scope of the claims to the invention, but are rather intended to be exemplary of certain embodiments. Any variations in the exemplified methods which occur to the skilled artisan are intended to fall within the scope of the present invention.

Methods.

Tissue Culture: Human cervical carcinoma (HeLa) cells, MCF-7 breast cancer cells, BT-474 breast cancer cells and Mouse embryo fibroblasts (MEF) reconstituted for stable expression of DNA-PK (ScH8) and wild type MEF (ScSv3, DNA-PK −/−) were grown and maintained in Dulbecco's Modification of Eagle's Medium containing 10% fetal bovine serum, 2 mM L-Glutamine 100 units/mL of Streptomycin and 100 units/mL of Penicillin.

Cell Synchronization and Drug Treatment. MEF cells were phase-synchronized by serum starvation. Cells were incubated for 30 hours in Dulbecco's Modification of Eagle Medium containing 0.1% fetal bovine serum followed by 16 hour incubation in Medium containing 10% fetal bovine serum. Topo I inhibitor treatment was performed using a 25 μM concentration of Irinotecan (Sigma). Transient transfection of cell lines for BRCA1 and BARD1 expression was performed using the Geneporter 2 transfection kit (GenLantis).

BRCA1 Silencing: Virus Production. BRCA1 shRNA and control plasmids were purchased from Open Biosystems (Huntsville, Ala.). All pLKO.1 plasmids were developed by the RNAi consortium (Boston, Mass.). Packaging and envelope plasmids were obtained from Addgene (Cambridge, Mass.). To produce virus, pLKO.1 plasmids, the packaging plasmid psPAX2 and the envelope plasmid pCMV-VSVg were simultaneously transfected into 293FT cells (Invitrogen). 18 hours after transfection cells were refed DMEM+ 30% FBS. Virus containing media was subsequently removed in 2 aliquots at 24 and 48 hours and frozen at −80° C.

Viral Transduction. Virus transduction was completed by adding the appropriate amount of virus-containing media and 8 μg/mL Hexadimethrine Bromide to growth media containing non-attached cells. Upon completion of transduction and attachment 24 hours later, virus-containing media was removed and replaced with fresh media containing 2.5 μg/mL puromycin. Transduced cells were selected for at least 2 days before use. Transduction efficiencies typically exceeded 95% in most cell types. The following TRC designated plasmids were tested: TRCN0000039833, TRCN0000039834, TRCN0000039835, TRCN0000039836, and TRCN0000039837. It was determined that TRCN0000039834 resulted in the greatest knockdown.

Immunoprecipitation and immunoblot analysis: Cell lysates were prepared for immunoprecipitation and soluble proteins were incubated with anti-BRCA1 or anti-topoI (Topogen, Inc.). The immunoprecipitates were subjected to immunoblotting with anti-BRCA1 or anti-topoI. Antigen-antibody complexes were visualized by enhanced chemiluminescence (ECL detection system, GE, Piscataway, N.J.).

Isolation of topoI associated proteins: GST Pull down: GST bead preparation. Purified GST (control) and GST-topo I were eluted from glutathione sepharose beads by elution buffer (10 mM reduced glutathione, 150 mM NaCl, 50 mM Tris, pH 8.0). The eluted protein was dialyzed in PBS for twelve hours at 4° C. Protein concentration of dialyzed samples was determined by modified Bradford reagent (Bio-Rad). The eluted and dialyzed GST and GST-topo I protein was incubated with glutathione sepharose beads. For 100 μl of GS beads 150 μg of protein were incubated at 4° C. for two hours in PBS. A total of 1 ml beads were incubated for one pull down experiments. In our experiments 1.5 gm of GST and GST-topo I were reattached to 1 ml of GS beads. The reattached PBS equilibrated GST and GST-topo I beads were poured into two empty columns, the columns were washed with PBS and used for pull down experiments.

Nuclear isolation. 4×10 8 cells were harvested. The cell pallet was resuspended in buffer A (10 mM Hepes pH7.8, 10 mM KCl, 0.1 mM EDTA, 1 mM DTT) with protease inhibitor cocktail (Roche). Cells were incubated for 10 minutes on ice and centrifuged for 5 minutes at 1500 g. The cells were resuspended in buffer A and homogenized (10-12 strokes) with type A hand held homogenizer. The homogenate was centrifuged at 1500 g for five minutes; nuclear pallet was collected for protein extraction.

Nuclear extract. The nuclei was resuspended in buffer B (50 mM Hepes pH 7.8, 420 mM KCl, 0.1 mM EDTA, 5 mM $MgCl_2$, 1 mM DTT and 2% glycerol with protease inhibitor cocktail). The resuspended nuclei were rotated for 30 minutes at 4° C. and the nuclear extract was collected after centrifugation at 24,000 g for 30 minutes. The nuclear extract was dialyzed in buffer C (30 mM Tris pH 7.4, 5 mM $MgCl_2$, 1 mM EDTA and 1 mM DTT) for 20 hours with two buffer changes.

Pull Down Experiment. Equal volume of the dialyzed nuclear extract was passed through GST and GST-topo I columns after equilibrating them with buffer C. The step was repeated three times to provide sufficient time for proteins in the extract to bind with GST and GST-topo I. The column was washed with ten volume of buffer C. After the completion of the wash, 1 ml of buffer D (buffer C+150 mM NaCl) was added to elute the interacting proteins. The eluted proteins were collected in five fractions of 200 µl each. The proteins were further eluted and fractionated with 1 ml of buffer E (buffer C+500 mM NaCl). The fractions containing interacting proteins were analyzed by SDS-PAGE and silver staining.

Sample Preparation for Analysis by MALDI-TOF-MS: Proteins from coomasie/silver stained gels were excised and processed for in gel trypsin digestion. Briefly, the gels were cut into small but uniform pieces. The gel pieces were dehydrated by acetonitrile and then rehydrated with 100 mM ammonium bicarbonate. To protect peptides from oxidation, 100 mM Dithiothreitol was added to the ammonium bicarbonate and incubated at 56° C. for one hour. Protecting the amino terminus protection was accomplished by blocking the gel with 10 mM iodoacetamide in 100 mM ammonium bicarbonate. The gel pieces were washed with ammonium bicarbonate and dehydrated using acetonitrile. Blocking and washing were repeated twice each. After complete dehydration with acetonitrile, gel pieces were suspended in 12.5 ng/uL trypsin in 50 mM ammonium bicarbonate. The in-gel digestion was carried at 37° C. for 10-12 hours. Peptides were extracted from gel pieces in 50% acetonitrile and 5% formic acid. The extract was concentrated under reduced pressure and finally desalted by C-18 containing Zip-Tip (Millipore, Mass.). Samples were suspended in an α-cyanol matrix and analyzed by matrix assisted laser desorption/ionization-time of flight-mass spectroscopy (MALDI-TOF-MS) using a Voyager DE-PRO (Perceptive Biosystem Inc, Framingham, Mass.). The proteins were identified by mass fingerprinting using database analysis. Selected peptides were further analyzed by sequencing using PSD.

Identification of topoI interacting proteins: The proteins specifically associated with topoI were identified by mass spectrometry. Analysis of these proteins by mass spectrometry led us to identify more than nine proteins. Prominent among these proteins were Ku70/Ku80 heterodimer and BRCT domain of BRCA1. The protein identification was based on the percentage of representative peptide coverage and also sequence of peptides.

In Vitro Phosphorylation: Purified GST-topoI (55) was incubated with DNA-PK in kinase buffer (20 mM Tris-HCl, pH 7.4, 10 mM MgCl$_2$ and 10 mM MnCl$_2$) containing [γ-$^{32}$P] ATP or cold ATP for 30 min at 30° C. The reaction products were analyzed by SDS-PAGE and autoradiography.

Identification of the DNA-PK mediated topoI phosphorylation sites: To identify the in vitro phosphorylation site, GST-topoI was incubated with purified Ku-DNA-PK in DNA-PK kinase buffer in the presence of ATP. The kinase reaction was carried out at 30° C. for 30 min. The reaction product was analyzed by SDS-PAGE and coomassie staining. GST-topoI protein band identified by staining was cut in to small pieces and processed for trypsin digestion. The trypsin digested topoI peptides were analyzed by MS. The phosphopeptides were enriched by IMAC column and then analyzed by LC-MS-MS (Q-Star, ABI).

In Vitro Ubiquitination: Reactions on 700 ng of topo I were carried out in 10 mM HEPES (pH 7.9), 0.5 mM EDTA, 5 mM MgCl2, 2 mM NaF, 2 mM ATP, 60 mM KCl, 1 µM ubiquitin, 200 nM E1-His, 5 µM UbcH5c-His (E2) with 200 to 400 ng of BRCA1-Flag/BARD1 (E3). Negative controls were also established in the absence of BRCA1-Flag/BARD1. Reactions were resolved by SDS-PAGE and observed by autoradiography.

Example 1

Human topoisomerase I (topoI) is an essential and ubiquitous enzyme that is involved in various DNA transactions, and is a target of a class of anti-neoplastic drugs such as camptothecin (CPT) and CPT analogues such as topotecan and irinotecan, which are used in the clinic for the treatment of SCLC, colon and ovarian cancer and in several refractory cancers, including breast and cervical. However, like most cancer drugs, only 30% of patients respond to topo I inhibitors. Because the level of the topoI protein is high in most solid tumors, topo I levels can not be used as a predictive marker to determine efficacy of topo I inhibitors. The inventors have demonstrated herein that DNA-PK dependent phosphorylation of topoI initiates the ubiquitination of topo I and also BRCA1 is the E3 ligase. The inventors have discovered that the presence of phosphorylation at the serine 10 amino acid residue of topoI determines the rate of ubiquitination and degradation of topoI in the response to CPT. Accordingly, the inventors have discovered that the presence of phosphorylation at the serine 10 (S10) residue of topo I polypeptide results in degradation of topo I and thus a topo I inhibitor is likely to be ineffective. Thus, the inventors have identified a prognostic marker to identify if a topo I inhibitor is likely to be effective, where the absence of phosphorylation at the serine 10 (S10) amino acid residue identifies that a topo I inhibitor is likely to be effective in a biological sample (i.e. the topo I inhibitor is likely to result to cell death) whereas the presence of phosphorylation at serine 10 (S10) identifies that a topo I inhibitor is likely not to be effective in a biological sample (i.e. a topo I inhibitor is likely not to result in cell death).

Figure 2A:
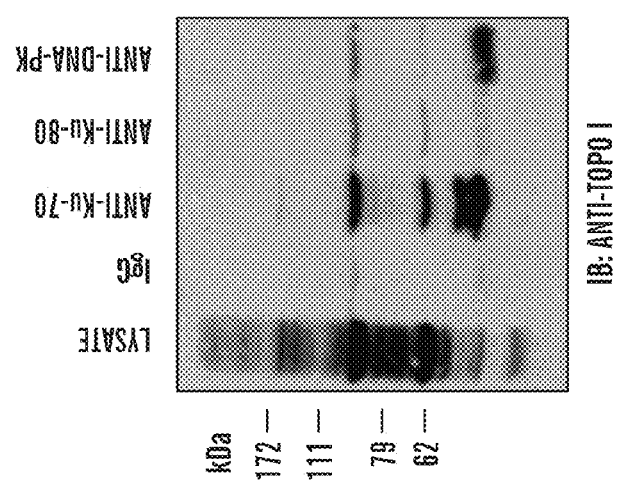
FIGS. 2A-2E shows TopoI associates with Ku-DNA-PK complex and with BRCA1.
Figure 2B:
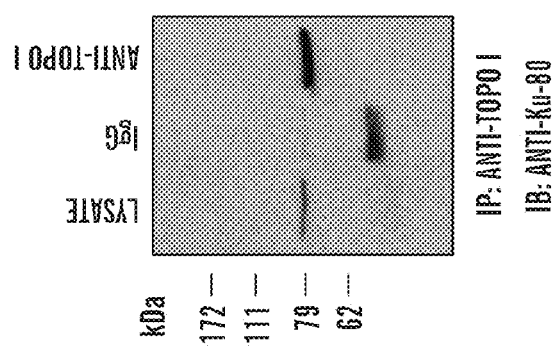
Figure 2C:
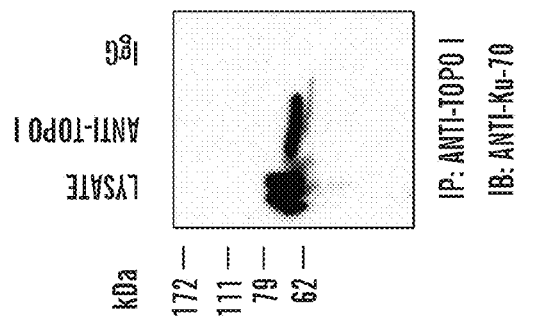
Figure 2E:
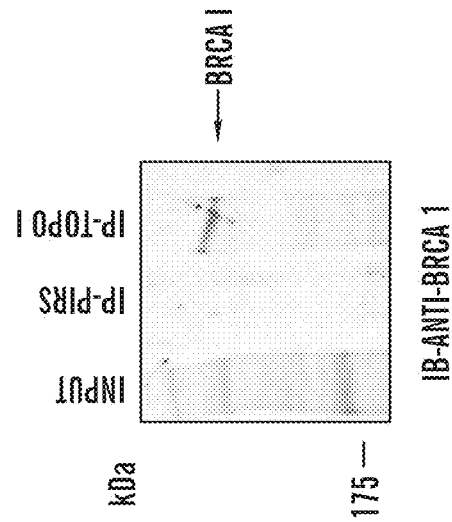
Figure 2D:
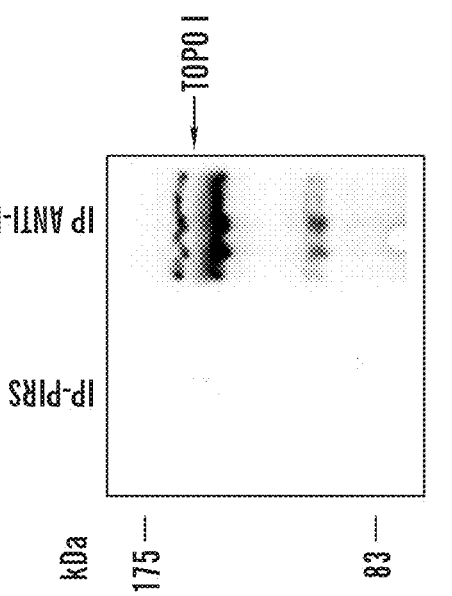

Association of TopoI with DNA-PK-Ku complex and BRCA1. Proteins specifically associated with topoI were identified by mass spectrometry. Analysis of these proteins by mass spectrometry led us to identify more than nine proteins. Prominent among these proteins were Ku70/Ku80 heterodimer and BRCT domain of BRCA1. Isolation of nucleolin as one of the topoI interacting proteins validated our technique as it confirmed our earlier finding (Bharti et al 1995). The inventors discovered that TopoI associates with Ku 70/80 (FIGS. 1A-1E) and associates with the Ku-DNA-PK complex as demonstrated by pull down experiments and immunoprecipitation analysis (FIGS. 2A-2C).

Example 2

Figure 3A:
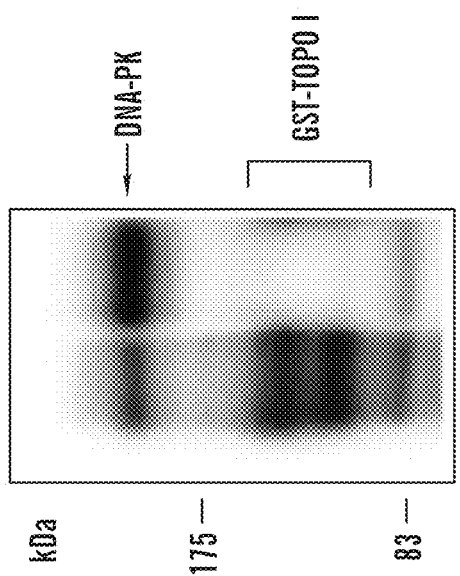
FIGS. 3A-3B shows DNA-PK phosphorylates topoI. Purified GST-topoI (5 μg; left lane) was incubated with DNA-PK in kinase buffer (20 mM Tris-HCl, pH 7.4, 10 mM MgCl$_2$ and 10 mM MnCl$_2$) containing [γ-32P]ATP or cold ATP for 30 min at 30° C.
Figure 3B:
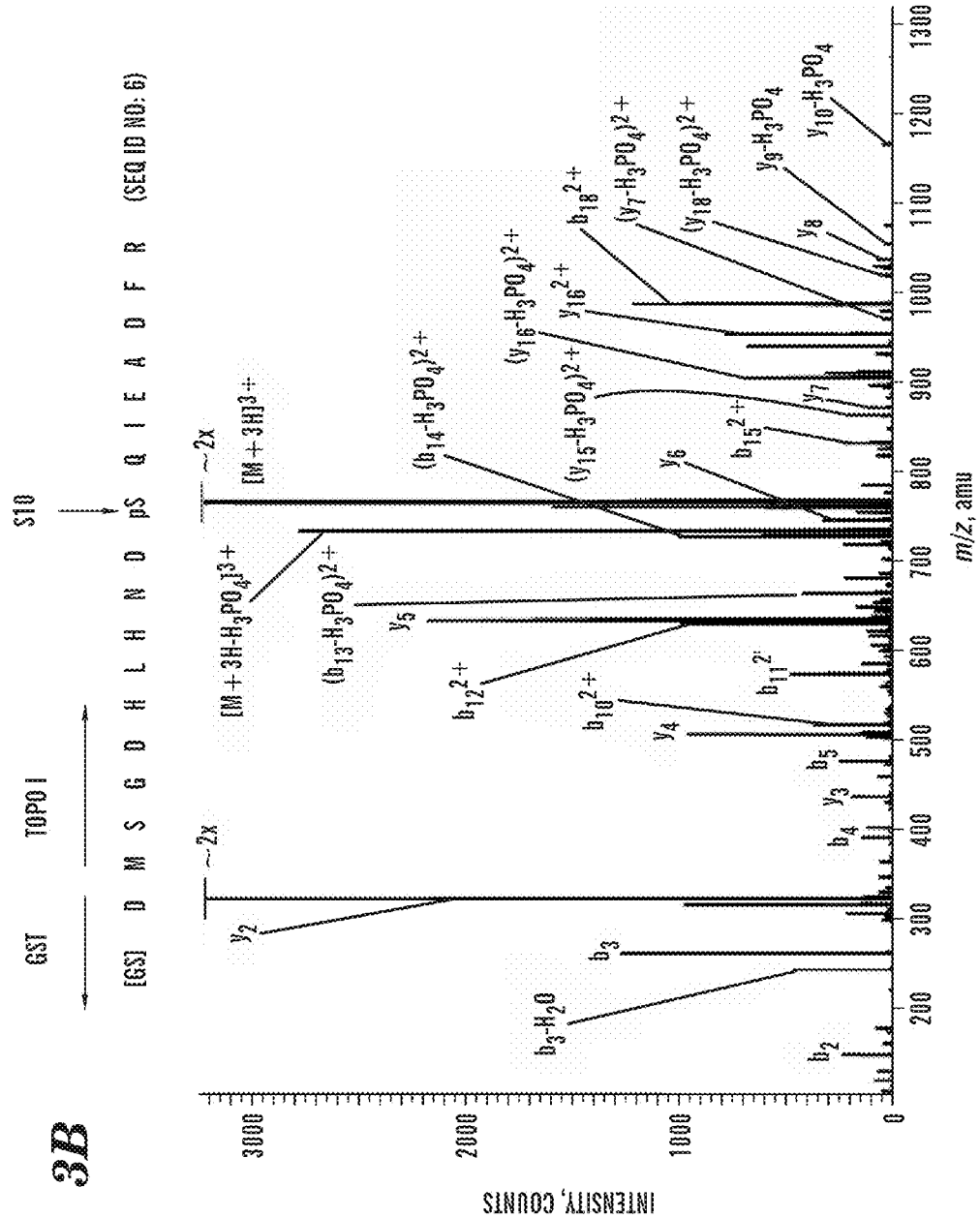

Topo I is Phosphorylated by DNA-PK at site S10. Analysis of the reaction product of topoI phosphorylation with DNA-PK by SDS-PAGE and autoradiography demonstrated that DNA-PK phosphorylates topoI in vitro. GST was not a substrate of DNA-PK. In the absence of topoI significant higher level of auto-phosphorylation of DNA-PK was also observed. Further analysis of phosphorylated topoI by mass spectrometry revealed that S10 of topoI is phosphorylated by DNA-PK. FIG. 3 shows that TopoI is phosphorylated on S10.

Figure 4D:
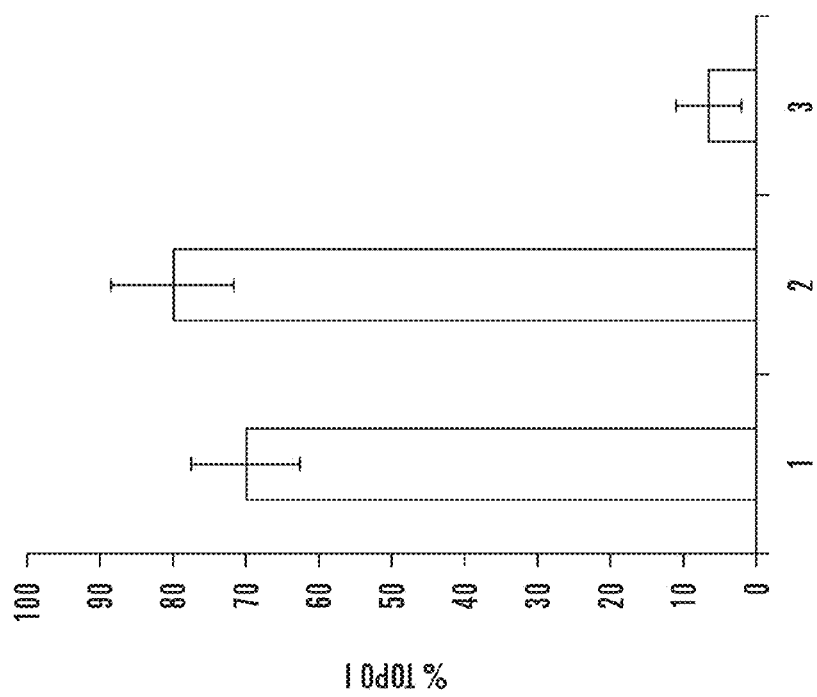
Figures 5A, 5B:
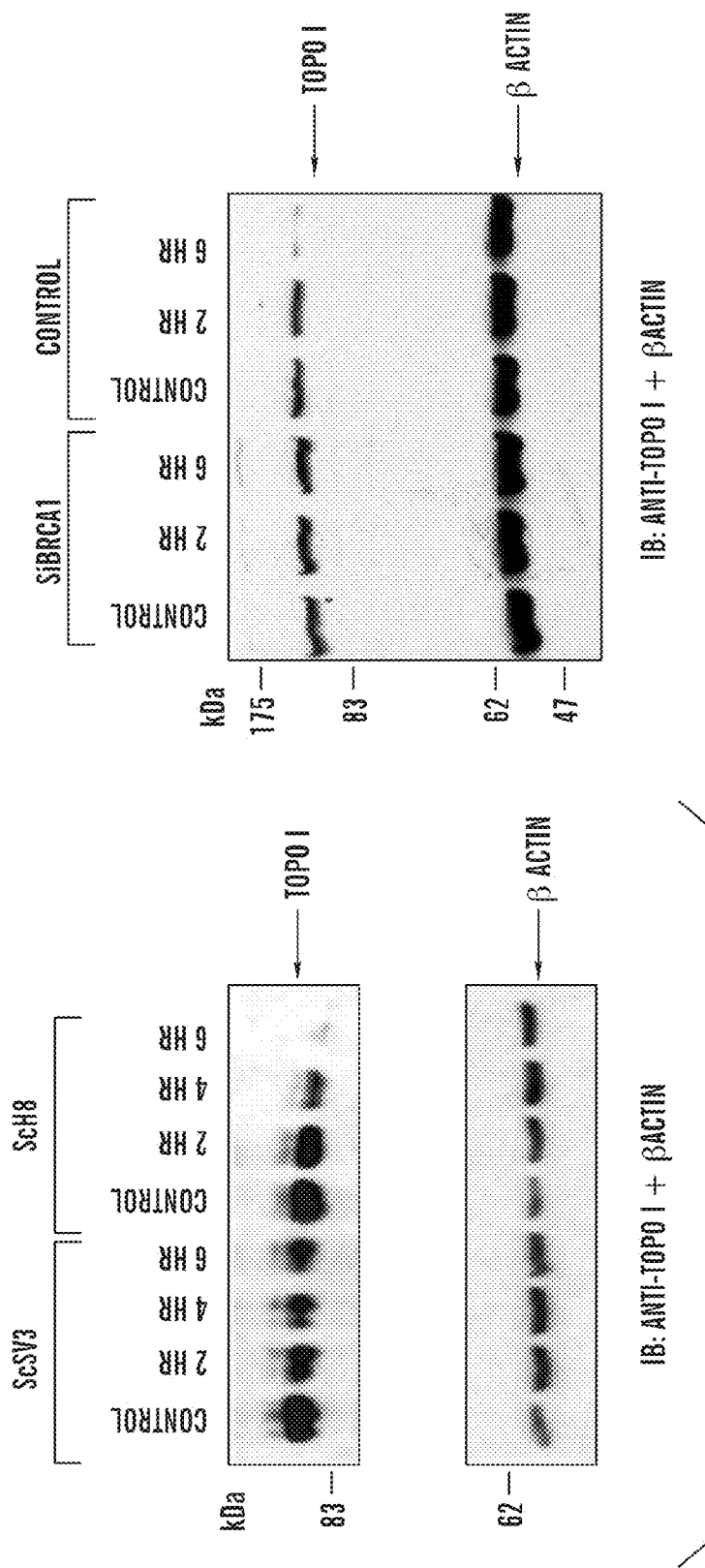
FIGS. 5A-5C shows BRCA1 dependent ubiquitination and proteosomal degradation of topo I in BT 474 cells.
Figure 5C:
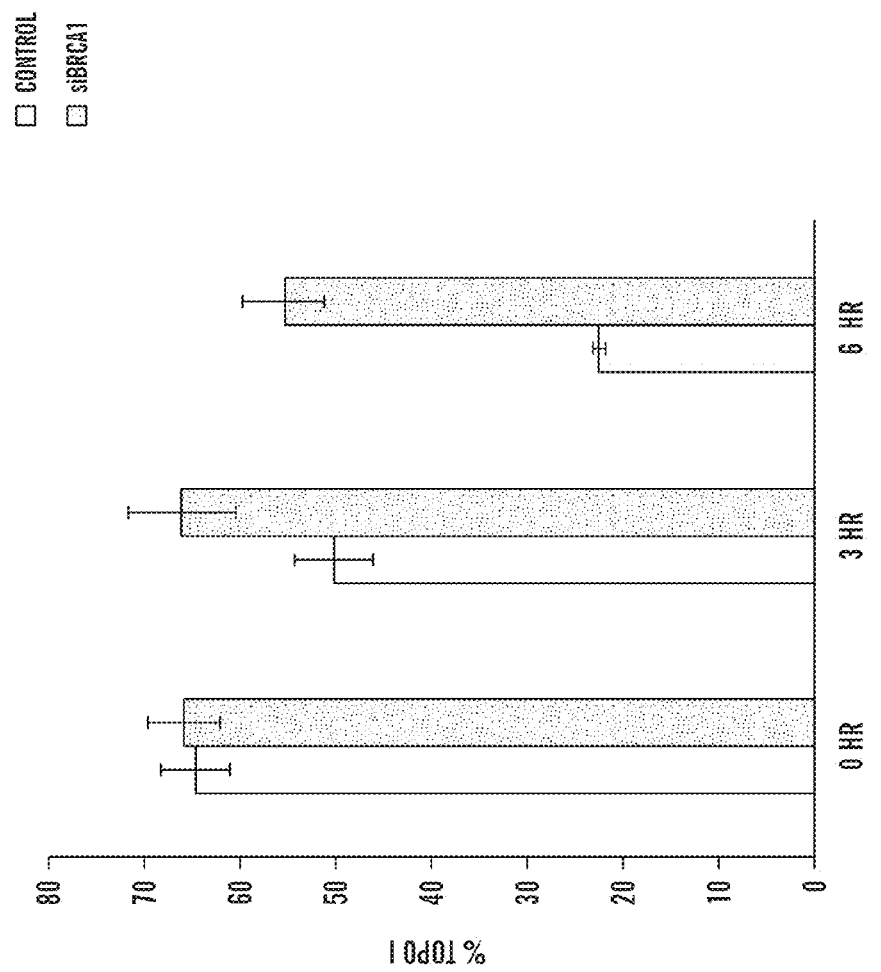
Figure 6B:
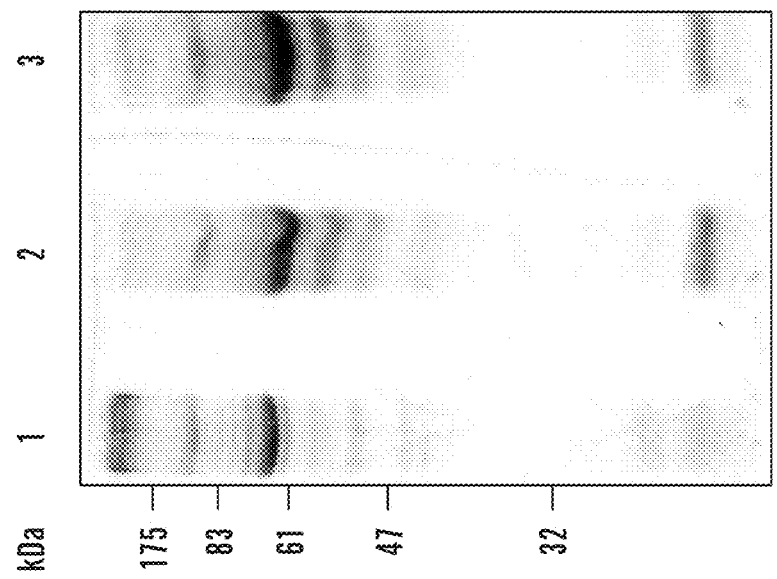
FIGS. 6A-6B shows S10A mutant is not phosphorylated by DNA-PK. Purified GST-topoI (5 μg; left lane) and GST-topoI S10A (mutant) (right lane) was incubated with DNA-PK in kinase buffer (20 mM Tris-HCl, pH 7.4, 10 mM MgCl$_2$ and 10 mM MnCl$_2$) containing [γ-32P]ATP or cold ATP for 30 min at 30° C. Figure A shows SDS-PAGE analysis of the reaction products and autoradiography.
Figure 6A:
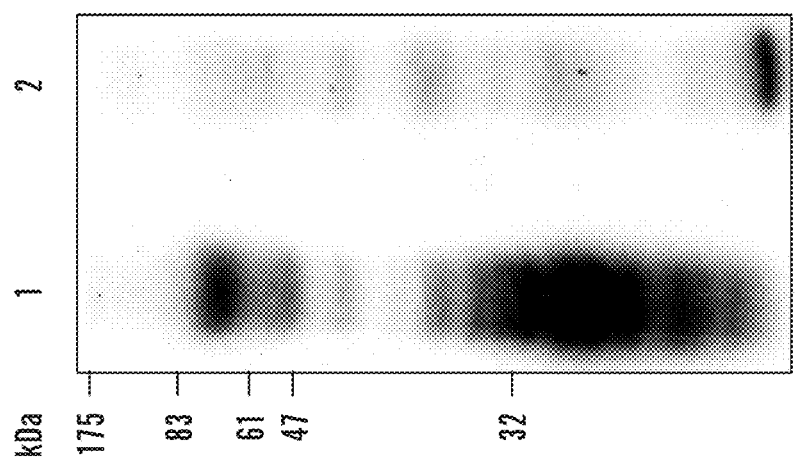
Figure 7B:
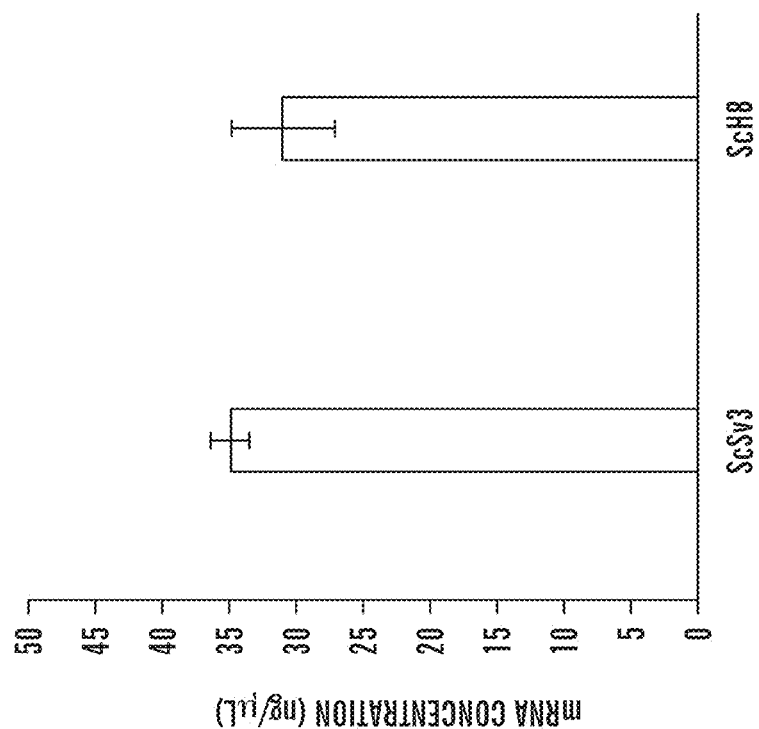
FIGS. 7A-7B shows status of topoI in DNA-PK deficient cells.
Figure 7A:
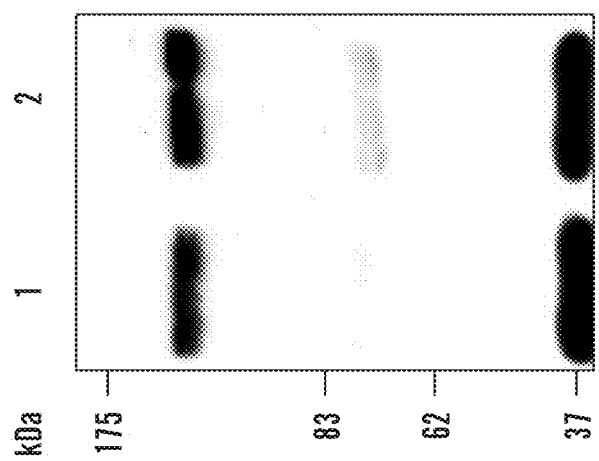
Figure 8B:
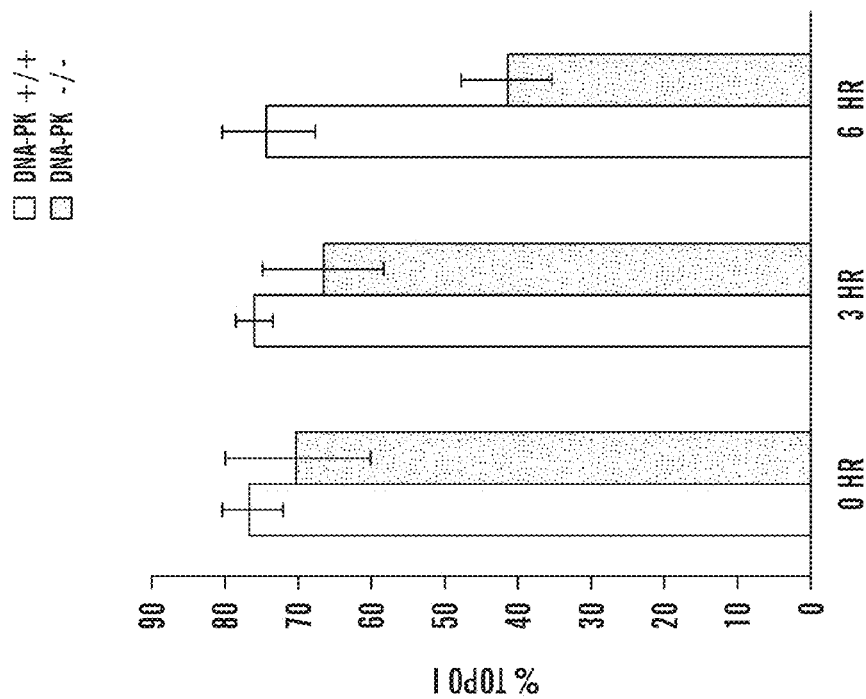
FIGS. 8A-8D shows topoI down regulation in DNA-PK deficient cells (SvSC3) and sensitivity to topoisomerase I inhibitor CPT.
Figure 8A:
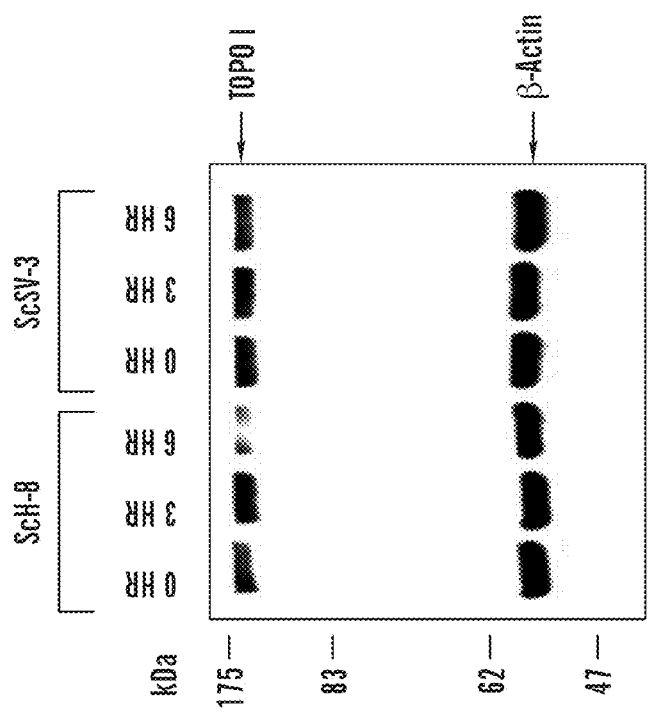
Figure 8C:
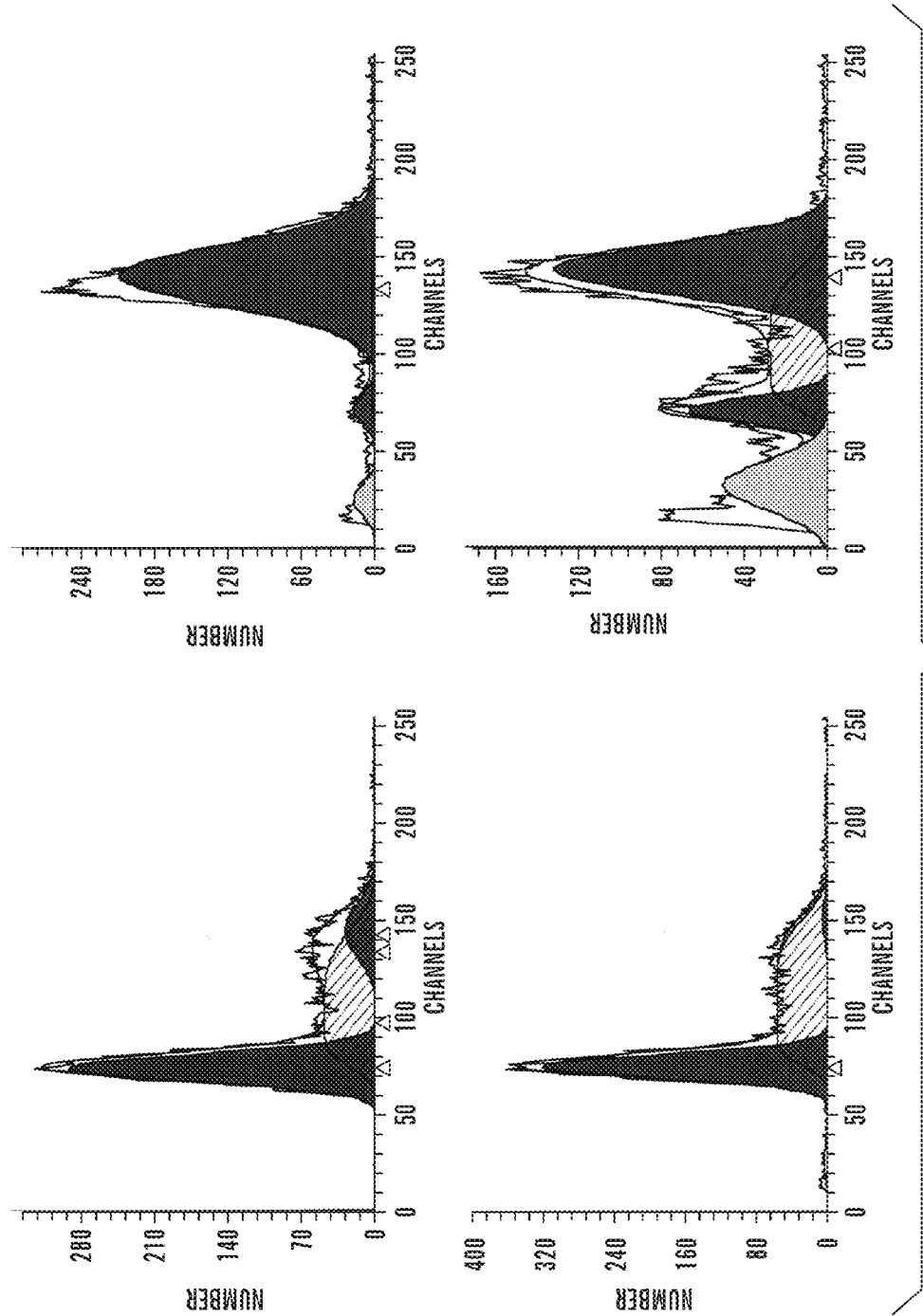
Figure 8D:
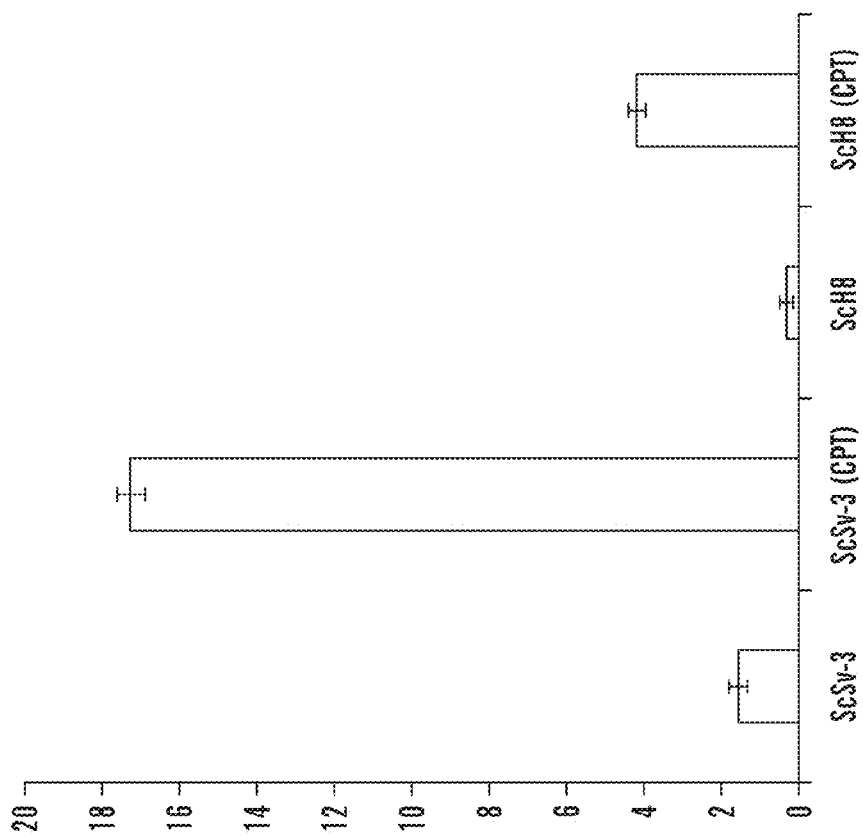
Figure 9:
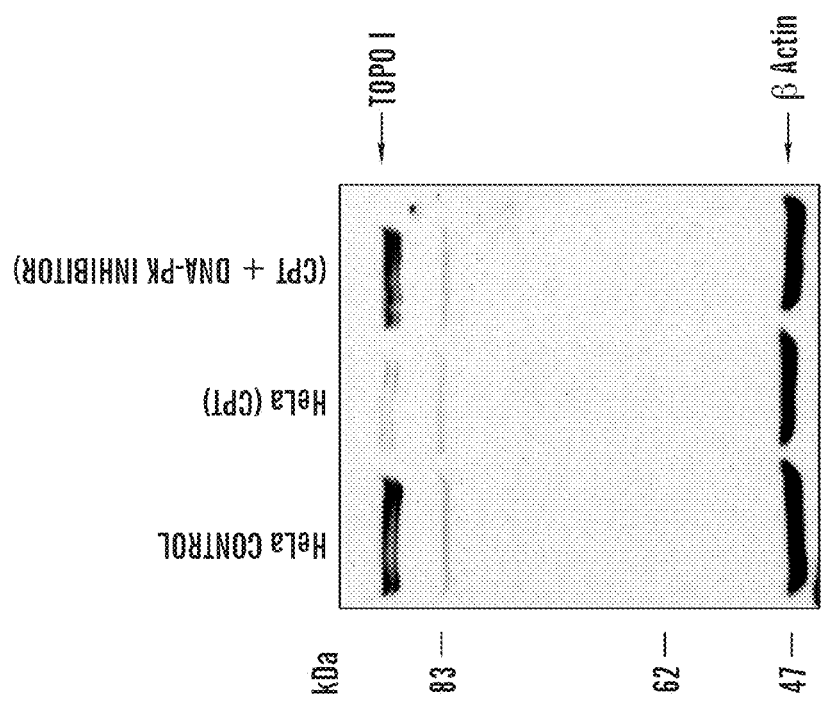
FIG. 9 shows DNA-PK inhibitor obliterates CTP induced topoI downregulation by UPP.
Figure 11B:
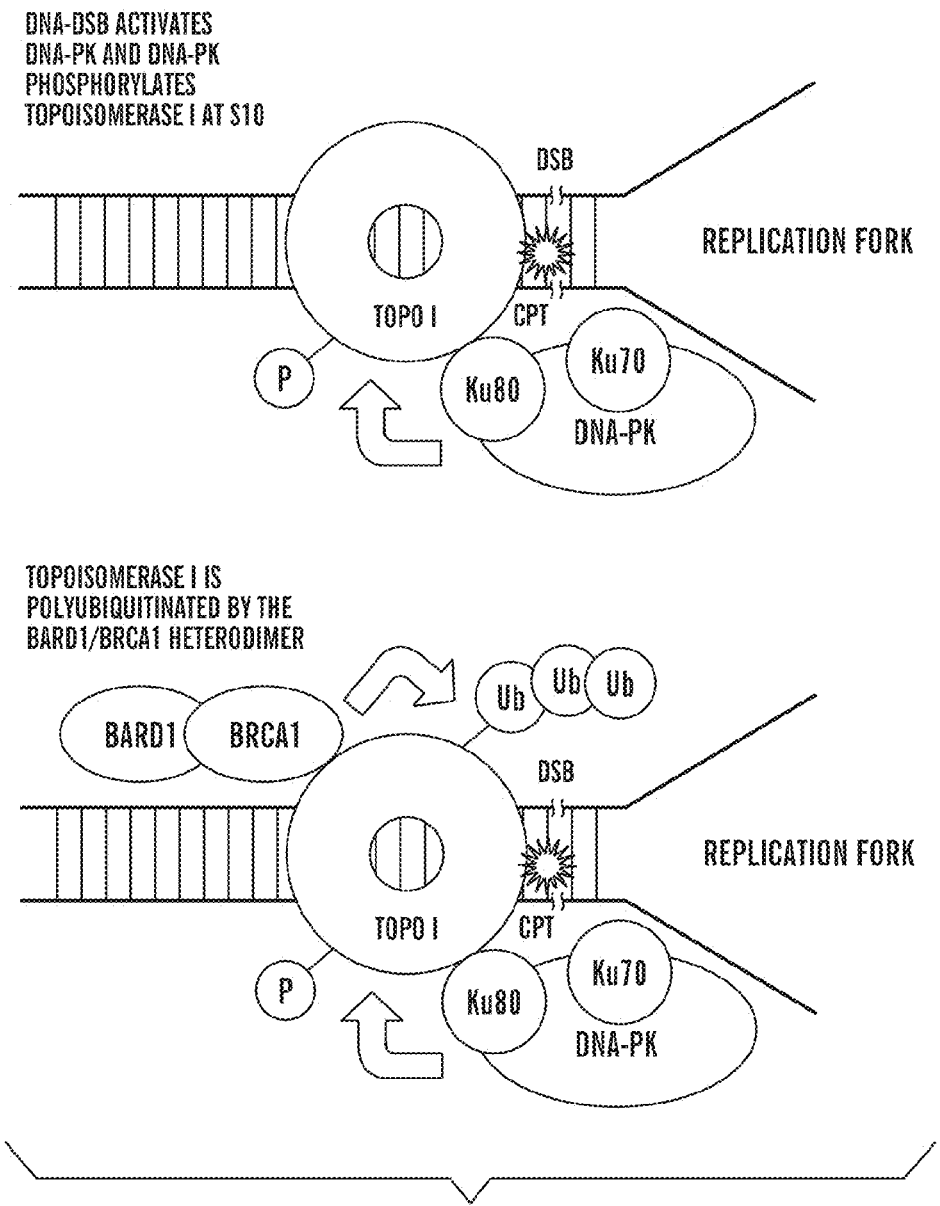

BRCA1 acts as an E3 Ubiquitin Ligase for TopoI, for which Phosphorylation is Required. In vitro experiments shown in FIG. 4 demonstrate that phosphorylation of topo I by DNA-PK up-regulates ubiquitination. The inventors investigated if BRCA1, a known E3 ubiquitin ligase could act as the E3 ubiquitin ligase for topo I. Immunoblot analysis of the product of in vitro topoI ubiquitination reaction showed ubiquitination of topo I by BRCA1. The inventors confirmed that ubiquitination was the result of the E3 ligase activity of the BARD1/BRCA1 heterodimer, as determined by the enhanced rate of down-regulation of GFP-topoI in cells with the over expression of BARD1/BRCA1.

Example 3

Down-Regulation of TopoI in Response to CPT is Mediated by DNA-PK and BRCA1.

Response to CPT has been shown to be linked to the ubiquitination and consequent down regulation of topoI (Desai et al., J Biol Chem.; 272(39):24159-64. 1997). The inventors demonstrated by the analysis of topo I levels of DNA-PK deficient and efficient cells in response to CPT, a significantly higher rate of topoI down-regulation in DNA-PK +/+ cells. ScH8 cells treated with CPT showed a complete degradation of topoI at six hours however more than 50% topoI remained intact in ScSV3 cells, actin level remain similar in these cells. Using DNA relaxation assays of nuclear extract from these cells, the inventors demonstrated that there was no appreciable difference in topoI activity in these two cell lines (data not shown). The inventors also demonstrated that there was a similar level of the relative total topo I protein versus topo I mRNA levels in these cells. The inventors demonstrated a decrease in the rate of topoI down-regulation in BRCA1-silenced Hela cells. To further observe the interaction between topoI and BRCA1 in response to CPT treatment, the inventors performed co-immunostaining with GFP-topoI and BRCA1 and determined that GFP-topoI and BRCA1 colocalized in DNA repair foci in response to treatment with CPT.

REFERENCES

All references cited herein in the specification and examples are incorporated herein in their entirety by reference.

Bharti A K, Olson M O, Kufe D W, Rubin E H. J Biol Chem. 271(4):1993-7.1996

Yu D, Khan E, Khaleque M A, Lee J, Laco G, Kohlhagen G, Kharbanda S, Cheng Y C, Pommier Y, Bharti A. J Biol Chem.; 279(50):51851-61. 2004

Desai S D, Liu L F, Vazquez-Abad D, D'Arpa P. J Biol Chem.; 272(39):24159-64. 1997

```
SEQUENCE LISTING:
                                                                SEQ ID NO: 1
MSGDHLHNDpSQIEADFR

SEQ ID NO: 2
MSGDHLHNDSQIEADFRLNDSHKHKDKHKDREHRHKEHKKEKDR

EKSKHSNSEHKDSEKKHKEKEKTKHKDGSSEKHKDKHKDRDKEKRKEEKVRASGDAKI

KKEKENGFSSPPQIKDEPEDDGYFVPPKEDIKPLKRPRDEDDADYKPKKIKTEDTKKE

KKRKLEEEEDGKLKKPKNKDKDKKVPEPDNKKKKPKKEEEQKWKWWEEERYPEGIKWK

FLEHKGPVFAPPYEPLPENVKFYYDGKVMKLSPKAEEVATFFAKMLDHEYTTKEIFRK

NFFKDWRKEMTNEEKNIITNLSKCDFTQMSQYFKAQTEARKQMSKEEKLKIKEENEKL

LKEYGFCIMDNHKERIANFKIEPPGLFRGRGNHPKMGMLKRRIMPEDIIINCSKDAKV

PSPPPGHKWKEVRHDNKVTWLVSWTENIQGSIKYIMLNPSSRIKGEKDWQKYETARRL

KKCVDKIRNQYREDWKSKEMKVRQRAVALYFIDKLALRAGNEKEEGETADTVGCCSLR

VEHINLHPELDGQEYVVEFDFLGKDSIRYYNKVPVEKRVFKNLQLFMENKQPEDDLFD

RLNTGILNKHLQDLMEGLTAKVFRTYNASITLQQQLKELTAPDENIPAKILSYNRANR

AVAILCNHQRAPPKTFEKSMMNLQTKIDAKKEQLADARRDLKSAKADAKVMKDAKTKK

VVESKKKAVQRLEEQLMKLEVQATDREENKQIALGTSKLNYLDPRITVAWCKKWGVPI

EKIYNKTQREKFAWAIDMADEDYEF

SEQ ID NO: 3
  1 caaatgcgaa cttaggctgt tacacaactg ctggggtctg ttctcgccgc ccgcccggca 61 gtcaggcagc gtcgccgccg tggtagcagc ctcagccgtt tctggagtct cgggcccaca 121 gtcaccgccg cttacctgcg cctcctcgag cctccggagt ccccgtccgc ccgcacaggc 181 cggttcgccg tctgcgtctc ccccacgccg cctcgcctgc cgccgcgctc gtccctccgg 241 gccgacatga gtgggggacca cctccacaac gattcccaga tcgaagcgga tttccgattg 301 aatgattctc ataaacacaa agataaacac aaagatcgag aacaccggca caagaacac 361 aagaaggaga aggaccggga aaagtccaag catagcaaca gtgaacataa agattctgaa 421 aagaaacaca aagagaagga gaagaccaaa cacaaagatg gaagctcaga aaagcataaa 481 gacaaacata aagacagaga caaggaaaaa cgaaaagagg aaaaggttcg agcctctggg 541 gatgcaaaaa taagaaggag gaaggaaaat ggcttctcta gtccaccaca aattaaagat
```

-continued

```
 601 gaacctgaag atgatggcta ttttgttcct cctaaagagg atataaagcc attaaagaga
 661 cctcgagatg aggatgatgc tgattataaa cctaagaaaa ttaaaacaga agataccaag
 721 aaggagaaga aaagaaaact agaagaagaa gaggatggta aattgaaaaa acccaagaat
 781 aaagataaag ataaaaaagt tcctgagcca gataacaaga aaaagaagcc gaagaaagaa
 841 gaggaacaga agtggaaatg gtgggaagaa gagcgctatc ctgaaggcat caagtggaaa
 901 ttcctagaac ataaaggtcc agtatttgcc ccaccatatg agcctcttcc agagaatgtc
 961 aagtttttatt atgatggtaa agtcatgaag ctgagcccca agcagagga agtagctacg
1021 ttctttgcaa aaatgctcga ccatgaatat actaccaagg aaatatttag gaaaaatttc
1081 tttaaagact ggagaaagga aatgactaat gaagagaaga atattatcac caacctaagc
1141 aaatgtgatt tacccagat gagccagtat ttcaaagccc agacggaagc tcggaaacag
1201 atgagcaagg aagagaaact gaaaatcaaa gaggagaatg aaaaattact gaaagaatat
1261 ggattctgta ttatggataa ccacaaagag aggattgcta acttcaagat agagcctcct
1321 ggacttttcc gtggccgcgg caaccacccc aagatgggca tgctgaagag acgaatcatg
1381 cccgaggata taatcatcaa ctgtagcaaa gatgccaagg ttccttctcc tcctccagga
1441 cataagtgga agaagtccg gcatgataac aaggttactt ggctggtttc ctggacagag
1501 aacatccaag gttccattaa atacatcatg cttaacccta gttcacgaat caagggtgag
1561 aaggactggc agaaatacga gactgctcgg cggctgaaaa aatgtgtgga caagatccgg
1621 aaccagtatc gagaagactg gaagtccaaa gagatgaaag tccggcagag agctgtagcc
1681 ctgtacttca tcgacaagct tgctctgaga gcaggcaatg aaaaggagga aggagaaaca
1741 gcggacactg tgggctgctg ctcacttcgt gtggagcaca tcaatctaca cccagagttg
1801 gatggtcagg aatatgtggt agagtttgac ttcctcggga aggactccat cagatactat
1861 aacaaggtcc tgttgagaa acgagttttt aagaacctac aactatttat ggagaacaag
1921 cagcccgagg atgatctttt tgatagactc aatactggta ttctgaataa gcatcttcag
1981 gatctcatgg agggcttgac agccaaggta ttccgtacat acaatgcctc catcacgcta
2041 cagcagcagc taaaagaact gacagccccg gatgagaaca tcccagcgaa gatcctttct
2101 tataaccgtg ccaatcgagc tgttgcaatt ctttgtaacc atcagagggc accaccaaaa
2161 acttttgaga agtctatgat gaacttgcaa actaagattg atgccaagaa ggaacagcta
2221 gcagatgccc ggagagacct gaaaagtgct aaggctgatg ccaaggtcat gaaggatgca
2281 aagacgaaga aggtagtaga gtcaaagaag aaggctgttc agagactgga ggaacagttg
2341 atgaagctgg aagttcaagc cacagaccga gaggaaaata aacagattgc cctgggaacc
2401 tccaaactca attatctgga ccctaggatc acagtggctt ggtgcaagaa gtggggtgtc
2461 ccaattgaga agatttacaa caaaacccag cgggagaagt ttgcctgggc cattgacatg
2521 gctgatgaag actatgagtt ttagccagtc tcaagaggca gagttctgtg aagaggaaca
2581 gtgtggtttg ggaaagatgg ataaactgag cctcacttgc cctcgtgcct ggggagaga
2641 ggcagcaagt cttaacaaac caacatcttt gcgaaaagat aaacctggag atattataag
2701 ggagagctga gccagttgtc ctatggacaa cttatttaaa aatatttcag atatcaaaat
2761 tctagctgta tgatttgttt tgaattttgt ttttattttc aagagggcaa gtggatggga
2821 atttgtcagc gttctaccag gcaaattcac tgtttcactg aaatgtttgg attctcttag
2881 ctactgtatg caaagtccga ttatattggt gcgtttttac agttagggtt ttgcaataac
2941 ttctatattt taatagaaat aaattcctaa actcccttcc ctctctccca tttcaggaat
3001 ttaaaattaa gtagaacaaa aaacccagcg cacctgttag agtcgtcact ctctattgtc
```

```
3061 atggggatca attttcatta aacttgaagc agtcgtggct ttggcagtgt tttggttcag 3121 acacctgttc acagaaaaag catgatggga aaatatttcc tgacttgagt gttccttttt 3181 aaatgtgaat ttttatttct ttttaattat tttaaaatat ttaaacctttt ttcttgatct 3241 taaagatcgt gtagattggg gttggggagg gatgaagggc gagtgaatct aaggataatg 3301 aaataatcag tgactgaaac cattttccca tcatcctttg ttctgagcat tcgctgtacc 3361 ctttaagata tccatctttt tcttttaac cctaatcttt cacttgaaag attttattgt 3421 ataaaaagtt tcacaggtca ataaacttag aggaaaatga gtatttggtc caaaaaaagg 3481 aaaaataatc aagattttag ggcttttatt ttttcttttg taattgtgta aaaaatggaa 3541 aaaaacataa aaagcagaat tttaatgtga agacattttt tgctataatc attagtttta 3601 gaggcattgt tagtttagtg tgtgtgcaga gtccatttcc cacatctttc ctcaagtatc 3661 ttctatttt atcatgaatt ccctttttaat caactgtagg ttatttaaaa taaattccta 3721 caacttaatg gaaa
```

SEQ ID NO: 4
ND(SP)QIEADFRLNDC

---

The invention claimed is:

1. An assay comprising:
   (a) adding an antibody to a cancer biopsy sample from a subject identified as having cancer, wherein the antibody specifically binds to the phosphorylated serine 10 (S10) on the topoisomerase I polypeptide in the sample;
   (b) measuring the binding of the antibody to phosphorylated serine 10 (S10) on the topoisomerase I polypeptide in the cancer biopsy sample; and
   (c) identifying the likelihood of the cancer of the subject to be unresponsive to a topoisomerase I inhibitor by comparing the level of antibody binding to phosphorylated serine 10 (S 10) on the topoisomerase I polypeptide in the biopsy sample to a reference level of antibody binding to phosphorylated serine 10 (S10) on the topoisomerase I polypeptide; and
   (d) determining whether and to what degree the cancer of the subject is likely to be unresponsive to a treatment with topoisomerase I inhibitor based upon that comparison,
   wherein the antibody does not bind to the unphosphorylated topoisomerase I polypeptide.

2. The assay of claim 1, wherein the topoisomerase I inhibitor is camptothecin (CPT), topotecan and irinotecan or an analogue or mimetic thereof.

3. The assay of claim 1, wherein the subject is human.

4. The assay of claim 1, wherein the antibody is selected from the group consisting of: recombinant antibodies, chimeric antibodies, tribodies, midibodies and derivatives and fragments thereof.

5. The assay of claim 4, wherein the antibody is used in a method selected from the group consisting of; immunoblot analysis, immunohistochemical analysis; ELISA, isoform-specific chemical or enzymatic cleavage, protein array or mass spectrometry.

6. The assay of claim 1, wherein the cancer is a refractory cancer or a cancer selected from the group of: gastrointestinal cancer, prostate cancer, ovarian cancer, breast cancer, squamous cell carcinomas (SCC), squamous cell carcinomas (SCC) of the head, neck lung and esophagus, head and neck cancer, lung cancer, non-small cell lung cancer (SCLC), cancer of the nervous system, brain cancer, bone-marrow cancer, bone cancer, kidney cancer, retina cancer, skin cancer, bladder cancer, colon cancer, esophageal cancer, testicular cancer, cervical cancer, liver cancer, renal cancer, pancreatic cancer, genital-urinary cancer, gastrointestinal, gum cancer, tongue cancer, kidney cancer, nasopharynx cancer, stomach cancer, endometrial cancer and bowel tumor cell cancer.

7. The assay of claim 1, further comprising treating the subject with the topoisomerase I inhibitor when the antibody does not show significant binding to the phosphorylated topoisomerase I polypeptide.

* * * * *